United States Patent
Fram

(10) Patent No.: US 9,606,584 B1
(45) Date of Patent: Mar. 28, 2017

(54) SYSTEMS AND USER INTERFACES FOR DYNAMIC INTERACTION WITH TWO- AND THREE-DIMENSIONAL MEDICAL IMAGE DATA USING HAND GESTURES

(71) Applicant: D.R. Systems, Inc., San Diego, CA (US)

(72) Inventor: Evan K. Fram, Phoenix, AZ (US)

(73) Assignee: D.R. SYSTEMS, INC., San Diego, CA (US)

( * ) Notice: Subject to any disclaimer, the term of this patent is extended or adjusted under 35 U.S.C. 154(b) by 0 days.

(21) Appl. No.: 14/754,178

(22) Filed: Jun. 29, 2015

Related U.S. Application Data

(60) Provisional application No. 62/108,167, filed on Jan. 27, 2015, provisional application No. 62/019,760, filed on Jul. 1, 2014.

(51) Int. Cl.
*G06T 15/00* (2011.01)
*G06F 1/16* (2006.01)
(Continued)

(52) U.S. Cl.
CPC ............ *G06F 1/1694* (2013.01); *A61B 19/52* (2013.01); *G02B 27/017* (2013.01); *G06F 3/017* (2013.01);
(Continued)

(58) Field of Classification Search
CPC ...... G06F 1/1694; G06F 19/322; G06F 3/017; G02B 27/017; G06T 15/08; G06T 7/0044;
(Continued)

(56) References Cited

U.S. PATENT DOCUMENTS

| | | |
|---|---|---|
| 5,594,469 A | 1/1997 | Freeman |
| 6,002,808 A | 12/1999 | Freemand |

(Continued)

OTHER PUBLICATIONS

Agfa HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.

(Continued)

*Primary Examiner* — Martin Mushambo
(74) *Attorney, Agent, or Firm* — Knobbe, Martens, Olson & Bear LLP

(57) ABSTRACT

Embodiments of the present disclosure relate to systems and techniques for accessing data stores of medical images and displaying the medical images in substantially real-time to provide information in an interactive user interface. Systems are disclosed that may advantageously provide highly efficient, intuitive, and rapid dynamic interaction with two- and three-dimensional medical image data using hand gestures. The systems may include interactive user interfaces that are dynamically updated to provide tracking of a user's hand in a virtual 3D space by two- and/or three-dimensional image data. A user may use the systems described herein to more quickly, thoroughly, and efficiently interact with image data including two-dimensional images, three-dimensional image data, and/or series of image data, as compared to previous systems.

20 Claims, 39 Drawing Sheets

(51) Int. Cl.
| | | |
|---|---|---|
| *A61B 19/00* | (2006.01) | |
| *G06T 19/00* | (2011.01) | |
| *G06T 15/08* | (2011.01) | |
| *G06T 11/00* | (2006.01) | |
| *G06T 11/40* | (2006.01) | |
| *G06T 7/00* | (2017.01) | |
| *G06F 3/01* | (2006.01) | |
| *G06F 19/00* | (2011.01) | |
| *G02B 27/01* | (2006.01) | |

(52) U.S. Cl.
CPC .......... *G06F 19/322* (2013.01); *G06T 7/0012* (2013.01); *G06T 7/0044* (2013.01); *G06T 7/0053* (2013.01); *G06T 7/0081* (2013.01); *G06T 11/003* (2013.01); *G06T 11/40* (2013.01); *G06T 15/08* (2013.01); *G06T 19/006* (2013.01); *G02B 2027/0178* (2013.01); *G06T 2200/04* (2013.01); *G06T 2207/10072* (2013.01); *G06T 2207/20101* (2013.01); *G06T 2207/30004* (2013.01); *G06T 2207/30196* (2013.01); *G06T 2207/30244* (2013.01); *G06T 2210/41* (2013.01); *G06T 2215/06* (2013.01); *G06T 2219/008* (2013.01); *G06T 2219/2004* (2013.01); *G06T 2219/2016* (2013.01)

(58) Field of Classification Search
CPC ..... G06T 7/0081; G06T 11/40; G06T 7/0012; G06T 11/003; G06T 19/006; G06T 7/0053; G06T 2207/30244; A61B 19/52
See application file for complete search history.

(56) References Cited

U.S. PATENT DOCUMENTS

| | | | | |
|---|---|---|---|---|
| 2002/0028006 | A1* | 3/2002 | Novak | G06F 19/321 382/128 |
| 2008/0114615 | A1 | 5/2008 | Mahesh | |
| 2008/0150937 | A1* | 6/2008 | Lundstrom | G06T 15/08 345/419 |
| 2011/0193939 | A1 | 8/2011 | Vassigh | |
| 2012/0200494 | A1 | 8/2012 | Perski | |
| 2013/0033571 | A1 | 2/2013 | Steen | |
| 2013/0187903 | A1* | 7/2013 | Papageorgiou | G06T 19/00 345/419 |
| 2013/0249786 | A1 | 9/2013 | Wang | |
| 2014/0324400 | A1 | 10/2014 | Quam | |
| 2014/0368428 | A1 | 12/2014 | Pinault | |

OTHER PUBLICATIONS

Agfa HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.

AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.

ASPYRA's Imaging Solutions, 3 page color print out. Accessed at http://www.aspyra.com/imaging-solutions. Accessed on Feb. 9, 2015.

Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.

BRIT Systems, BRIT PACS View Viewer, 2 page color brochure, (BPB-BPV-0001). Downloaded from http://www.brit.com/pdfs/britpacsview.pdf. Accessed on Feb. 9, 2015.

BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.

BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.

CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.

Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.

Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.

Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.

CoActiv, EXAM-PACS, 2 page color brochure, © 2014 CoActiv, LLC. Downloaded from http//coactiv.com/wp-content/uploads/2013/08/EXAM-PACS-BROCHURE-final-web.pdf. Accessed on Feb. 9, 2015.

DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.

DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.

Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.

Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.

Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.

GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.

Handylife.com—Overview of Handy Patients Enterprise, in 2 page printout. Accessed from http://www.handylife.com/en/software/overview.html. Accessed on Feb. 18, 2015.

Handylife.com—Features of Handy Patients Enterprise, in 4 page printout. Accessed from http:/www.handylife.com/en/software/features.html. Accessed on Feb. 18, 2015.

Handylife.com—Screenshots of Handy Patients Enterprise, in 2 page printout. Accessed from http://www.handylife.com/en/software/screenshots.html. Accessed on Feb. 18, 2015.

iCRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.

Imageanalysis, dynamika, 2 page color brochure. Downloaded from http://www.imageanalysis.org.uk/what-we-do. Accessed on Feb. 9, 2015.

(56) References Cited

OTHER PUBLICATIONS

Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.Intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsolus.com/01_products/products_01.html. Accessed on Feb. 9, 2015.

Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Sclmage, Cardiology PACS, in 8 color page printout. Accessed at http://www.scimage.com/solutions/cilnical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 Jan. 2007). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.

\* cited by examiner

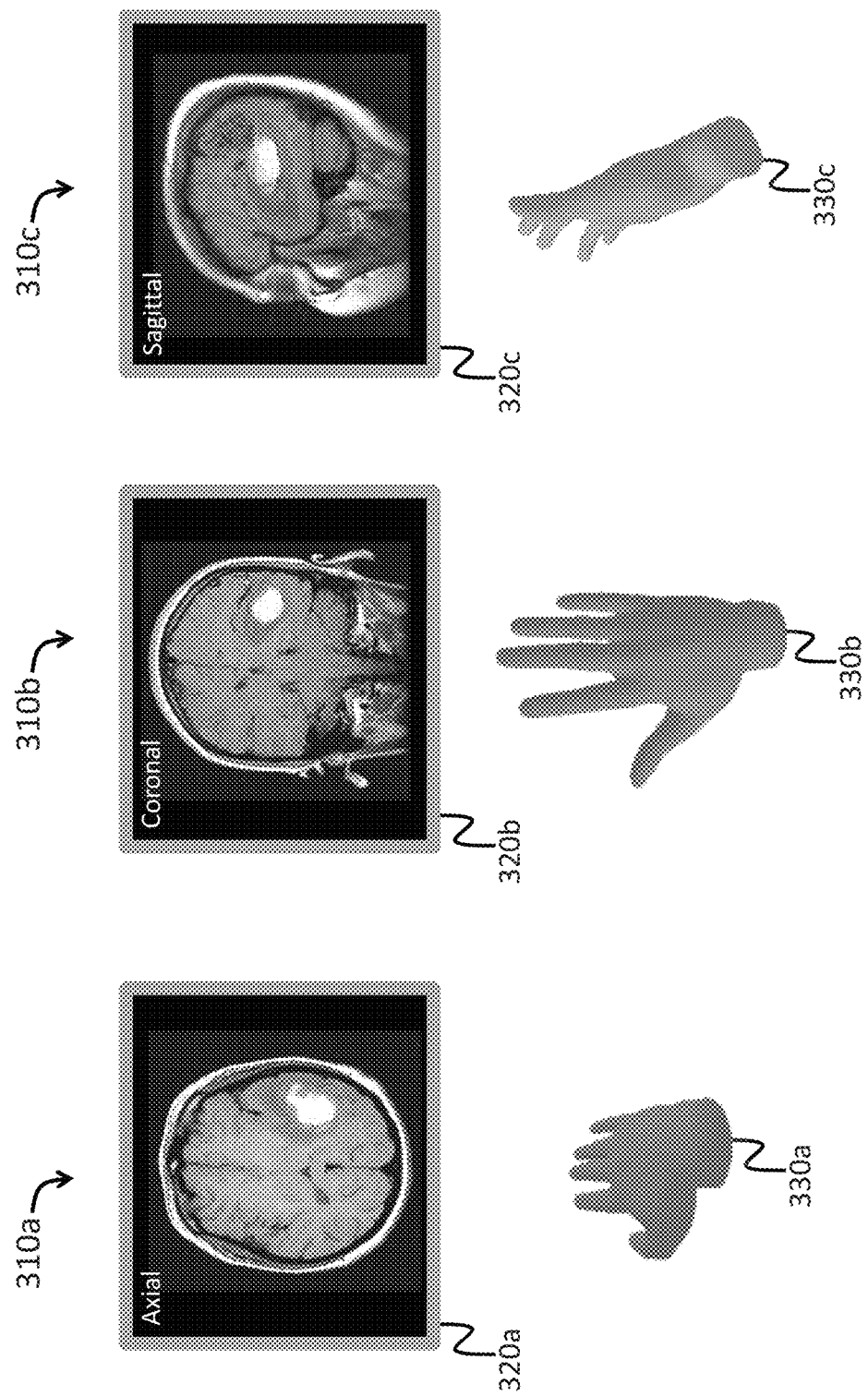

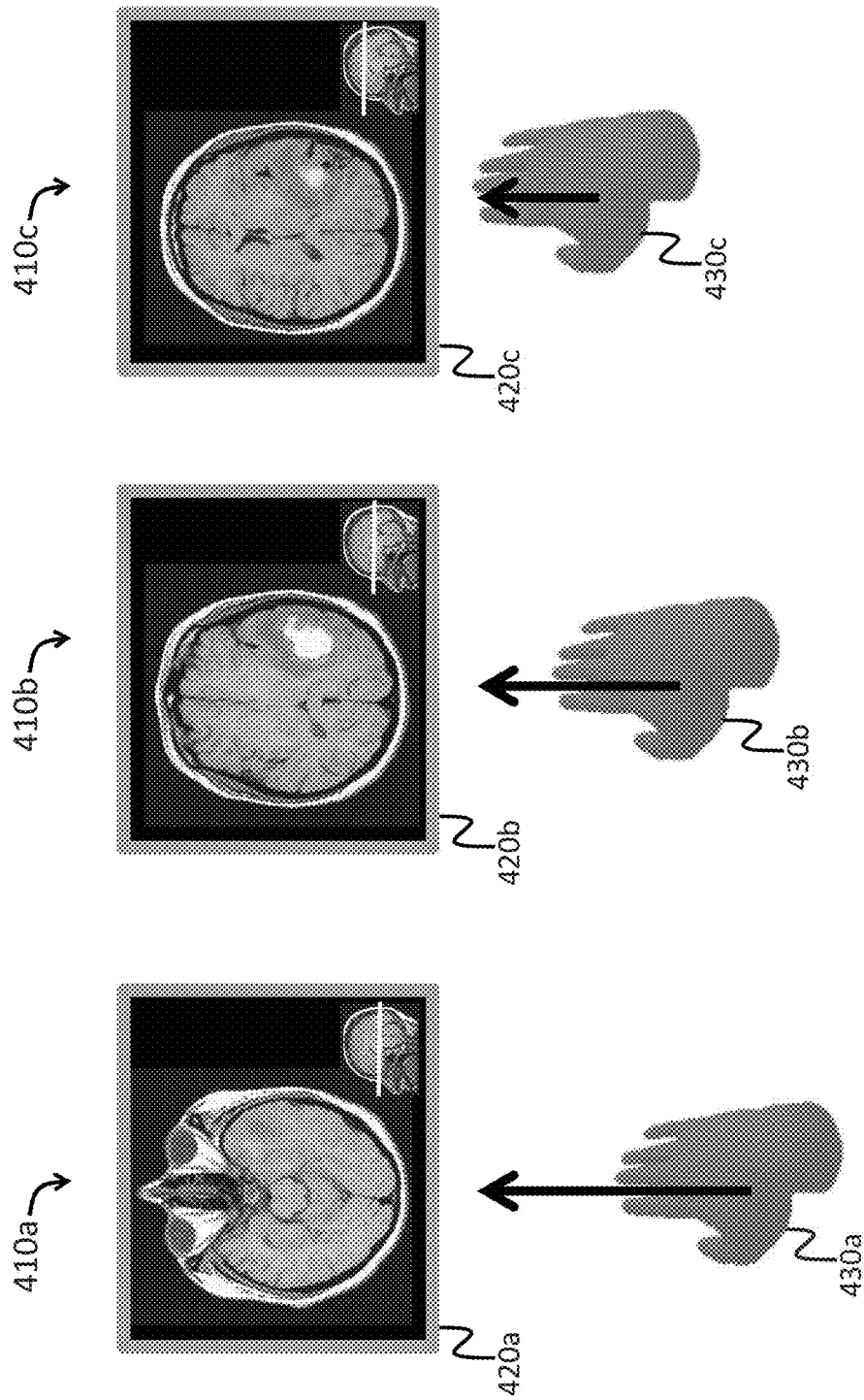

| User Preferences | Rules | |
|---|---|---|
| | User Input | Effect |
| User 1 | Hand Orientation | Select series |
| | Hand Movement Along Axis Normal to Plane of Hand | Select image in series |
| Group 1 | Hand Orientation | Select series |
| | If Sagittal Series, Hand Movement Along Axis Normal to Plane of Hand | Select image in series |
| | If Axial Series, Hand Movement Along Axis Parallel to Plane of Hand | Select image in series |
| Site 1 | Hand Orientation | Select series |
| | Absolute Position of Hand in Space | Select image in series |

Fig. 7B

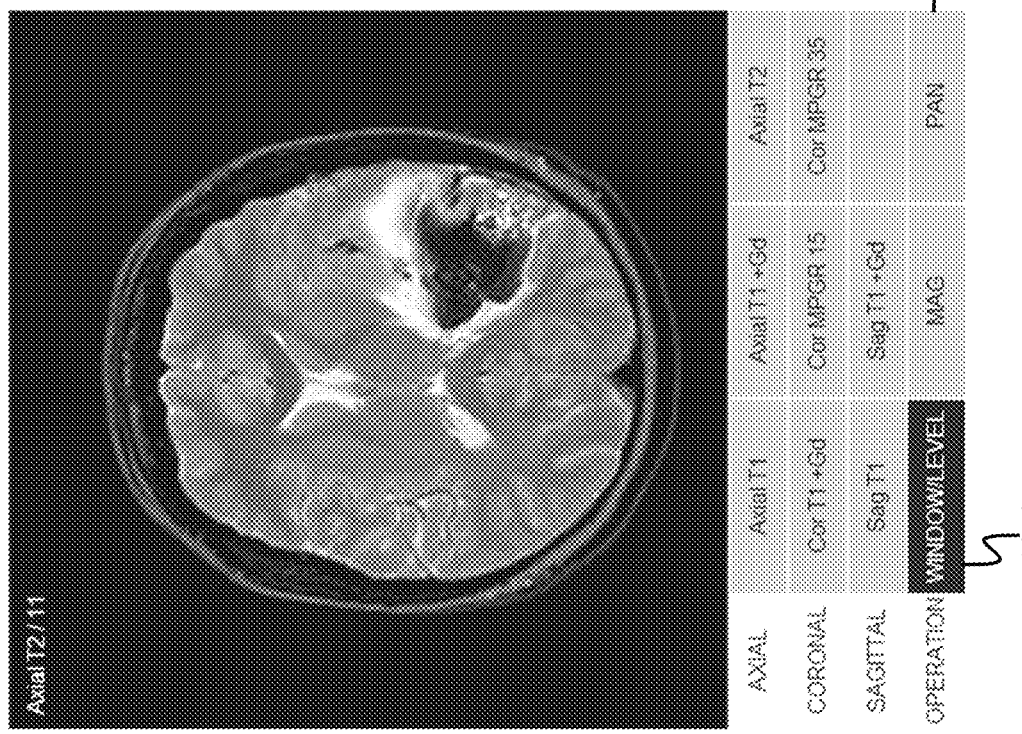

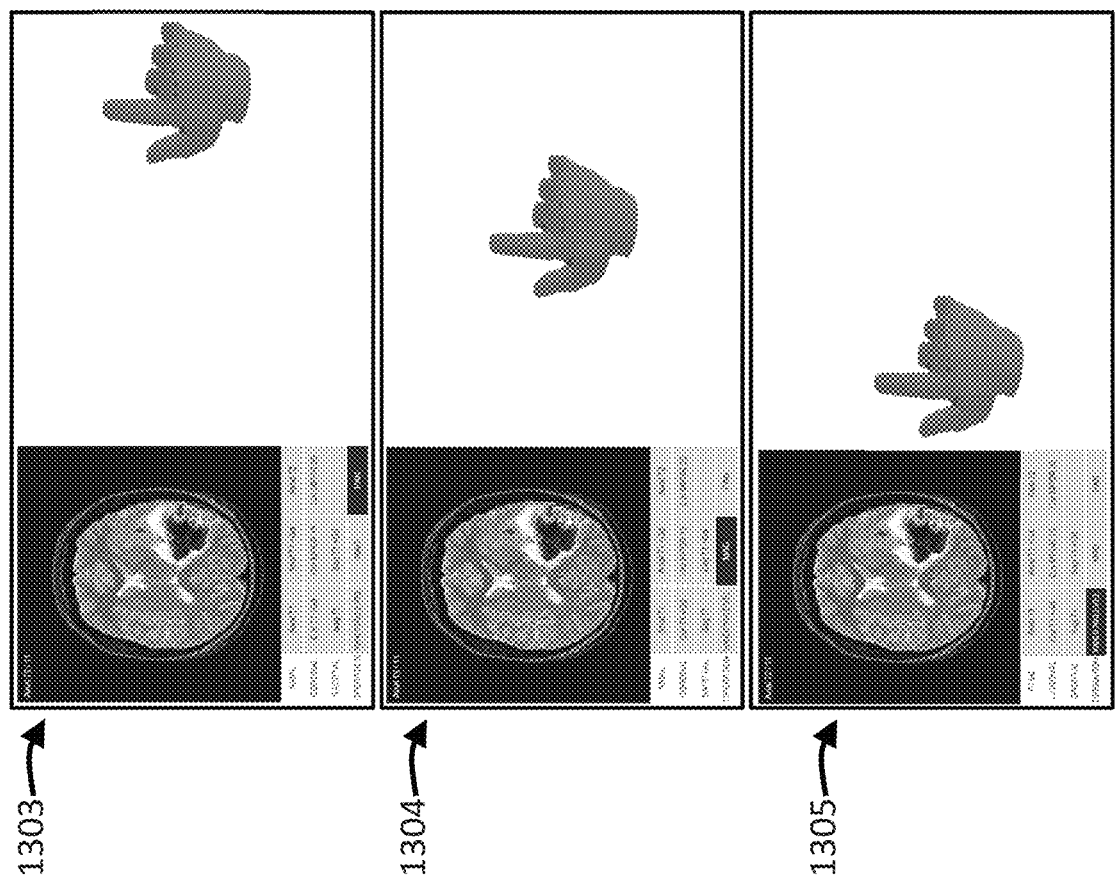

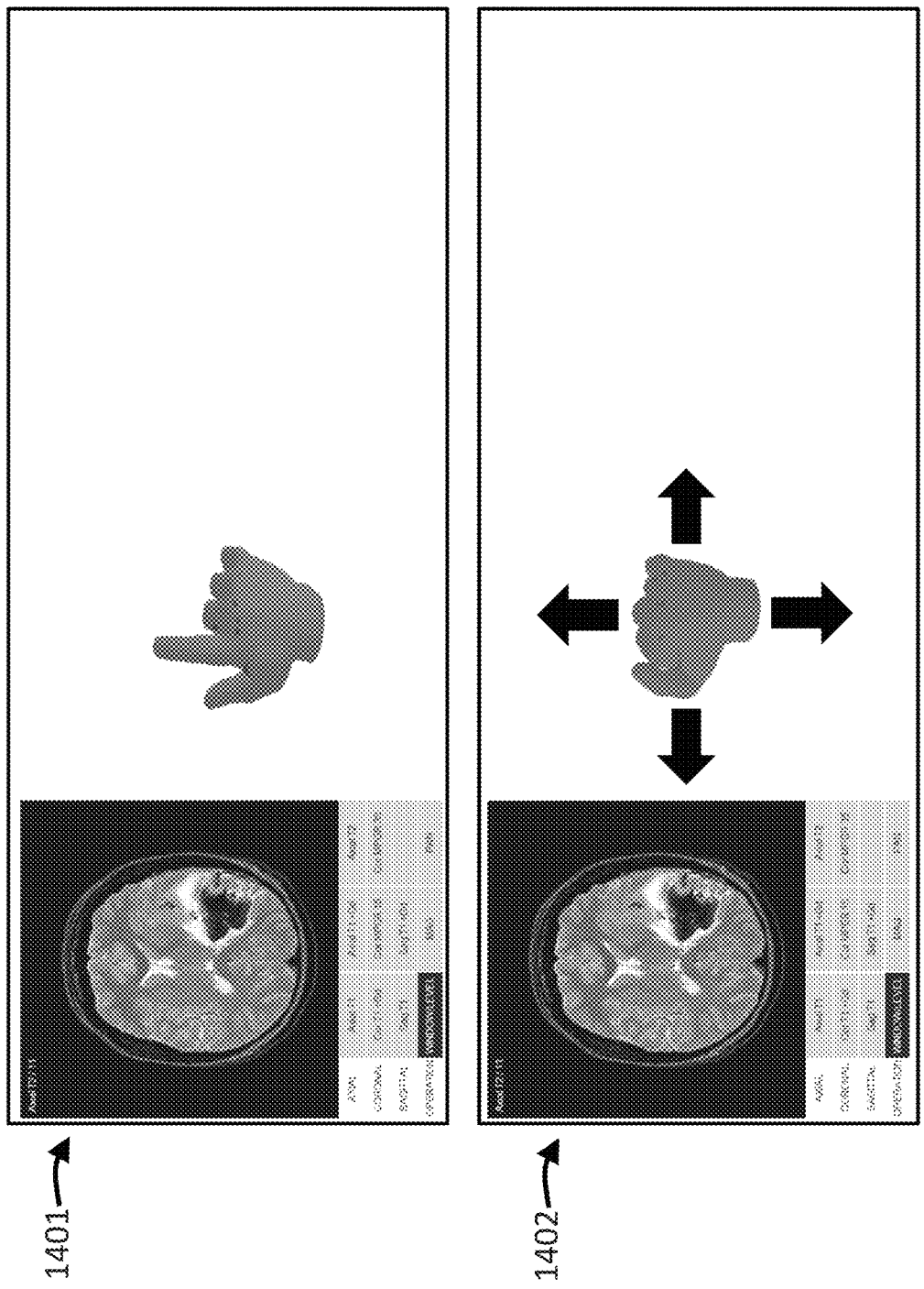

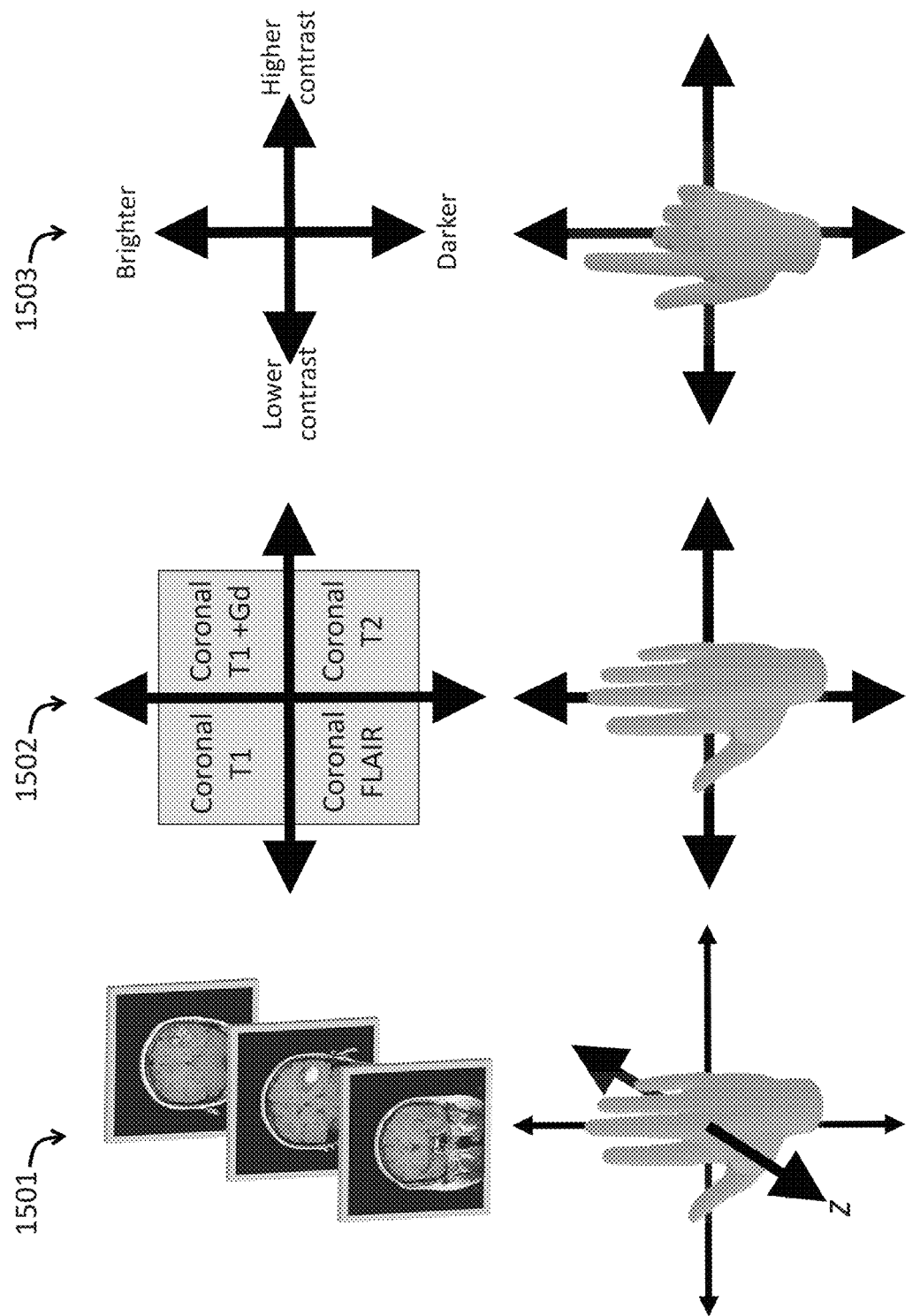

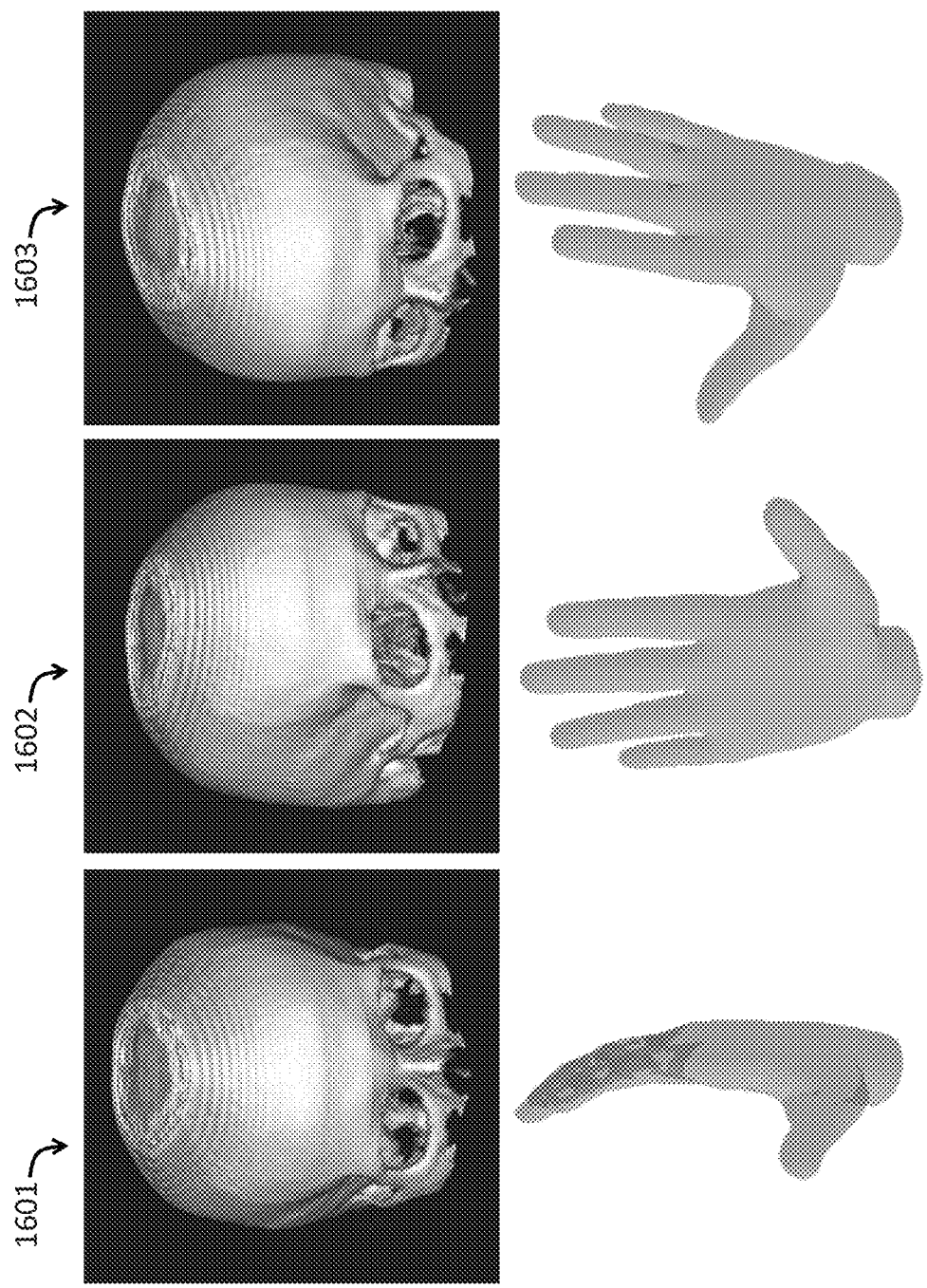

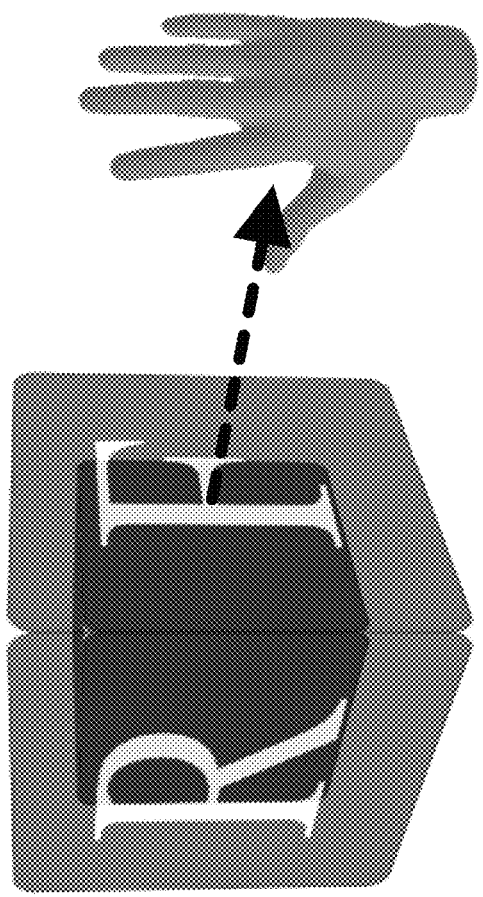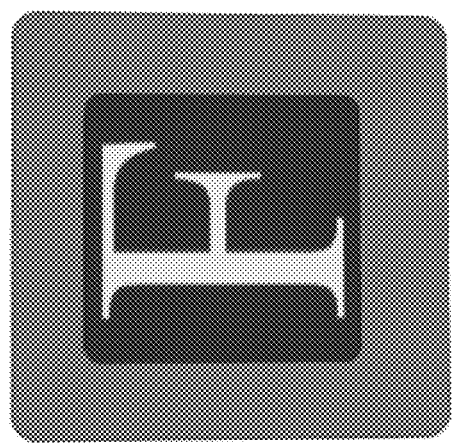
Fig. 24

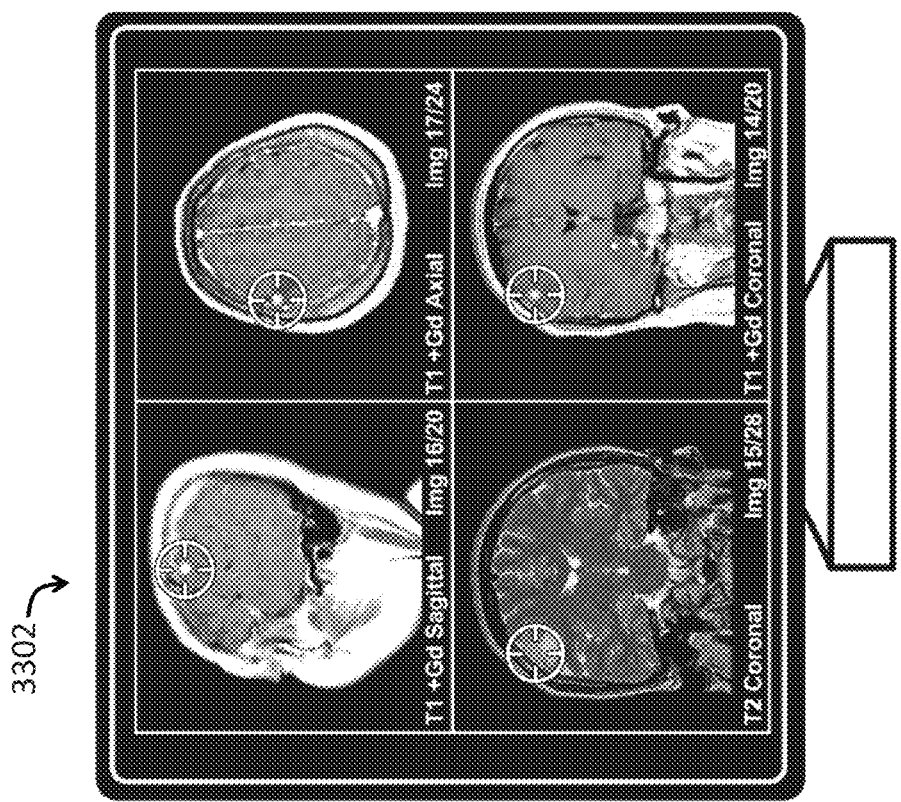
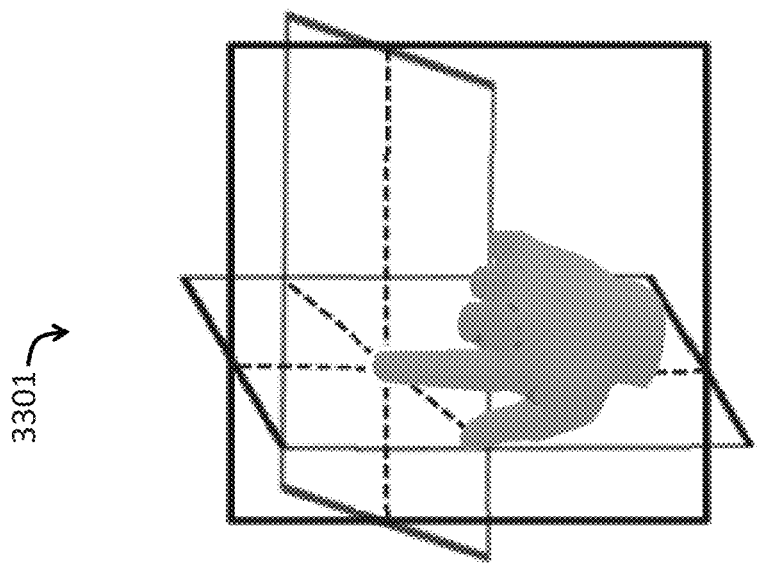
Fig. 33

SYSTEMS AND USER INTERFACES FOR DYNAMIC INTERACTION WITH TWO- AND THREE-DIMENSIONAL MEDICAL IMAGE DATA USING HAND GESTURES

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

This application claims benefit of U.S. Provisional Patent Application No. 62/019,760, filed Jul. 1, 2014, titled "IMAGE NAVIGATION WITH 3D GESTURES," and also claims benefit of U.S. Provisional Patent Application No. 62/108,167, filed Jan. 27, 2015, titled "IMAGE NAVIGATION WITH 3D GESTURES." The entire disclosure of each of the above items is hereby made part of this specification as if set forth fully herein and incorporated by reference for all purposes, for all that it contains.

TECHNICAL FIELD

Embodiments of the present disclosure relate to systems and techniques for dynamic interactions with medical image data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Many existing vendors offer software that creates and displays images, including the display of color or grayscale images that appear to be three dimensional. In the field of medical imaging, these images are typically based on data describing a volume of material or human tissue. Devices such as CT, MRI, PET, and Ultrasound can generate data describing a volume of human or animal tissue. Caregivers may display these volumes in a manner such that one or more images appear to be three dimensional using techniques such as volume rendering and surface shading. In addition, such software many enable the user to perform multi-planar reconstructions, maximum intensity pixel displays, or display grayscale or color slabs of various thickness and orientations.

Medical images are typically viewed by radiologists and other physicians, patients, and/or others by interaction with desktop computer systems with stationary monitors. Interaction with images in such systems typically utilizes keyboard and/or mouse input. For example, the reviewing physician may move from one image to the next by pressing an arrow key, and/or may zoom an image in or out by movement of the mouse or scroll wheel. Such systems are not ideal for at least two reasons. First, medical images may be very large and include significant detail (for example, be very high resolution). Zooming into and scrolling around such images using a keyboard and mouse may be cumbersome, time consuming, and inefficient. Second, medical images are frequently part of a large series of images, or generated from a large amount of three-dimensional image data. Moving through such series of images and/or three-dimensional image data using a keyboard and mouse may also be cumbersome, time consuming, and inefficient.

SUMMARY

The systems, methods, and devices described herein each have several aspects, no single one of which is solely responsible for its desirable attributes. Without limiting the scope of this disclosure, several non-limiting features will now be described briefly.

Embodiments of the present disclosure relate to systems and techniques for accessing data stores of medical images and displaying the medical images in substantially real-time to provide information in an interactive user interface. As described above, previous systems for display of, and interaction with, image data were typically cumbersome, time consuming, and inefficient for the user. Disclosed herein are systems that, according to various embodiments, advantageously provide highly efficient, intuitive, and rapid dynamic interaction with two- and three-dimensional image data using hand gestures. The systems may include interactive user interfaces that are dynamically updated to provide tracking of a user's hand in a virtual 3D space by two- and/or three-dimensional image data. Accordingly, a user may use the systems described herein to more quickly, thoroughly, and efficiently interact with image data including two-dimensional images, three-dimensional image data, and/or series of image data, as compared to previous systems. The features and advantages noted above, as well as others, are discussed in further detail below.

According to various embodiments, a data navigation system is disclosed in which a user may interact with image data (including two-dimensional and three-dimensional), such as medical images and/or rendered volumetric medical imaging data, via hand gestures and other user inputs. In various embodiments described herein, an orientation, configuration, motion and/or position of a user's hand is used to, for example:

select series of images within medical imaging exams;
navigate through images within an image series;
select operations to be performed on images and/or series;
provide input to a selected operation to be performed on images and/or series;
provide input to 3D rendering software, for example to control the 3D view rendered by 3D volume rendering software; and
provide input to control the location and/or orientation of an image reconstructed using multiplanar reformation (MPR) or maximum intensity projection (MIP) software;
among other features.

In addition to providing improved methods of interacting with images and 3D imaging information that are more efficient and intuitive, some of the methods described herein require no physical contract with a mouse or other input device and may be advantageous in scenarios where it is important to maintain sterility, such as operating rooms and intensive care units.

It has been noted that design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The present disclosure describes various embodiments of interactive and dynamic user interfaces that are the result of significant development. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the hand gestures and other inputs described herein may provide an optimized display of, and interaction with, image data (both two- and three-dimensional) and may enable a user to more quickly access, navigate, assess, and digest the image data than previous systems.

Further, the interactive and dynamic user interfaces described herein are enabled by innovations in efficient interactions between the user interfaces and underlying systems and components. For example, disclosed herein are improved methods of receiving user inputs (including hand gestures and/or the like), translation and delivery of those inputs to various system components, automatic and dynamic execution of complex processes in response to the input delivery, automatic interaction among various components and processes of the system, and automatic and dynamic updating of the user interfaces (to, for example, display the relevant portions of the image data). The interactions and presentation of data via the interactive user interfaces described herein may accordingly provide cognitive and ergonomic efficiencies and advantages over previous systems.

Various embodiments of the present disclosure provide improvements to various technologies and technological fields. For example, as described above, existing medical image interaction technology (including, e.g., Picture Archiving and Communication Systems, Electronic Medical Record Systems, and/or the like) is limited in various ways (e.g., image review can be slow and cumbersome using a mouse and keyboard, etc.), and various embodiments of the disclosure provide significant improvements over such technology. Additionally, various embodiments of the present disclosure are inextricably tied to computer technology. In particular, various embodiments rely on detection of user inputs by specialized electronic sensors, calculation of updates to displayed electronic data based on those user inputs, and presentation of the updates via interactive graphical user interfaces. Such features are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic data.

According to an embodiment, a medical image computing system is disclosed comprising: an electronic display; one or more sensors configured to detect a hand of a user; a storage device configured to store electronic software instructions; and one or more computer processors in communication with the electronic display, the one or more sensors, and the storage device, the one or more computer processors configured to execute the stored software instructions to cause the computing system to: determine a user input based on the hand of the user as detected by the one or more sensors; based on the user input, determine a first medical image to display; and generate user interface data for rendering an interactive user interface on the electronic display, the interactive user interface including the first medical image.

According to an aspect, the user input comprises at least one of: a motion of the hand, a rotation of the hand, an orientation of the hand, a configuration of the hand, or a position of the hand.

According to another aspect, at least one of the one or more sensors is located on a surface in front of and below the electronic display such that the one or more sensors are configured to detect the hand of the user when the hand is positioned above the sensor and in front of the electronic display.

According to yet another aspect, at least one of the one or more sensors is attached to the user.

According to another aspect, the medical image computing system further comprises: one or more data stores storing a plurality of medical exams, each medical exam including at least one of volumetric image data or one or more image series, each image series including one or more medical images, each image series associated with an imaging plane, wherein the first medical image is from a first medical exam.

According to yet another aspect, determining the user input comprises: determining, based on the hand of the user as detected by the one or more sensors, a plane of the hand of the user; and determining the first medical image to display comprises: determining, based on the plane of the hand of the user, an imaging plane; and selecting, based on the imaging plane, at least one of: a first medical image of an image series of the one or more image series of the first medical exam, wherein the image series is associated with the imaging plane, or a first medical image reconstructed from a portion of the volumetric image data of the first medical exam, wherein the portion of the volumetric image data corresponds to the imaging plane.

According to another aspect, subsequent to the interactive user interface including the first medical image, the one or more computer processors are configured to execute the stored software instructions to further cause the computing system to: determine a second user input based on the hand of the user as detected by the one or more sensors, the second user input including a motion of the hand of the user; based on the second user input, at least one of: selecting a second medical image of the image series associated with the imaging plane, wherein the second medical image is selected based on at least one of an amount of motion of the hand or an absolute position of the hand, or reconstructing a second medical image from a second portion of the volumetric image data of the first medical exam, wherein the second portion of the volumetric image data corresponds to the imaging plane, wherein the second portion of the volumetric image data is selected based on at least one of an amount of motion of the hand or an absolute position of the hand; and update the user interface data such that the interactive user interface includes the second medical image.

According to yet another aspect, the motion of the hand of the user is along a plane parallel to the plane of the hand.

According to another aspect, the motion of the hand of the user is along an axis perpendicular to the plane of the hand.

According to yet another aspect, determining the user input comprises: determining, based on the hand of the user as detected by the one or more sensors, a plane of the hand of the user and a motion of the hand of the user; and determining the first medical image to display comprises: determining, based on the plane of the hand of the user, an imaging plane; in response to the motion of the hand being parallel to the plane of the hand: selecting, based on at least one of an amount of motion of the hand or an absolute position of the hand, at least one of: an image series of the one or more image series of the first medical exam, wherein the image series is associated with the imaging plane, or a volumetric image data of the first medical exam; and selecting a first medical image of the image series or reconstructed from a portion of the volumetric image data based on a position of the hand; and in response to the motion of the hand being perpendicular to the plane of the hand: selecting, based on at least one of an amount of motion of the hand or an absolute position of the hand, at least one of: a first medical image of the image series, or a first medical image reconstructed from a portion of the volumetric image data, wherein the portion of the volumetric image data corresponds to the imaging plane.

According to another aspect, determining a first medical image to display comprises: accessing a plurality of rules associated with the user, the rules indicating associations among user inputs and effects with respect to displayed medical images; determining a rule of the plurality of rules that is associated with the user input; selecting the first medical image based on an effect associated with the rule.

According to yet another aspect, the one or more computer processors are configured to execute the stored software instructions to further cause the computing system to: determine a second user input based on the hand of the user as detected by the one or more sensors; determine a relative change in the hand of the user from the user input to the second user input; based on the relative change in the hand of the user, determine a second medical image to display; and update the user interface data such that the user interface includes the second medical image in place of the first medical image.

According to another aspect, the one or more computer processors are configured to execute the stored software instructions to further cause the computing system to: determine a second user input based on the hand of the user as detected by the one or more sensors; determine an absolute spatial position of the hand of the user in response to the second user input; based on the absolute spatial position of the hand of the user, determine a second medical image to display; and update the user interface data such that the user interface includes the second medical image in place of the first medical image.

According to another embodiment, a medical image computing system is disclosed comprising: an electronic display; one or more sensors configured to detect a hand of a user; one or more data stores storing a plurality of medical exams, each medical exam including one or more image series, each image series including one or more medical images, each image series associated with an imaging plane; a storage device configured to store electronic software instructions; and one or more computer processors in communication with the electronic display, the one or more sensors, and the storage device, the one or more computer processors configured to execute the stored software instructions to cause the computing system to: detect, by the one or more sensors, a plane of the hand of the user; determine, based on the plane of the hand of the user, an imaging plane; select, from one or more image series of a first medical exam, a first image series associated with the imaging plane; select, from a the first image series, a first medical image including image data of a first anatomical location; detect, by the one or more sensors, a motion of the hand of the user; in response to the motion of the hand being parallel to the plane of the hand: select, based on at least one of an amount of motion of the hand or an absolute position of the hand, a second image series of the one or more image series of the first medical exam, wherein the second image series is associated with the imaging plane; and select, from a the second image series, a second medical image including image data of an anatomical location that is the same as the first anatomical location; in response to the motion of the hand being perpendicular to the plane of the hand: select, based on at least one of an amount of motion of the hand or an absolute position of the hand, a second medical image from the first image series; and generate user interface data for rendering an interactive user interface on the electronic display, the interactive user interface including at least one of the first medical image from the first image series, the second medical image from the first image series, or the second medical image from the second image series.

According to yet another embodiment, a medical image computing system is disclosed comprising: an electronic display; one or more sensors configured to detect a hand of a user; one or more data stores storing a plurality of medical exams, each medical exam including at least one of volumetric image data or one or more image series, each image series including one or more medical images, each image series associated with an imaging plane; a storage device configured to store electronic software instructions; and one or more computer processors in communication with the electronic display, the one or more sensors, and the storage device, the one or more computer processors configured to execute the stored software instructions to cause the computing system to: detect, by the one or more sensors, a first user input including at least a position of the hand; determine, based on the position of the hand, a first display orientation; generate user interface data for rendering an interactive user interface on the electronic display, the interactive user interface including a 3D display of a first medical exam at the first display orientation; detect, by the one or more sensors, a second user input including at least a configuration of the hand; determine, based on the configuration of the hand, a second medical exam; and update the user interface data such that the interactive user interface includes a 3D display of the second medical exam at the first display orientation.

According to another embodiment, a medical image computing system is disclosed comprising: an electronic display; one or more sensors configured to detect a hand of a user; one or more data stores storing a plurality of medical exams, each medical exam including one or more image series, each image series including one or more medical images, each image series associated with an imaging plane; a storage device configured to store electronic software instructions; and one or more computer processors in communication with the electronic display, the one or more sensors, and the storage device, the one or more computer processors configured to execute the stored software instructions to cause the computing system to: detect, by the one or more sensors, a first user input including at least an orientation, a position, and a configuration of the hand; determine, based on the configuration of the hand, a first medical exam; determine, based on the orientation of the hand, a first imaging plane; determine, based on the position of the hand, a first image series of the first medical exam, wherein the first image series is associated with the first imaging plane; determine, based on the position of the hand, a first medical image of the first image series; generate user interface data for rendering an interactive user interface on the electronic display, the interactive user interface including a display of the first medical image; detect, by the one or more sensors, a second user input including a change in at least one of the orientation, the position, or the configuration of the hand; and in response to the second user input: select a second medical image; and update the user interface data such that the interactive user interface includes a display of the second medical image, wherein, in response to the second user input comprising a change in the configuration of the hand, the second medical image is selected from a second medical exam such the that second medical image displays a same anatomical position in a same imaging plane as the first medical image, and the second medical image is selected from a second image series of the second medical exam of a same image series type as the first image series.

According to yet another embodiment, a medical image computing system is disclosed comprising: an electronic display; one or more sensors configured to detect a hand of a user; a storage device configured to store electronic software instructions; one or more data stores storing a plurality of medical exams, each medical exam including at least one of volumetric image data or one or more image series, each image series including one or more medical images, each image series associated with an imaging plane; and one or more computer processors in communication with the electronic display, the one or more sensors, the storage device, and the one or more data stores, the one or more computer processors configured to execute the stored software instructions to cause the computing system to: determine, based on the hand of the user as detected by the one or more sensors: a plane of the hand of the user; and a position of the hand of the user; determine, based on the plane of the hand of the user, a first imaging plane; determine, based on the position of the hand of the user, a first image series type associated with the first imaging plane; select a first image series of the one or more image series of a first medical exam, the first image series having the first image series type; select, further based on the position of the hand of the user, a first medical image of the first image series; and generate user interface data for rendering an interactive user interface on the electronic display, the interactive user interface including the first medical image.

According to another aspect, the one or more computer processors are configured to execute the stored software instructions to further cause the computing system to: detect, by the one or more sensors, a motion of the hand of the user along the plane of the hand of the user; determine an updated position of the hand of the user; determine, based on the updated position of the hand of the user, a second image series type associated with the first imaging plane; select a second image series of the one or more image series of the first medical exam, the second image series having the second image series type; select, further based on the updated position of the hand of the user, a second medical image of the second image series; and update the user interface data such that the interactive user interface includes the second medical image.

According to yet another aspect, the one or more computer processors are configured to execute the stored software instructions to further cause the computing system to: detect, by the one or more sensors, a motion of the hand of the user along an axis perpendicular to the plane of the hand of the user; select, based on the motion of the hand of the user, a second medical image of the first image series; and update the user interface data such that the interactive user interface includes the second medical image.

According to another aspect, the one or more computer processors are configured to execute the stored software instructions to further cause the computing system to: detect, by the one or more sensors, a motion of the hand of the user; determine: an updated plane of the hand of the user; and an updated position of the hand of the user; determine, based on the updated plane of the hand of the user, a second imaging plane; determine, based on the updated position of the hand of the user, a second image series type associated with the second imaging plane; select a second image series of the one or more image series of a first medical exam, the second image series having the second image series type; select, further based on the position of the hand of the user, a second medical image of the second image series; and update the user interface data such that the interactive user interface includes the second medical image.

According to yet another aspect, determining the first image series type associated with the first imaging plane comprises: accessing a hanging protocol associated with the user; and determining the first series type by mapping the position of the hand of the user to the hanging protocol.

According to another aspect, the one or more computer processors are configured to execute the stored software instructions to further cause the computing system to: detect, by the one or more sensors, a configuration of the hand of the user; select, based on the configuration of the hand of the user and the position of the hand of the user, an operation to perform on the first medical image; detect, by the one or more sensors, a motion of the hand of the user while in the configuration; and implement the operation on the first medical image in proportion to the motion of the hand of the user.

According to yet another aspect, the operation is at least one of: an adjustment of a window, and adjustment of a level, an adjustment of a magnification, or a pan adjustment.

According to another embodiment, a medical image computing system is disclosed comprising: an electronic display; one or more sensors configured to detect a hand of a user; a storage device configured to store electronic software instructions; one or more data stores storing a plurality of medical exams, each medical exam including at least one of volumetric image data or one or more image series, each image series including one or more medical images, each image series associated with an imaging plane; and one or more computer processors in communication with the electronic display, the one or more sensors, the storage device, and the one or more data stores, the one or more computer processors configured to execute the stored software instructions to cause the computing system to: generate user interface data for rendering an interactive user interface on the electronic display, the interactive user interface including a medical image; determine, based on the hand of the user as detected by the one or more sensors, a configuration of the hand of the user; in response to determining that the configuration of the hand of the user matches a first configuration, select a first mode of operation; in response to determining that the configuration of the hand of the user matches a second configuration, select a second mode of operation; in response to determining that the configuration of the hand of the user matches a third configuration, select a third mode of operation; detect, by the one or more sensors, a motion of the hand of the user; implement, depending on the configuration of the hand, one of the first, second, or third modes of operation in proportion to the motion of the hand; and update the user interface data such that the interactive user interface reflects the implementation of the one of the first, second, or third modes of operation.

According to another aspect, the implemented one of the first, second, or third modes of operation comprises at least one of: a change of a property associated with the medical image, a change to a different medical image within a selected image series, a change of image series within a selected medical exam, or a change of medical exam.

According to yet another aspect, the configuration of the hand of the user comprises at least one of: a fist, one or more fingers extended, or a flat hand.

According to another aspect, the motion of the hand of the user comprises at least one of: a rotation of the hand, a change in orientation of the hand, or a change in position of the hand.

According to yet another embodiment, a medical image computing system is disclosed comprising: an electronic display; one or more sensors configured to detect a hand of a user; a storage device configured to store electronic software instructions; one or more data stores storing a plurality of medical exams, each medical exam including at least one of volumetric image data or one or more image series, each image series including one or more medical images, each image series associated with an imaging plane; and one or more computer processors in communication with the electronic display, the one or more sensors, the storage device, and the one or more data stores, the one or more computer processors configured to execute the stored software instructions to cause the computing system to: determine, based on the hand of the user as detected by the one or more sensors, a plane of the hand of the user; determine, based on the plane of the hand of the user, a first imaging plane; detect, by the one or more sensors, a position of the hand of the user on the plane of the hand of the user; determine, based on the position of the hand of the user, a first image series type associated with the first imaging plane; select a first image series of the one or more image series of a first medical exam, the first image series having the first image series type; select, further based on the position of the hand of the user, a first medical image of the first image series; generate user interface data for rendering an interactive user interface on the electronic display, the interactive user interface including the first medical image; in response to movement of the hand of the user along an axis perpendicular to the plane of the hand of the user: select a second medical image of the first image series; and update the user interface data such that the interactive user interface includes the second medical image; and in response to movement of the hand of the user along the plane of the hand of the user: select a second image series type; select a second image series of the one or more image series of the first medical exam, the second image series having the second image series type; select a second medical image of the second image series; and update the user interface data such that the interactive user interface includes the second medical image.

According to another aspect, the one or more computer processors are configured to execute the stored software instructions to further cause the computing system to: detect a configuration of the hand of the user that is associated with one or more operations to perform on a medical image; in response to movement of the hand of the user in a first direction while the hand of the user is in the detected configuration: apply a first operation of the one or more operations to a medical image included in the interactive user interface; and in response to movement of the hand of the user in a second direction while the hand of the user is in the detected configuration: apply a second operation of the one or more operations to the medical image included in the interactive user interface.

According to yet another aspect, the one or more computer processors are configured to execute the stored software instructions to further cause the computing system to: detect a configuration of the hand of the user that indicates that movement of the hand is to be ignored; and in response to movement of the hand of the user while the hand of the user is in the detected configuration: do not update the user interface data.

According to another embodiment, a medical image computing system for accessing one or more data stores storing volumetric medical image data, receiving sensor data from the one or more sensors indicative of a user input provided via a hand of a user, calculation rotations of, and rendering three-dimensional views of the medical image data based on the sensor data, and generating user interfaces including the rendered three-dimensional views is disclosed, wherein the medical image computing system comprises: an electronic display; one or more sensors configured to detect a hand of a user; a storage device configured to store electronic software instructions; one or more data stores storing at least one set of volumetric medical image data; and one or more computer processors in communication with the electronic display, the one or more sensors, the storage device, and the one or more data stores, the one or more computer processors configured to execute the stored software instructions to cause the computing system to: access, from the one or more data stores, a set of volumetric medical image data; render a three-dimensional view of the set of volumetric medical image data; generate user interface data for rendering an interactive user interface on the electronic display, the interactive user interface including at least the rendered three-dimensional view of the set of volumetric medical image data; determine a virtual origin location in physical space about which a user may move their hand; receive sensor data from the one or more sensors, the sensor data indicative of a user input provided via the hand of the user, the user input comprising at least a position of the hand; determine, based on the sensor data, the position of the hand with respect to the virtual origin location; calculate, based on the position of the hand with respect to the virtual origin location, a rotation of the set of volumetric medical image data; render, based on the rotation, an updated three-dimensional view of the set of volumetric medical image data; and update the user interface data to include the updated three-dimensional view of the set of volumetric medical image data.

According to another aspect, the virtual origin location is determined in reference to at least one of the one or more sensors.

According to yet another aspect, the at least one of the one or more sensors is located on a surface in front of and below the electronic display such that the virtual origin is located in front of the electronic display and the one or more sensors are configured to detect the hand of the user when the hand is positioned above the sensor and in front of the electronic display.

According to another aspect, calculating the rotation of the set of volumetric medical image data comprises: defining a first three-dimensional coordinate system of the at least one of the one or more sensors, wherein the virtual origin is at an origin of the first three-dimensional coordinate system; determining x and z coordinates of the hand with reference to the first three-dimensional coordinate system; calculating a first angle between a z-axis of the first three-dimensional coordinate system and the x and z coordinates of the hand with reference to the first three-dimensional coordinate system; determining a y coordinate of the hand with reference to the first three-dimensional coordinate system; converting the y coordinate to a value on a scale between a maximum value and a minimum value, wherein the maximum value and the minimum value are associated with respective minimum and maximum physical positions of the users hand along a y-axis of the first three-dimensional coordinate system; calculating a second angle by taking an arcsin( ) of the value; defining a second three-dimensional coordinate system of the rendered three-dimensional view of the set of volumetric medical image data; rotating the rendered three-dimensional view of the set of volumetric medical image data by the first angle about a y-axis of the second three-dimensional coordinate system; defining a third three-dimensional coordinate system of the electronic display; and rotating the rendered three-dimensional view of the set of volumetric medical image data by the second angle about an x-axis of the third three-dimensional coordinate system.

According to yet another aspect, the maximum value and minimum value are, respectively, at least one of: −0.99 and +0.99, −0.999 and +0.999, or −1 and +1.

According to another aspect, the user input further comprises at least one of: a motion of the hand, a rotation of the hand, an orientation of the hand, or a configuration of the hand.

According to yet another aspect, the one or more data stores store a first set of volumetric medical image data and a second set of volumetric medical image data, and the one or more computer processors are configured to execute the stored software instructions to further cause the computing system to: determine, based on the sensor data, the configuration of the hand of the user; select, based on the configuration of the hand of the user, a one of the first set of volumetric medical image data and the second set of volumetric medical image data; calculate, based on the position of the hand with respect to the virtual origin location, a first rotation of the one of the first set of volumetric medical image data and the second set of volumetric medical image data; render, based on the first rotation, an updated three-dimensional view of the one of the first set of volumetric medical image data and the second set of volumetric medical image data; and update the user interface data to include the updated three-dimensional view of the one of the first set of volumetric medical image data and the second set of volumetric medical image data.

According to another aspect, the one or more computer processors are configured to execute the stored software instructions to further cause the computing system to: determine, based on the sensor data, a change in the configuration of the hand of the user; select, based on the change in the configuration of the hand of the user, a second of the first set of volumetric medical image data and the second set of volumetric medical image data; calculate, based on the position of the hand with respect to the virtual origin location, a second rotation of the second of the first set of volumetric medical image data and the second set of volumetric medical image data; render, based on the second rotation, an updated three-dimensional view of the second of the first set of volumetric medical image data and the second set of volumetric medical image data; and update the user interface data to include the updated three-dimensional view of the second of the first set of volumetric medical image data and the second set of volumetric medical image data.

According to yet another aspect, the configuration of the hand of the user comprises at least one of: a fist, one or more fingers extended, or a flat hand.

According to yet another embodiment, a medical image computing system is disclosed comprising: an electronic display; one or more sensors configured to detect a hand of a user; a storage device configured to store electronic software instructions; one or more data stores storing a plurality of medical exams, each medical exam including at least one of volumetric image data or one or more image series, each image series including one or more medical images, each image series associated with an imaging plane; and one or more computer processors in communication with the electronic display, the one or more sensors, the storage device, and the one or more data stores, the one or more computer processors configured to execute the stored software instructions to cause the computing system to: defining a three-dimensional region of physical space in which points within the three-dimensional region are each associated with corresponding anatomical locations within a first medical exam; determine, by the one or more sensors, a position of a finger of a user within the three-dimensional region; determine a first point within the three-dimensional region based on the position of the finger; determine a first anatomical location associated with the first point; select a first medical image of a first image series of the first medical exam that includes the first anatomical location; select a second medical image of a second image series of the first medical exam that includes the first anatomical location; and generate user interface data for rendering an interactive user interface on the electronic display, the interactive user interface including at least the first medical image, the second medical image, a first indication on the first medical image of the first anatomical location, and a second indication on the second medical image of the first anatomical location.

According to another embodiment, a medical image computing system is disclosed comprising: an electronic display; one or more sensors configured to detect a hand of a user; a storage device configured to store electronic software instructions; one or more data stores storing a plurality of medical exams, each medical exam including at least one of volumetric image data or one or more image series, each image series including one or more medical images, each image series associated with an imaging plane; and one or more computer processors in communication with the electronic display, the one or more sensors, the storage device, and the one or more data stores, the one or more computer processors configured to execute the stored software instructions to cause the computing system to: generate user interface data for rendering an interactive user interface on the electronic display, the interactive user interface including at least a first medical image of a first image series and a second medical image of a second image series; detect, by the one or more sensors, a proximity of a hand of a user to the first medical image; in response to determining at least one of a movement of the hand of the user or a change in absolute position of the hand of the user along an axis perpendicular to a plane of the electronic display, updating the user interface data such that the interactive user interface includes a third medical image of the first image series.

In various embodiments, computer-implemented methods are disclosed in which, under control of one or more hardware computing devices configured with specific computer executable instructions, one or more aspects of the above-described embodiments are implemented and/or performed.

In various embodiments, non-transitory computer-readable storage mediums storing software instructions are disclosed, wherein, in response to execution by a computer system having one or more hardware processors, the software instructions configure the computer system to perform operations comprising one or more aspects of the above-described embodiments.

Further, as described herein, various embodiments of the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIGS. 3-6 illustrate example user inputs to the system in which, according to various embodiments, a user's hand is used to manipulate displayed data.

FIGS. 11-12 are an example graphical user interface of the system.

FIGS. 13A-13B and 14A illustrate yet more example user inputs to the system in which, according to various embodiments, a user's hand is used to manipulate displayed data.

FIGS. 15-27 illustrate yet more example user inputs to the system in which, according to various embodiments, a user's hand is used to manipulate displayed data.

FIGS. 30-34 illustrate yet more example user inputs to the system in which, according to various embodiments, a user's hand is used to manipulate displayed data.

DETAILED DESCRIPTION

Figure 1:
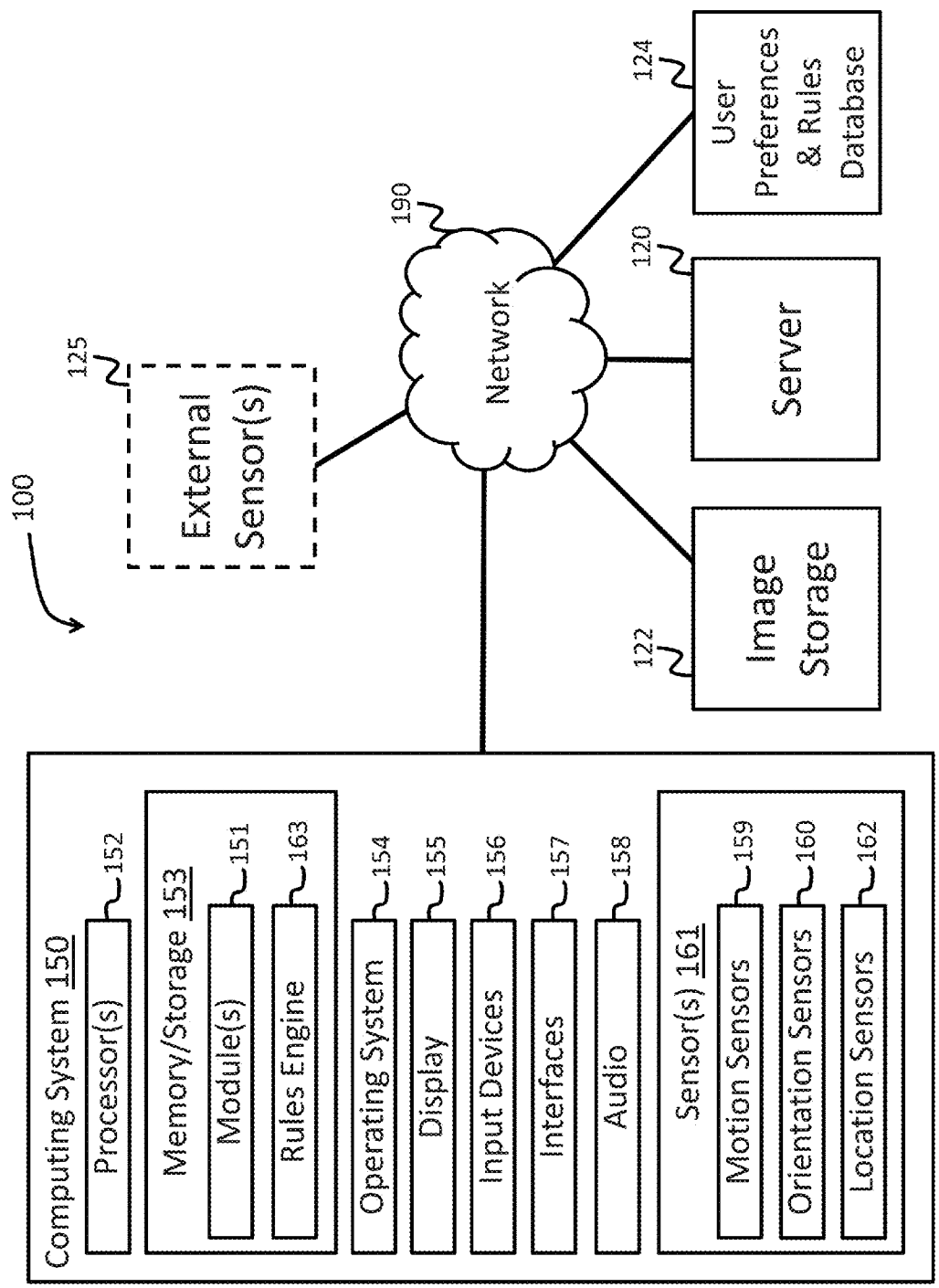
FIG. 1 is a block diagram showing various aspects of a computing system and network environment in which a data navigation system may be implemented, according to various embodiments of the present disclosure.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

I. Overview

As mentioned above, according to various embodiments systems are disclosed that enable a user to more quickly, thoroughly, and efficiently interact with image data including two-dimensional images, three-dimensional image data, and/or series of image data, as compared to previous systems.

As also mentioned above, according to various embodiments a data navigation system is disclosed in which a user may interact with image data (including two-dimensional and three-dimensional), such as medical images and/or rendered volumetric medical imaging data, via hand gestures and other user inputs. In various embodiments described herein, an orientation, configuration, motion and/or position of a user's hand is used to, for example, select series of images within medical imaging exams; navigate through images within an image series; select operations to be performed on images and/or series; provide input to a selected operation to be performed on images and/or series; provide input to 3D rendering software, for example to control the 3D view rendered by 3D volume rendering software; and/or provide input to control the location and/or orientation of an image reconstructed using multiplanar reformation (MPR) or maximum intensity projection (MIP) software; among other features. According to various embodiments, the systems and methods of user interaction with images and 3D imaging information described herein may provide more efficient and intuitive interactions than previous systems. Additionally, according to various embodiments, the systems and methods described herein may not require physical contact with a mouse or other input device, and may be advantageous in scenarios where it is important to maintain sterility, such as operating rooms and intensive care units.

While the use of medical imaging data is described in the example embodiments herein, in various embodiments the systems and methods described may be used for display of, and interaction with, non-medical information, for example, seismic information, weather data, and/or financial data, among others.

Additionally, while the examples herein describe the use of information acquired from a physical object such as a patient, the systems and methods described may be used to display information obtained or generated in other ways, for example, information calculated in a simulation (for example, a financial simulation, and/or a physics simulation, among others). The systems and methods described herein may be used for display of any type of information that can be represented on a digital display.

As described above, various embodiments of the present disclosure provide improvements to various technologies and technological fields, including medical image interaction technology (e.g., Picture Archiving and Communication Systems, Electronic Medical Record systems, and/or the like). Additionally, various embodiments of the present disclosure are inextricably tied to computer technology. In particular, various embodiments rely on detection of user inputs by specialized electronic sensors, calculation of updates to displayed electronic data based on those user inputs, and presentation of the updates via interactive graphical user interfaces. Such features are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic data. Further, one or more of the various interaction described herein may advantageously enable a user to efficiently, accurately, and precisely interact with medical imaging data without touching any physical input device. Such a feature may be particular useful in location where maintaining sterility is important.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

Additionally, in order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

II. The Data Navigation System

FIG. 1 is a block diagram showing various aspects of a computing system 150 and network environment 100 in which the computing system 150 may be implemented, according to various embodiments of the present disclosure. The computing system 150 may be referred to herein as the "data navigation system," the "medical image computing system," simply the "system," and/or the like.

As shown, the network environment 100 may include the computing system 150, a computer network 190, an image storage 122, a server 120, a user preferences and rules database 124, and/or one or more optional external sensors 125. As described below, in various embodiments the computing system 150, the image storage 122, the server 120, the user preferences and rules database 124, and/or the external sensor(s) 125 may be in communication with one another via the network 190. In some embodiments, various of the image storage 122, the server 120, the user preferences and rules database 124, and/or the external sensor(s) 125 may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150.

The computing system 150 may include various components as shown and described in detail below. As described below, the computing system 150 may display images (including, e.g., 3D image data) and/or other data to a user via a display 155. The computing system 150 may include one or more sensors 161 (and/or one or more external sensors 125) that detect a location, configuration, orientation, and/or motion (among other aspects) of a user's hand or other body part. Sensors 161 may take various forms and may utilize, for example, cameras that utilize visible light, cameras that utilize infrared light, ultrasonic sensors, etc. Sensors 161 may be placed in a variety of positions that allow visualization of the body part to be monitored. As described below, in response to user input received by the computing system 150 (including, e.g., detected motion of a user's hand and/or other body part) via various sensors, information displayed (e.g., images and/or 3D data) may be updated. For example, the one or more sensors 161 (and/or one or more external sensors 125) may detect user input provided by capturing data related to the user's hand or other body part, as described above. The captured data may be processed by the one or more sensors 161 (and/or one or more external sensors 125), the server 120, and/or the computing system 150, to generate sensor data indicative of the user input. The sensor data may then be used by the system, as described herein in references to various embodiments, to provide interactive display of various types of information.

Accordingly, the term "user input," as used herein in reference to user interactions with data displayed by the system, is a broad term that refers to any type of input provided by a user that is intended to be received and/or stored by the system, to cause an update to data that is displayed by the system, and/or to cause an update to the way that data is displayed by the system. Non-limiting examples of such user input include hand movements, finger movements, arm movements, movements of any other appendage, body movements, and/or the like. Additionally, the system is not limited to user inputs by appendages of the user, but may also detect and/or receive user inputs via tools and/or other objects manipulated by the user. For example, the user may move an object, such as a surgical instrument, tool, stylus, or wand, to provide inputs. Further, user inputs may include motion, position, rotation, angle, alignment, orientation, configuration (e.g., fist, hand flat, one finger extended, etc.), and/or the like. For example, user inputs may comprise a position, orientation, and/or motion of a hand. User inputs are also referred to herein as "gestures."

Additional components of the computing system 150 may include, for example, one or more processors 152 and memory and/or data storage 153 (including one or more software modules 151 and/or a rules engine 163 (which may itself comprise a software module)). In particular, as described below, the rules engine 163 may execute various rules (for example, one or more rules stored in the user preferences and rules database 124) that may be used to translate various user inputs (e.g., motion of the user's hand) into corresponding movement of displayed images and/or other data. Such rules of the user preferences and rules database 124 may be selected based on, for example, a type of data displayed. Components may also include sensors 161, which may include, for example, motion sensors 159, orientation sensors 160, and/or location sensors 162. The various sensors 161 may include, for example, a camera (for example, video cameras, infrared cameras, and/or the like) or array of cameras capable of detecting (and/or providing data necessary for detecting) a position (including a location and/or orientation) and/or motion of the user's hand (or other gesture from the user). For example, sensors 161 may comprise a commercially available position sensor such as Microsoft's Kinect or Leap Motion's Leap Motion Controller. In various embodiments, one or more, or in some cases all, of the sensors 161 may be located as external sensors 125. In some embodiments, combinations of external sensors 125 and sensors 161 of the computing system 150 may be used for detecting user inputs.

In some embodiments, one or more sensors (for example, external sensors 125) may be attached and/or removably attached to the user, and/or may be located in tools or other objects operated by the user (e.g., a surgical instrument, tool, stylus, or wand, as described above) and such sensors may transmit information to the computing system 150 (through either a wired or wireless connection) such that the inputs of the user may be determined. For example, such sensors on the user may include gyroscopes (that may be used, for example, to detect and measure rotational motion), accelerometers (that may be used, for example, to detect and measure linear motion), compasses, Global Positioning System (GPS) transceivers and devices, near field communication (NFC) technology devices, Radio Frequency Identification (RFID) devices, systems and devices utilizing WiFi, systems and devices utilizing Bluetooth such as iBeacons, and/or the like. In another example, a position transmitter may be used to track the location, position, movement, and/or orientation of the user and/or the user's body parts (e.g., the user's hand). Such a position transmitter may transmit a position and/or motion of, e.g., the user's hand, to one of the external sensors 125. In some embodiments position information from the external sensors 125 may supplement position information from the sensors 161. In other embodiments, a user inputs may be determined based on only information from sensors 161 or based on only information from external sensors 125.

The various sensors and transmitters (e.g., any combination of the sensors described above) may provide input data to the computing system 150 such that inputs from the user may be detected and/or determined. Such input data may be processed by, for example, one or more software modules 151 of the computing system 150 and/or other components of the system, as described below, such that displayed image data and/or other displayed information may be updated.

As further described below, network environment 100 may include a server 120 that provides information that is displayed by computing system 150. Network environment 100 may include image storage 122 (for example, a data store, database, or storage system) that may be configured to store information, such as image data (also referred to herein as image and/or imaging information) (for example, images (e.g., two-dimensional (2D) images), image series, three-dimensional (3D) imaging data, medical imaging exams, and/or the like), that is processed by server 120 and/or computing system 150. Network environment 100 may also include user preferences and rules database 124 which may store user, group, or site preferences and rules that determine the operation of various embodiments, including 3D Hanging Protocols as described herein. Additionally, user preferences and rules database 124 may include various rules that are used by the system to translate user inputs into corresponding movement of displayed images and/or other data, as described below.

In some embodiments, user preferences and rules database 124 may be used to store particular rules and preferences to apply to medical imaging data (or other data types in other embodiments) for particular users. For example, certain rules may be preferred by certain users and/or groups of users. Accordingly, preferences associated with those certain users and/or groups of users may indicate that the certain rules are to be applied such that, for example, movements of data displayed by the system move faster or slower (depending on the user) in response to user inputs, or that certain inputs cause different types of movements of displayed data (depending on the user).

In various embodiments, the functionality provided by image storage 122, server 120, and/or user preferences and rules database 124 may reside within computing system 150. The term "database," as used herein, is a broad term that includes, but is not limited to only, a data structure identified as a database, for example, RDBMS, or SQL, or NoSQL databases. Rather, a "database" may refer to any other data store or data structure such as, for example, comma separated values (CSV) files, eXtendible markup language (XML) files, TeXT (TXT) files, flat files, spreadsheet files, and/or any other widely used or proprietary format.

Figure 2B:
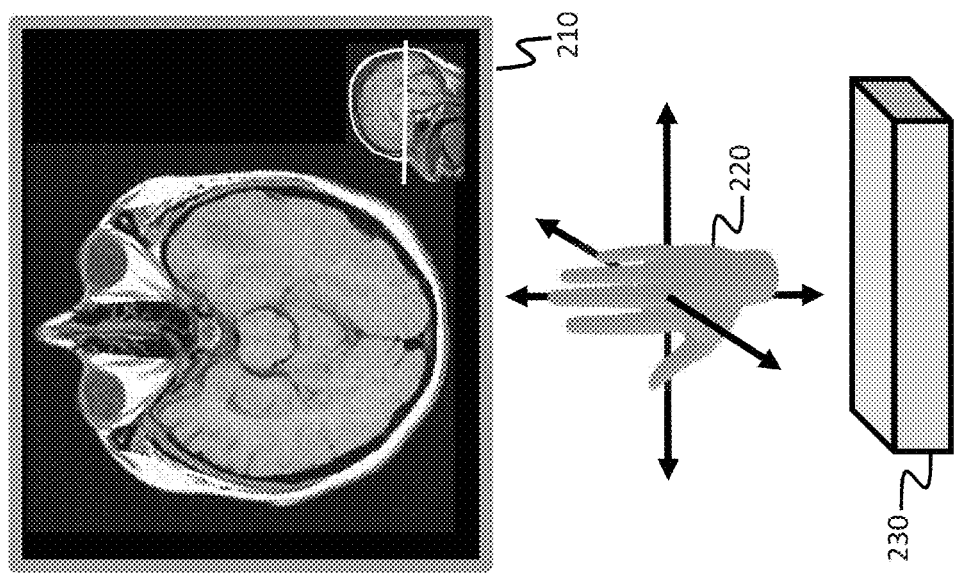
FIG. 2B shows an example embodiment of the data navigation system.
Figure 2A:
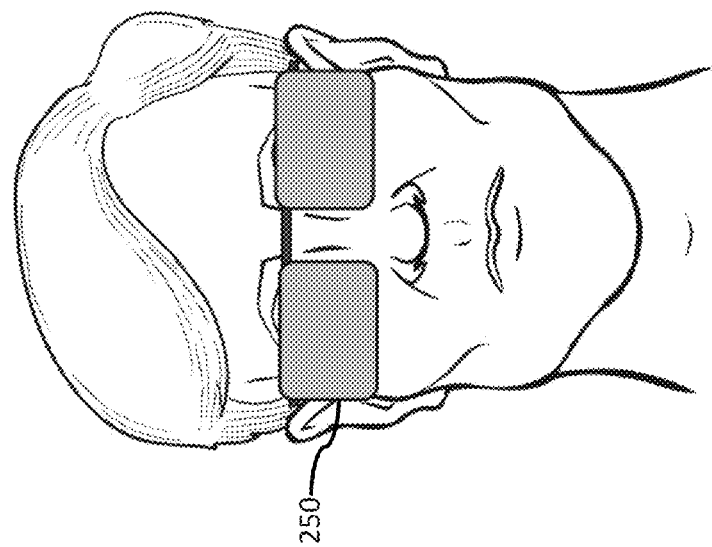
FIG. 2A is a diagram of example user interactions with an embodiment of the data navigation system.

FIG. 2A is a diagram of example user interactions with an embodiment of the data navigation system. Specifically, the embodiment of the system shown in FIG. 2A includes a computer display device 210 (such as the display 155 described above) and a sensor 230. User inputs to the system are illustrated by the hand 220 that may move around in three-dimensional space (as illustrated by the three axes). As described above, the user may provide inputs by position of the hand, motion of the hand, orientation of the hand, configuration of the hand (e.g., pointing one or more fingers), and/or the like. The hand inputs are detected by the sensor 230, which may comprise one of the sensors 161 described above and below in reference to FIG. 1. Information indicative of the user inputs detected by the sensor 230 are communicated to the computing system 150, for example, which computing system then uses the user input information to determine what and how data is to be displayed on computer display device 210.

FIG. 2B shows an example embodiment of the data navigation system utilizing a head mounted display 250. In various embodiments, computing system 150 of the system may display information on any type of computer display, such as a computer monitor 210 in FIG. 2A or a head mounted display, such as head mounted display 250 of FIG. 2B.

In various embodiments, sensor(s) 161 may be placed in any suitable location (and/or locations) for detection of user inputs. For example, the sensor may be placed above or below a display device (e.g., as shown in FIG. 2A where the sensor 230 is shown below the display device 210). In some embodiments, the sensors may be mounted to the user. For example, a sensor may be mounted to the head mounted display 250 illustrated in FIG. 2B. In another example, a sensor may be mounted to an appendage of a user, integrated into a glove worn by the user, and/or the like. In various embodiments, combinations of different types of sensors may be used individually and/or simultaneously by the system to determine user inputs.

Figure 2C:
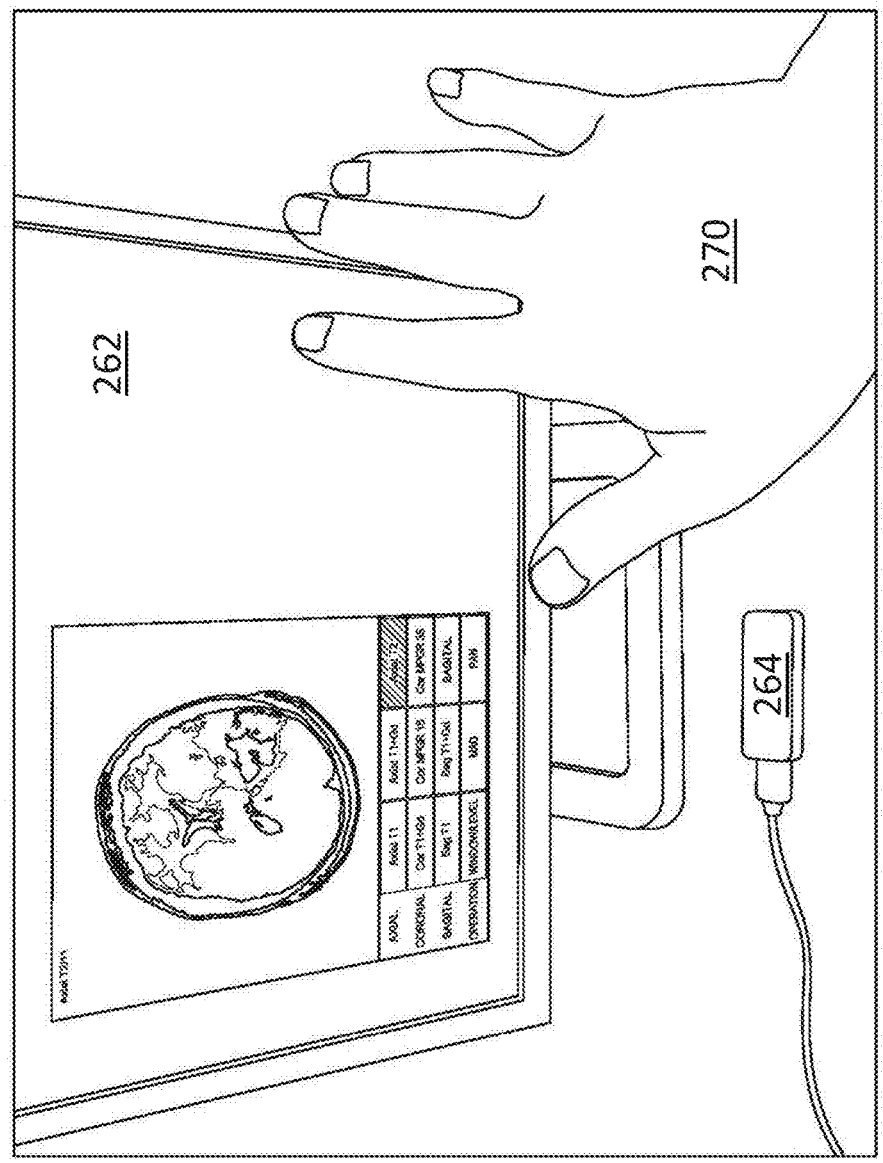
FIG. 2C shows an example of a user interacting with an embodiment of the data navigation system.

FIG. 2C shows an example of a user interacting with an embodiment of the data navigation system. The user provides input by hand gestures 270. The user inputs are detected by sensor 264. Information indicative of the user inputs are communicated from the sensor 264 to a computing device (e.g., computing system 150), where they are processed and used to update the data displayed on the computer display 262.

III. Example User Inputs to Interact with Medical Exams

FIGS. 3-6 illustrate example user inputs to the system in which, according to various embodiments, a user's hand is used to manipulate displayed data. As described above and below, the user's hand as the tool to provide inputs to the system is illustrative. Other tools may be used to provide user inputs, for example other appendages, whole body movement, wands, and/or the like. While not specifically illustrated in many of the figures below, the described user inputs may be detected by one or more sensors of the system, and may be processed and translated into updates of displayed data, as described above and below.

Additionally, while FIGS. 3-6 illustrate user inputs to interact with medical images and/or medical image series of a medical imaging exam (also referred to herein a "medical exam"), the example user inputs may be used to interact with other types of data (as described above).

Medical imaging exams may consist of one or more series of images, with each series consisting of one or more images. For many imaging exams, such as magnetic resonance imaging (MRI) and computed tomography (CT), images within a series are typically acquired in a same orientation or imaging plane but vary in location, e.g., a series of parallel images acquired every 3 mm. Typically series are acquired in standard anatomical imaging planes. For example, a brain MRI exam might consist of the following image series:
Sagittal T1
Axial T1
Axial FLAIR
Axial T2
Coronal Multiplanar gradient recalled acquisition ("MPGR")
Coronal T1
Sagittal T1+Gd (with contrast)
Axial T1+Gd (with contrast)
Coronal T1+Gd (with contrast)

Thus, a medical exam may include multiple 2D series, where some or all of the series are acquired in different imaging planes, such as axial, coronal, and sagittal. As described below, various different user inputs may be used to interact with individual images, multiple images, series of images of the medical exam, and/or the like.

FIG. 3 illustrates an embodiment of the system in which an orientation of the user's hand is used to select different image series to be displayed from a medical imaging exam. For example, the user may change their hand orientation to select a corresponding series or a particular imaging plane. As described, the plane of the hand may correspond to the selected imaging plane of the medical exam.

In view 310*a*, the user has positioned his hand in a horizontal orientation 330*a* and the system responds by displaying an axial series.

As illustrated in view 310*b*, when the user positions his hand in a vertical orientation 330*b*, palm facing away, a coronal series is displayed.

As illustrated in view 310*c*, when the user positions his hand in vertical orientation 330*c*, palm facing to the side, a sagittal series is displayed.

In some embodiments, images are chosen for display from a series of images or pre-calculated 2D images. In other embodiments, displayed images (such as the images displaying in FIG. 3) are calculated, for example, from a volumetric (e.g., 3D) data sets (e.g., volumetric MRI, CT, or ultrasound) using Multiplanar Reconstruction (MPR), Maximum Intensity Projection (MIP), or another technique. In various embodiments, calculation of images from volumetric data may be done preemptively (e.g., the data may be processed before a user interacts with the system to generated series of 2D images) and/or in real-time or substantially real-time (e.g., in either real-time or substantially real-time the data may be processed to generate 2D images, and the 2D images may be displayed, in response to user inputs).

For example, the system may monitor the user's hand position and dynamically calculate and display 2D images from the 3D volumetric data such that a plane of the 2D image is determined by the orientation of the user's hand. For example, as in the three views shown in FIG. 3, axial, coronal, and sagittal reformations may be automatically displayed in response to the user positioning his hand into various orientations, as described above.

In addition, rotation of the user's hand into other, arbitrary, oblique orientations could result in calculation and display of reformations in corresponding orientations. As will be discussed in reference to other figures, the user's hand position may be used to select the location of the reconstructed plane.

In another embodiment where an exam includes projection images (e.g., one or more series of projection images, and/or a single series with multiple different types of projection images), hand orientation may be used to select the projection to display (e.g., to select a particular series of projection images from the exam and/or to select particular images from a series of various projection images). For example, a chest x-ray might consist of AP (frontal) and lateral views, and a vertical hand position 330*b* could be used to select the frontal projection and a laterally oriented hand position 330*c* could be used to select a lateral view. In an embodiment, when multiple imaging exams on a patient are available, a change in hand configuration could be used to select the exam to display, while hand orientation is simultaneously used to select the projection to display. For example, in response to the system detecting that the user is holding up one, two, or three fingers, the system may display a first, second or third exam, while the projection displayed is simultaneously controlled by hand orientation.

FIG. 4 illustrates an embodiment in which users may select different images within a series or different locations of planes to be reconstructed from 3D volumetric imaging, for example using MPR.

As illustrated in the example of FIG. 4, in view 410*a* the user's hand is in a horizontal orientation 430*a* and the system therefore displays an axial image 420*a*. This could be an image from an axial series, e.g., an axial T1 series of the brain, or an axial reformation reconstructed from a volumetric data set using, for example, MPR or MIP.

Compared to view 410*a*, views 410*b* and 410*c* illustrate progressively more superior positions of the hand (e.g., as the hand moves from position 430*a* to 430*b*, and then to 430*c*), and the system automatically displays images at locations that are at progressively superior positions within displayed structure (e.g., images 420*b* and 420*c*), in this example a brain imaged using MRI.

In the case of a 2D series, this could be accomplished by displaying images within a same image series that are at progressively superior positions. In the case of 2D reconstruction from volumetric data, the images could be reconstructed at progressively superior planes from the volumetric data.

In one embodiment, superior or inferior motion of the hand could be used to increment or decrement the position of the image. For example, motion of the hand in a superior direction may cause corresponding images further into the series to be displayed, while motion of the hand in an inferior direction may cause corresponding images toward the start of the series to be displayed.

In another embodiment, there may be a spatial mapping of hand position to the anatomical region imaged so that an absolute position of the hand relative to some fixed position in space (for example, in relation to a position above a sensor) is used to select the location for the image is displayed. For example, the system may determine a virtual absolute position in space of the image (and/or image series). The virtual absolute position of the image/image series may be based on, for example, a location of one or more sensors, and/or some other reference. Thereafter, an absolute position of the user's hand in relation to the virtual absolute position of the image/image series in space may be used to determine what particular image data is to be displayed.

Figure 5:
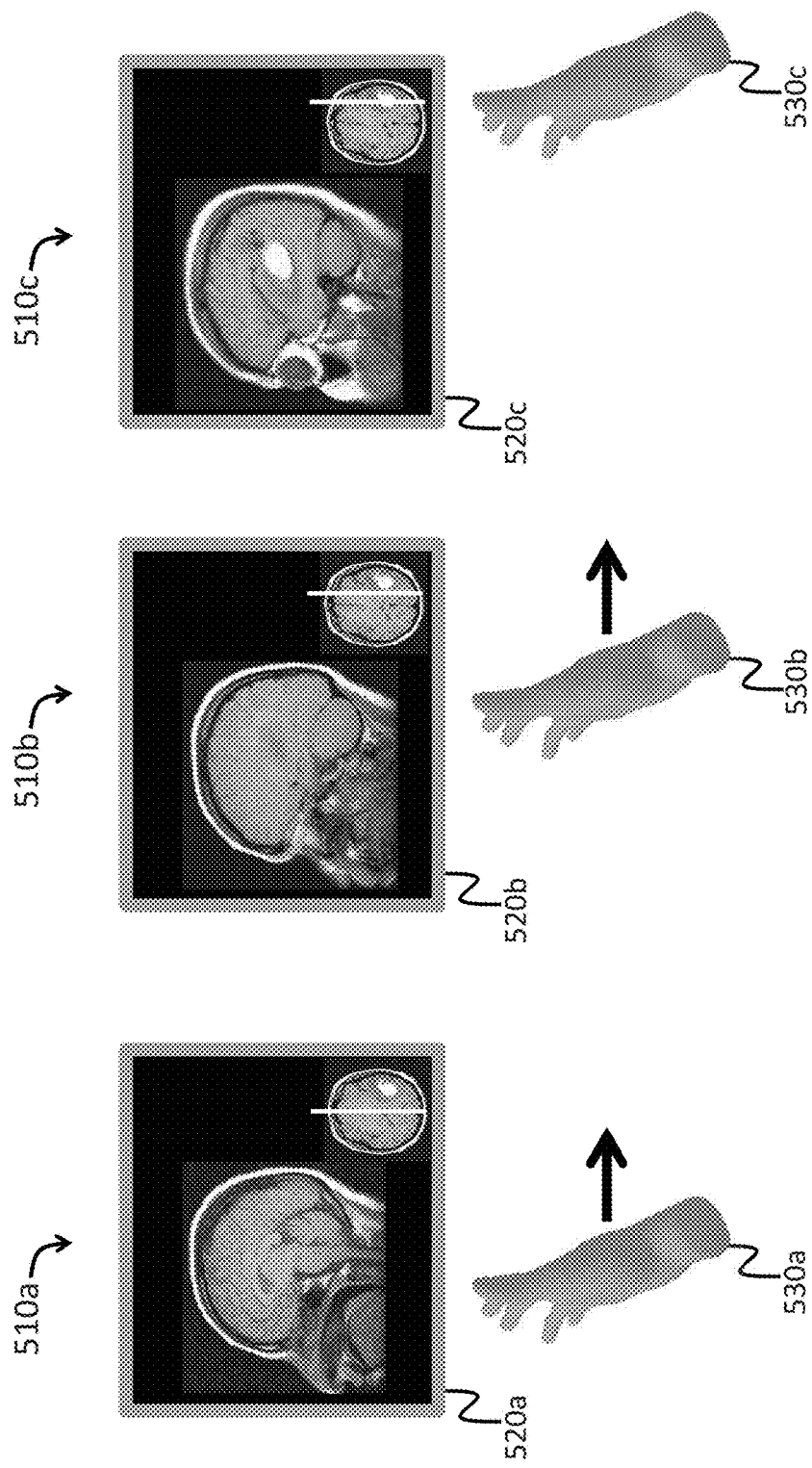

FIG. 5 illustrates an embodiment similar to FIG. 4, but in FIG. 5 the user's hand is in a different orientation. In this example the lateral orientation of the hand (as illustrated by hand 530*a*) is used to select the sagittal plane. The position of the user's hand is used to navigate through images within a series (e.g., a series corresponding to the sagittal plane) or select positions for 2D reconstruction of sagittal images from volumetric data. For example, as the hand moves from position 530*a* (shown in view 510*a*) to position 530*b* (shown in view 510*b*) and then to position 530*c* (shown in view 510*c*), corresponding images 520*a*, 520*b*, and 520*c* of the image series are displayed by the system.

Accordingly, in this and other embodiments of the system, different types of user inputs may be combined and/or provided to the system simultaneously. For example, the user may position his hand into an orientation that selects display of images in a particular plane (e.g., the sagittal plane) or from a particular series in an medical exam, and further may move his hand (e.g., along an axis perpendicular to his hand and/or along any other arbitrary axis or general direction) to view different images of the selected plane/series.

FIGS. 4 and 5 illustrate examples of hand positions corresponding to axial and sagittal orientations and how hand location or movement can be used to navigate to images at various positions within the selected plane. While not shown, similar user inputs (e.g., other hand orientations and/or movements) may be used to select other images, image series, and/or medical exams. For example, hand orientation 330*b* of FIG. 3 may be used to select, e.g., a coronal plane or reconstruction of 2D images in a coronal plane from 3D volumetric image data. In this example, positioning of the hand along an axis perpendicular to the hand, front to back, may result in display of images at various locations along an axis perpendicular to the coronal plane.

Figure 6:
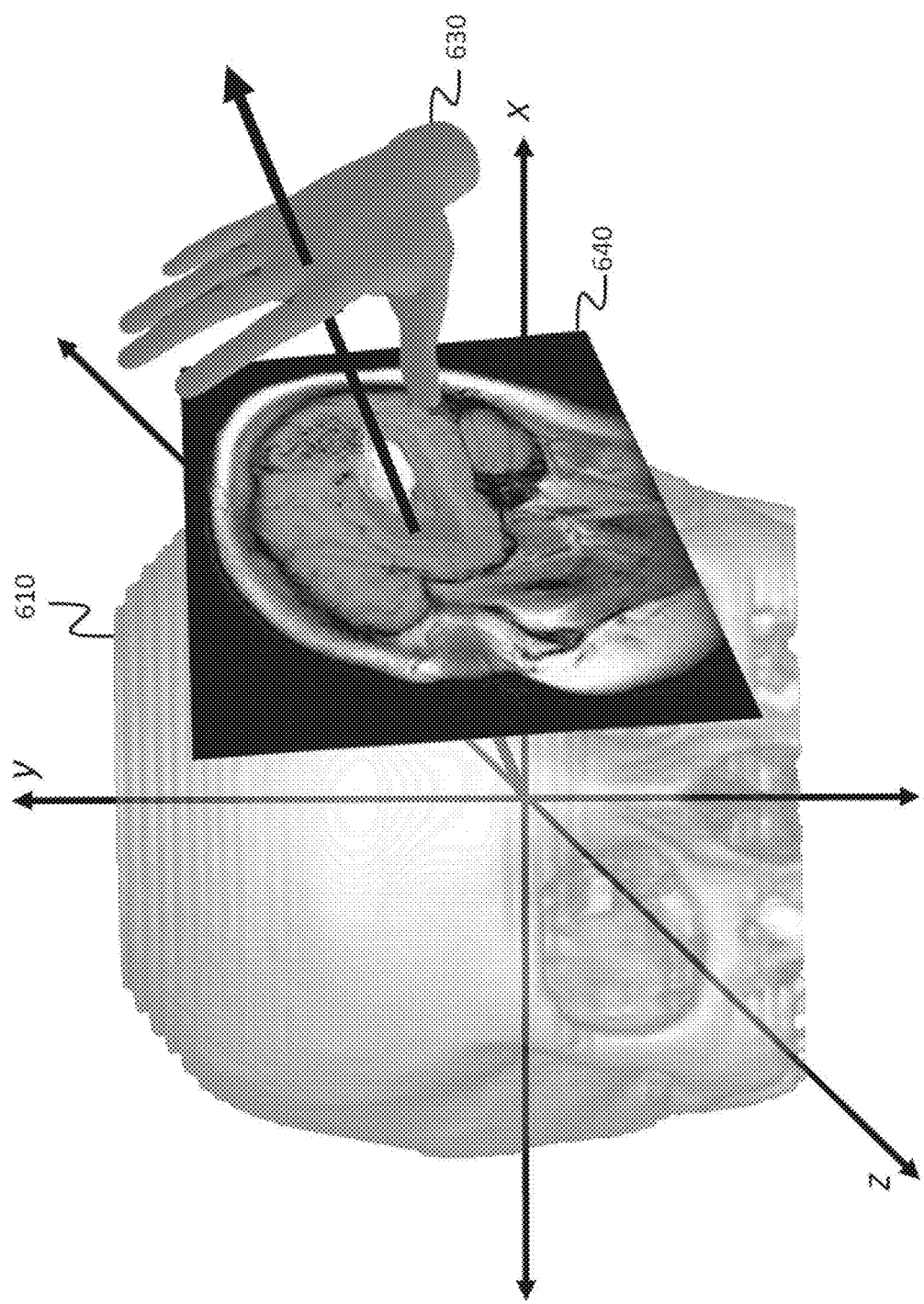

While prior figures illustrated examples of selection of images in sagittal, coronal, and axial orientations, any arbitrary hand orientation may be used to select images at arbitrary orientations. For example, FIG. 6 illustrates a volumetric dataset 610 that may include, for example, image data for a region of a patient's body imaged using MRI, CT, ultrasound, or nuclear medicine imaging. As described above, the system may calculate a virtual absolute position of the volumetric dataset 610 with reference to, for example, a sensor and/or a display. Then, user input, e.g., hand 630, may be positioned in any arbitrary orientation with reference to the virtual absolute position of the volumetric dataset 610 to control the plane of a reconstructed image 640 that is displayed to the user on a display device. For clarity of illustration, hand 630 and reconstructed image 640 are shown at an offset. In some embodiments, the orientation of the hand relative to a different reference point (e.g., an initial position and orientation of the hand) may be used for determining an image plane.

In various embodiments, other types of user inputs than those described above, or combinations of user inputs, may be used to interact with image data (and/or other types of data). For example, hand position may be used to select an image series from a medical exam, while hand orientation may be used to select a particular image and/or anatomical location in the series. In another example, incremental movement of the hand (rather than orientation of the hand, as described in reference to FIG. 6 above) may be used to incrementally move the location of the plane to be reconstructed.

IV. Example Method, User Preferences, and Rules

Figure 7:
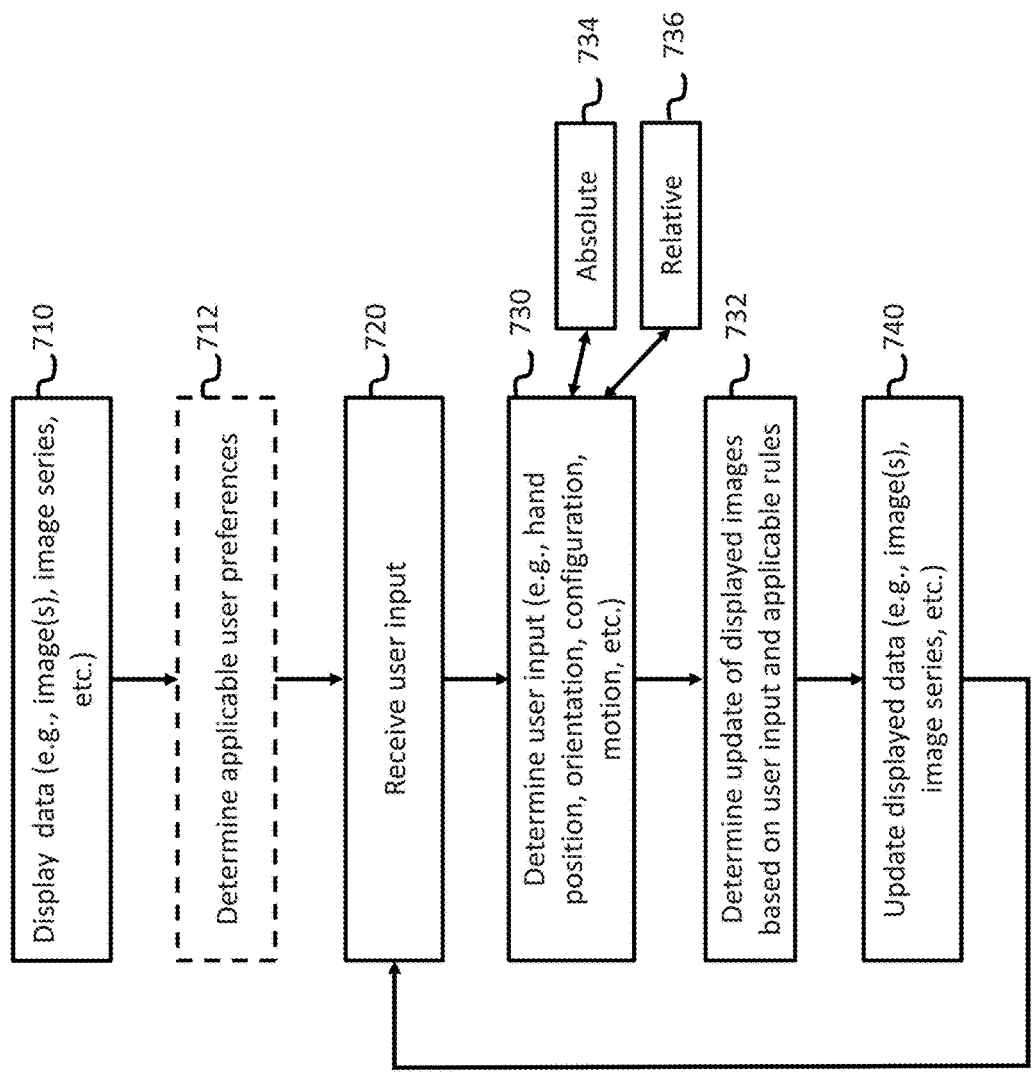
FIG. 7A is a flow chart illustrating an example method of user interaction with the system.
FIG. 7B is a table illustrating example rules of the system.

FIG. 7A is a flow chart illustrating an example method of user interaction with the system. Specifically, FIG. 7A illustrates a method of the system, according to an embodiment, in which user inputs (such as the example user inputs described above and below) are detected and converted into updated displays of data. The method of FIG. 7A may be performed by the computing system 150 and/or a combination of the computing system 150, the server 120, and/or any other suitable computing device and/or system. Depending on the implementation, the system may perform methods having more or fewer blocks than are shown, and/or the blocks may occur in a different order and/or in parallel in order to accomplish the methods and/or processes of the system.

At block 710, the system displays data (e.g., an image) to the user. As described above, the image may be displayed on a display device of the system, such as display 155. Additionally, as described above, the displayed image may be an image selected from an image series of a medical exam, and/or an image reconstructed from a volumetric data set.

At optional block 712, the system may determine applicable user preferences. Such user preferences may be stored in, e.g., the user preferences and rules database 124. User preferences may be selected based on an identity of the user. For example, a set of user preferences may be specific to a given user. Alternatively, user preferences may be selected based on a characteristic associated with the user. For example, the user may be a member of a group (e.g., a type of doctor, etc.), and the system may include user preferences specific to the group. In another example, the user may be associated with a particular site (e.g., a hospital, etc.), and the system may include user preferences specific to the site. As described above, in various embodiments, user preferences may be associated with rules in the user preferences and rules database 124. For example, the rules may be executed by the system to translate user inputs to updates of displayed data (e.g., images). In some embodiments, the default set of rules may apply to all user interactions, and/or when there are no user preferences associated with the user.

At block 720, the system receives input from the user. Examples of user input are described above and below. The user input may be detected by one or more sensors of the system (e.g., sensors 161 and/or external sensors 125). The user input detected by the sensors may be communicated to, for example, computing system 150.

At block 730, the specific input from the user is determined by the system. For example, the system may determine an orientation, position, configuration, and/or motion of the user's hand. Additionally, the system may determine, for example, an amount of motion and/or a speed of motion. The determination of block 730 may be performed by the computing system 150 and sensors. As described above, and as indicated by block 734, in some embodiments user input is determined relative to an absolute reference point (for example, movement of a hand through a virtual absolute position of a series of images and/or a volumetric dataset). As further described above, and as indicated by block 736, in other embodiments user input is determined relative to a relative reference point (for example, a relative movement of a hand from an initial starting point).

At block 732, the determined user input is translated into a corresponding update to the displayed image. In an embodiment, the translation is accomplished by execution of one or more rules of the user preferences and rules database 124 by the rules engine 163. For example, as described above particular motions of a user's hand may cause various images of an image series to be displayed. In another example, an orientation of the user's hand may cause various image series of a medical exam to be displayed.

At block 740, the displayed data (e.g., images) are updated according to the determination of block 732 described above.

FIG. 7B is a table illustrating example rules of the system that may be stored in the user preferences and rules database 124. Example rules associated with different sets of users' preferences are shown. For example, rules associated with an individual user ("User 1"), a group of users ("Group 1"), and a site ("Site 1") are shown. As shown, the rules may vary for different users. For example, for User 1, the rules indicate that hand orientation user input is to be translated into a selection of a series of images, while hand movement along an axis normal to the plane of the user's hand is used to select and image in the series.

As described above, some rules may be based on a type of data displayed. For example, a certain set of rules may apply to medical image data, while a different set of rules may apply to financial data. In another example, rules may vary according to a type of image series displayed. This is illustrated in FIG. 7B in reference to Group 1 rules. As shown, if an image series is a Sagittal series, then hand movement along an axis normal to the plane of the hand is used to select an image in the series. However, if an image series is an Axial series, then hand movement along an axis parallel to the plane of the hand is used to select an image in the series. Additionally, the rules may indicate when absolute inputs are to be used versus relative inputs. As shown in reference to the rules of Site 1, an absolute position of the hand in space is used to determine an image in a series to display. In other examples, rules may vary based on modality (e.g., CT vs. MRI), based on the anatomic region imaged (e.g., brain vs. abdomen), or based on patient information associated with the exam (such as clinical history or the clinical indication for the exam).

The rules described above are illustrative. Various other rules may indicate other types of inputs and the corresponding updates to displayed data. For example, various example user inputs are described herein in reference to the various figures, many of which are not included in the rules of table of FIG. 7B, but may be included in the rules of the system in various implementations. In some embodiments, speed of movement of displayed data relative to user inputs may be specified in the rules also.

V. Example User Inputs to Interact with Multiple Image Series

Figure 8:
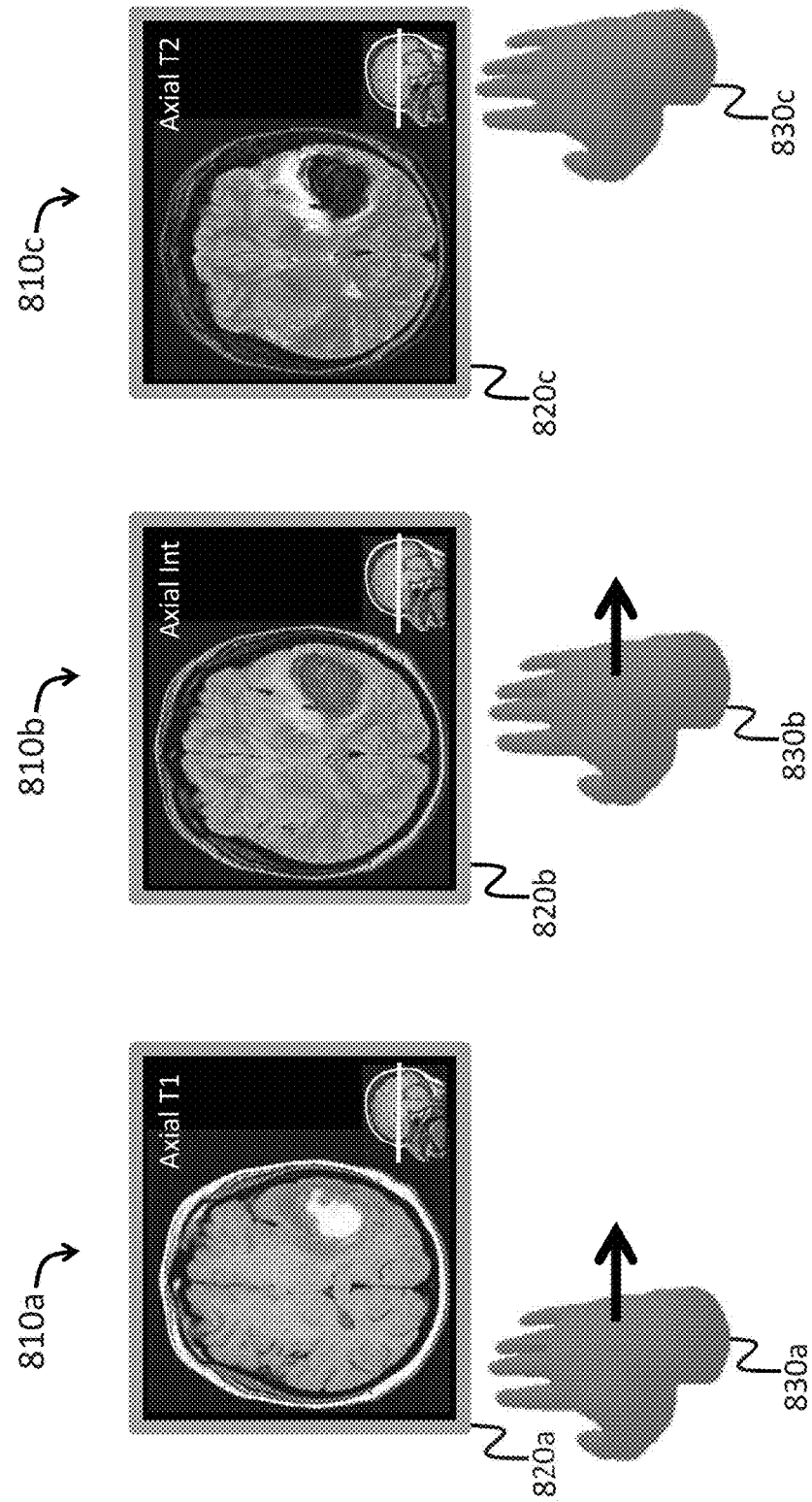
FIGS. 8-10 illustrate additional example user inputs and graphical user interfaces to the system in which, according to various embodiments, a user's hand is used to manipulate displayed data.
Figure 9:
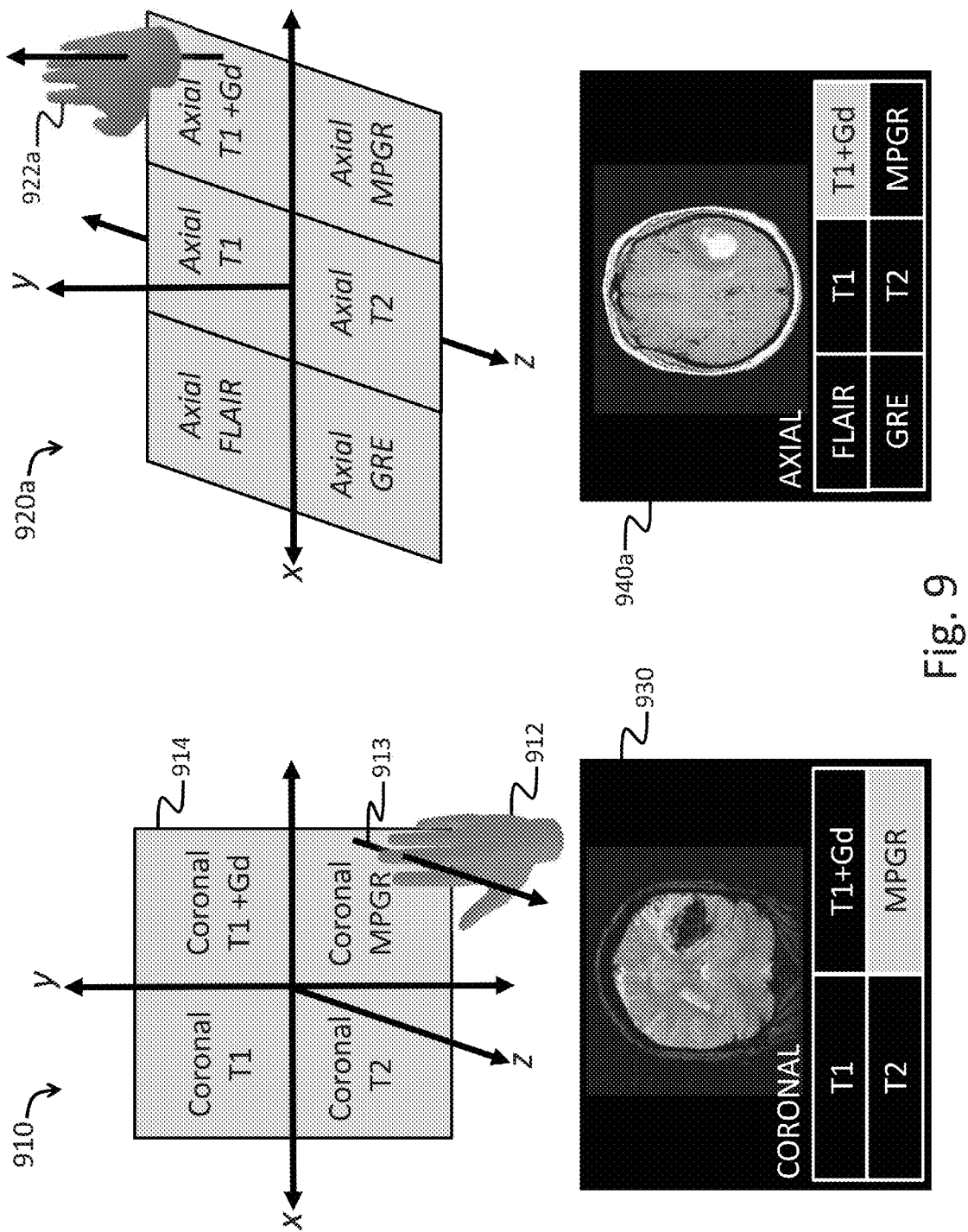
Figure 10:
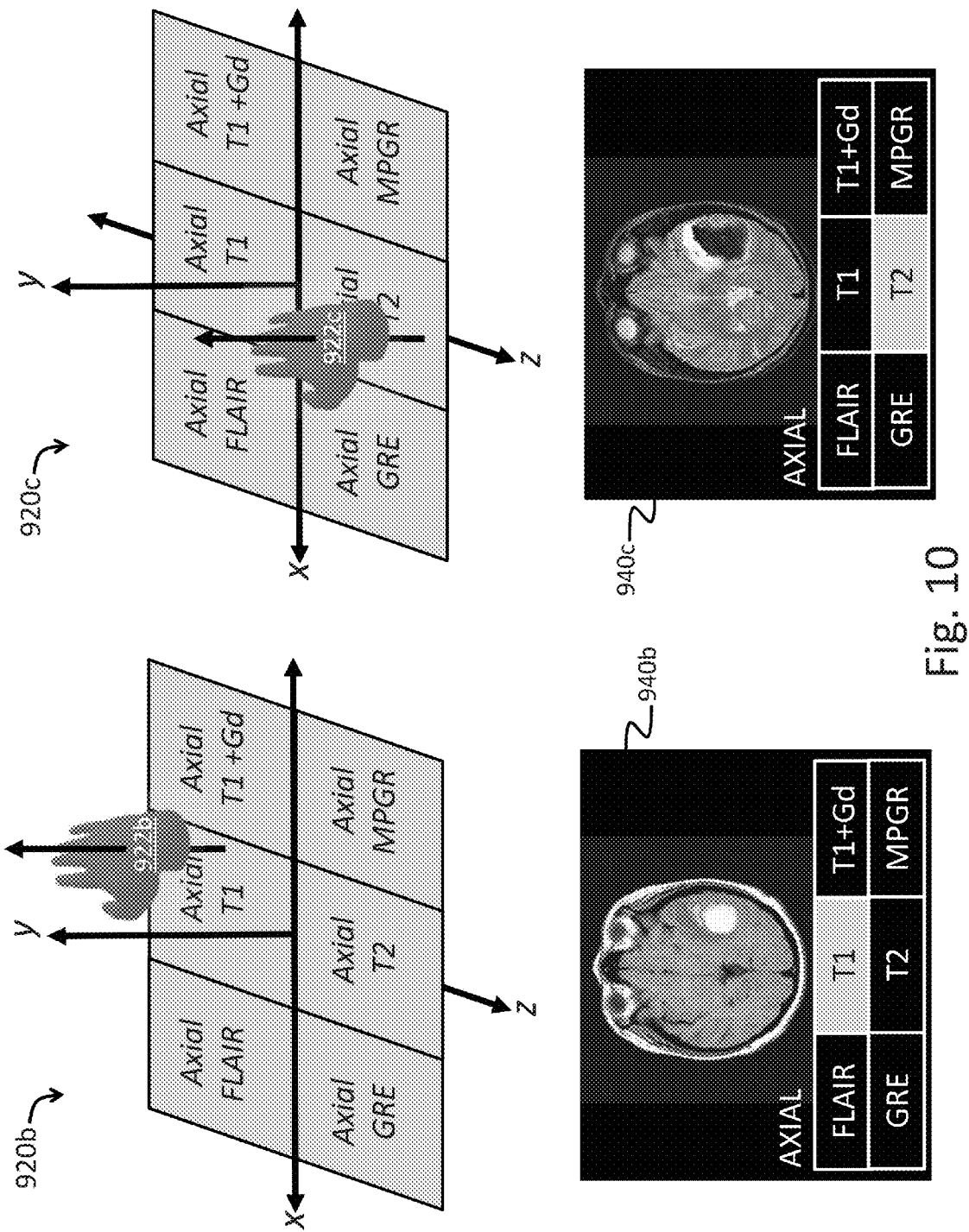

FIGS. 8-10 illustrate additional example user inputs to the system in which, according to various embodiments, a user's hand is used to manipulate displayed data. As with the example user inputs described above in reference to FIGS. 3-6, and with all example user inputs described herein, the user's hand as the tool to provide inputs to the system is illustrative. Other tools may be used to provide user inputs, for example other appendages, whole body movement, wands, and/or the like. While not specifically illustrated in many of the figures below, the described user inputs may be detected by one or more sensors of the system, and may be processed and translated into updates of displayed data, as described above and below. Further, while the various figures illustrate user inputs to interact with medical images and/or medical image series of a medical exam, the example user inputs may be used to interact with other types of data (as described above).

In medical imaging exams, more than one series of images may be acquired in a particular plane. In addition, more than one volumetric image set may be acquired so that images in a particular plane may be reconstructed from more than one 3D volume. Therefore, when viewing medical exams, there is a need to for the user to have a method to choose from among these various datasets.

FIG. 8 illustrates an embodiment of the system in which the user's hand is used to select among different imaging planes, different series of a given plane, and different images of a given series. In the embodiment illustrated in FIG. 8 via positions 810*a*, 810*b*, and 810*c*:

- Hand orientation is used to select the plane of the image to display. In the example shown, the hand is in a horizontal orientation so the group of axial series is chosen.
- Hand position or movement in the plane of hand orientation is used to select among series in the chosen plane (or volumetric data from which the images are generated, e.g., using MPR or MIP). In one embodiment, movement in the plane of hand orientation changes series and the image shown from a second series is in the same anatomical location as the image shown in the first series. In the example illustrated, the hand is moved from location 830*a* to 830*b* to 830*c*, causing display of a T1 (image 820*a*), intermediate (image 820*b*), and T2 weighted axial (image 820*b*) brain MRI images at the same anatomical location.
- Hand movement perpendicular to hand orientation is used to select an anatomical location within the selected series.

There is also a need for simple and intuitive methods for a user to select among the various series within a medical imaging exam.

In an embodiment referred to herein as 3D Hanging Protocols, the user can select a series for display on a display device or in a display frame on a display device by using hand position or motion. As described in other embodiments, the user may use hand orientation to select a group of series within a medical imaging exam.

For example, referring now to FIGS. 9-10, orienting the hand in a roughly coronal plane (as illustrated by hand 912) may select the group of coronal series within a medical imaging exam, as illustrated in the example of view 910. With that hand orientation, the user may move his hand in the same plane or a parallel plane to select a specific series from among the chosen group. In the example of view 910, the user may translate his hand up-down and left-right to choose among the listed series. Moving the hand along the axis perpendicular (or normal) to the plane of hand orientation (as illustrated by arrow 913) may be used to select specific images within the chosen series, as discussed in other embodiments.

In the example of view 910, the upper left position selects the coronal T1 series, for example within a brain MRI. The upper right position 914 selects the Coronal T1+Gd series, etc. The specific series that correspond to various positions may vary by exam type.

The particular series selected by different hand positions and exam types, the 3D Hanging Protocol, may be stored as user, group or site preferences, for example in user preferences and rules database 124 illustrated in FIG. 1.

Therefore, users may designate and store their own 3D Hanging Protocol for the various types of imaging exams they read. While one user might use the arrangement shown in view 910, another user might designate a 3D Hanging Protocol were the upper left position corresponds, for example, to the Coronal FLAIR sequence, rather than the Coronal T1 sequence. The 3D handing protocol may be automatically displayed to the user in a graphical user interface along with the selected image. For example, display 930 illustrates an example graphical user interface in which the four series available in the example 3D hanging protocol illustrated in view 910 are displayed to the user, including the relative hand positions used to select the four series. In the example shown, the currently selected series (MPGR) is highlighted so the user can easily identify the selected series from among those that are available for the selected plane (CORONAL).

A 3D Hanging Protocol may include one or more planes. The components of an example 3D Hanging Protocol related to horizontal hand position (axial series) is illustrated in views 920a, 920b, and 920c of FIGS. 9-10, along with associated respective example graphical user interfaces 940a, 940b, and 940c, which behave similarly to the example graphical user interface ("GUI") 930.

In view 920a, the user has positioned his hand in a horizontal or roughly horizontal orientation (as illustrated by hand 922a), selecting the group of axial series within the example brain MRI exam illustrated. By positioning his hand in the posterior-right position, he has selected the Axial T1+Gd series.

In views 920b and 920c of FIG. 10, the user has selected other series, the Axial T1 (as illustrated by hand position 922b) and Axial T2 (as illustrated by hand position 922c) series in the examples shown. The arrangement of the various series might differ in the 3D Hanging Protocol of other users.

In addition to the axial and coronal groups shown, a 3D Hanging Protocol may include a mapping of spatial position for series in the sagittal plane as well as in arbitrary planes.

The number of series in each plane may vary. In the example of view 910, there are 4 coronal series, while in the example of views 920a, 920b, and 920c, there are 6 axial series.

Accordingly, as described, the user may simultaneously provide three distinct types of inputs to the system, which the system then translates into updates to displayed data. For example, in an embodiment:
1. Hand orientation selects imaging plane.
2. Hand position within the plane parallel of the plane of the hand selects image series within the selected imaging plane.
3. Hand position along an axis perpendicular of the plane of the hand selects images within the selected image series.

Further, as mentioned above, and as further described below, hand configuration (and/or other types of inputs) may also be used as an input to the system (in addition to and/or in combination with other types of inputs described above). Thus, extending the example described above, the user may simultaneously provide four (or more) distinct types of inputs to the system, which the system then translates into updates to displayed data. For example, in an embodiment:
1. Hand orientation selects imaging plane.
2. Hand position within the plane parallel of the plane of the hand selects image series within the selected imaging plane.
3. Hand position along an axis perpendicular of the plane of the hand selects images within the selected image series.
4. Hand configuration selects a medical imaging exam.

As described below, hand configuration may include, e.g., opening of the hand, extension of one or more fingers of the hand, closing of the hand, and/or the like. For example the user might be viewing a brain MRI on a patient and may change hand configuration to view a matching anatomic image from a prior brain MRI (e.g., having a same series orientation, series type, and anatomic location as a view before the change to the prior brain MRI). For example, the user the user may elongate 1, 2 or 3 fingers to cause display of 1st, 2nd and 3rd exams, respectively.

VI. Example User Inputs to Interact with a 3D Hanging Protocol and Select Operations FIGS. 11-12 and 13A-13B and 14A illustrate additional example graphical user interfaces and user inputs to the system in which, according to various embodiments, a user's hand is used to manipulate displayed data. As with the example user inputs described above in reference to FIGS. 3-6, and with all example user inputs described herein, the user's hand as the tool to provide inputs to the system is illustrative. Other tools may be used to provide user inputs, for example other appendages, whole body movement, wands, and/or the like. While not specifically illustrated in many of the figures below, the described user inputs may be detected by one or more sensors of the system, and may be processed and translated into updates of displayed data, as described above and below. Further, while the various figures illustrate user inputs to interact with medical images and/or medical image series of a medical exam, the example user inputs may be used to interact with other types of data (as described above).

Figure 11:
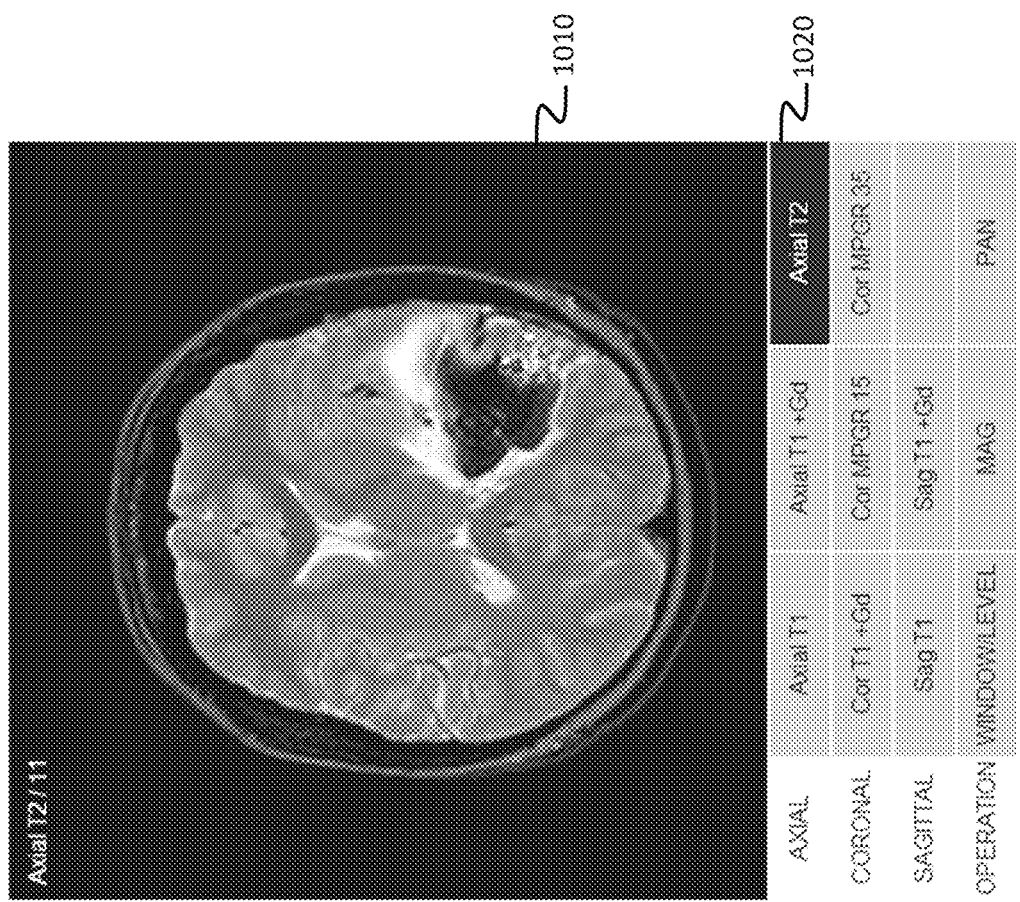

FIG. 11 illustrates a graphical user interface associated with a 3D Hanging Protocol illustrating display of selected image 1010. Inferior to the image are a series of labeled blocks showing available series that may be selected by the user for display. In the example shown, the Axial T2 series is selected, and the associated series label 1020 is shown with a different appearance than unselected series. In this example, the label for the selected series is displayed with white letters on a black background, in contrast to unselected series which are displayed with black text on a gray background.

In the example shown in FIG. 11, the axial and coronal series each have three available series, and the sagittal series has two available series. The arrangement of the series labels on the display may correlate with the spatial positions that user would place his hand to select that series.

For example, to select the Axial T2 series, the user may place his hand in an axial orientation to select the group of axial series. He may then move his hand to the right until the Axial T2 series in selected.

To select the "Cor T1+Gd" series, the user may place his hand in a vertical (coronal) orientation and move his hand to the left.

FIG. 12 is an example user interface similar to FIG. 11. In the example shown, a series of operations from which the user can choose is displayed below the list of series names. In the example shown, operation names are displayed on the last row 1240, including "Window/Level" 1242 (which is the currently selected operation, as indicated by the different appearance), "Mag" (an abbreviation for magnify), and Pan. These operations, and selection of the operations, are further described below with reference to FIGS. 13A and 13B.

In one embodiment a change in hand configuration is used to select the group of available operations and hand position is used to select a particular operation from within the group of operations. For example, in embodiments described above, an open hand was illustrated to choose from among the available groups of series, choose a particular series from the selected group, and to choose a particular image from the selected series. In addition to the inputs that have been described above, hand configuration may also be used to provide user inputs. For example, different hand configurations, for example one in which the hand is pointing, as in view 1302 (of FIG. 13A), may be used to indicate a different operation mode to the computing system.

Figure 13A:
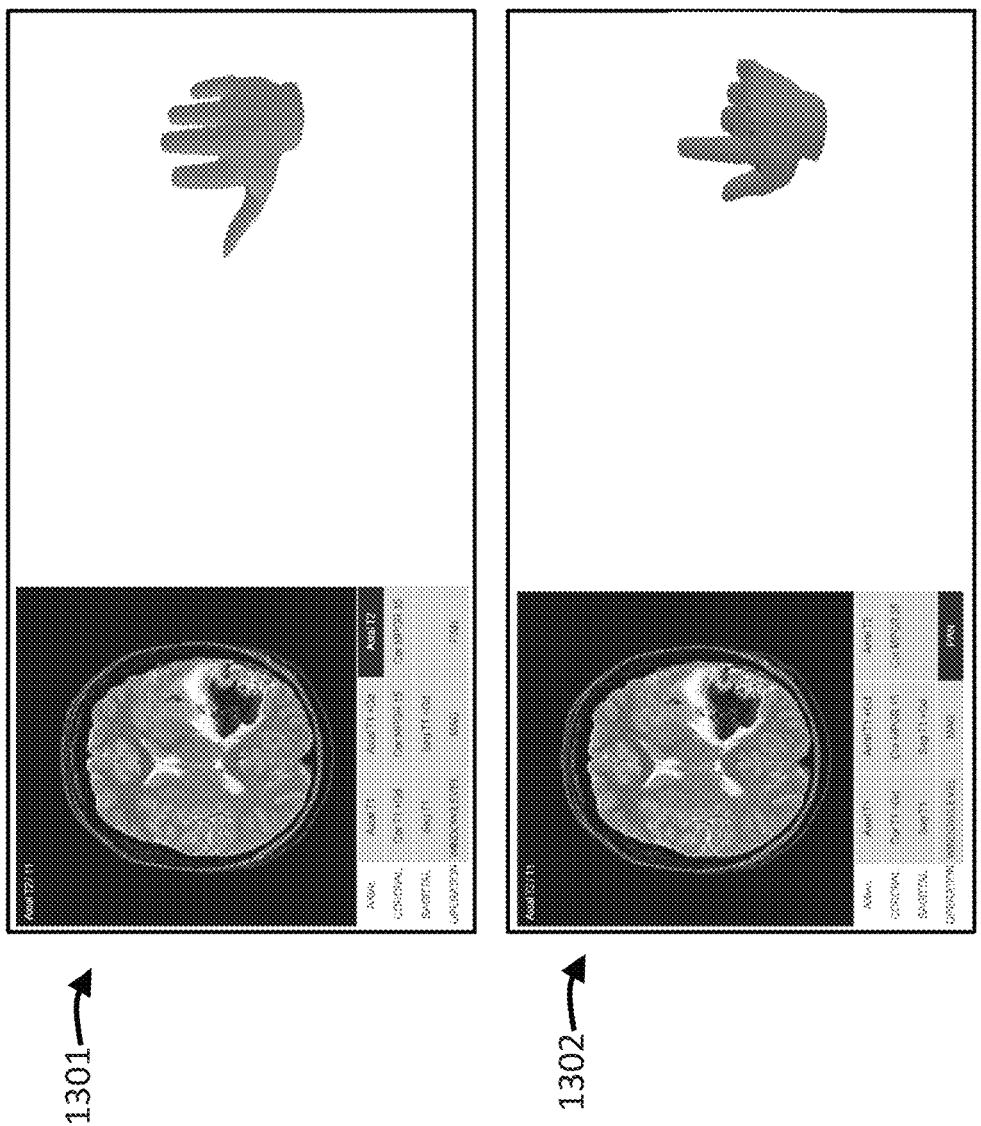

In the embodiment illustrated in view 1302 of FIG. 13A, a pointing configuration causes selection of the group of operations rather than the group of series. In the example shown, positioning the hand to the right causes selection of the operation displayed on the right, the Pan operation in the example of view 1302.

Comparing views 1301 and 1302, in view 1301 the users hand is in an open configuration, indicating selection of series/image, and on the right side of the working volume, indicating selected on the series listed on the right, the Axial T2 series in the example shown.

When the user changes his hand to a pointing configuration while maintaining its position on the right, the system automatically changes to "operation selection mode" and choses the operation indicated on the right, the "Pan" operation in the example shown.

Views 1303, 1304, and 1305 of FIG. 13B illustrate the result of hand motion, in the example shown from right to left, correlating with the series of operations listed in the last row of the graphical user interface.

As shown in view 1303, the user's hand is positioned on the right and the rightmost operation is selected, "Pan." As the user moves his hand toward the left, a point is reached where the system automatically selects and highlights the "Mag" operation, and with further movement to the left, the "Window/Level" operation.

In one embodiment, a particular hand configuration, such as pointing, may be combined with hand orientation to select among operations or group of operations. For example, different operations may be available for a pointed hand in the axial vs. coronal vs. sagittal orientations. Further, in various other embodiments, hand configuration may be used to provide one or more additional user inputs and may be applied to any of the embodiments described herein.

When an operation is selected, there is typically a need to provide input related to how the operation is to be applied to the displayed image. For example, in the case of magnification, there is a need for the user to provide input related to the degree of desired magnification or to increase or decrease the amount of magnification.

In the case of Window/Level, there is a need to provide two inputs, one to adjust the window level and one to adjust window width, similar to adjustment of image brightness and contrast.

As illustrated in the example embodiment of FIG. 14A, another hand configuration may be used to provide input for the selected operation. For example, in view 1401, the user used a pointed hand configuration to choose among the available operations, in the example shown, the Window/Level operation.

In one embodiment, a closed hand configuration, as illustrated in view 1402, is used to indicate to the system that hand location and/or movement is to be used to provide input to the selected operation.

In the example shown, the user selected the Window/Level operation as shown in view 1401. Then, as shown in view 1402, closing the hand, and moving it up/down and left/right is used to adjust window level and window width, respectively (or vice versa). A change in the configuration of the hand may cause the system to exit the adjustment to the selected operation.

In other embodiments, movement in one, two, or three perpendicular directions may be used to adjust one, two, or three parameters associated with the selected operation. For example, in an image editing application, movement of the hand in three perpendicular directions could be used to simultaneously adjust hue, luminance, and saturation.

In various embodiments, other combinations of user inputs (e.g., position and configuration), and transitions among user inputs, may be used to provide other updates to the system. For example, while the embodiment above describes hand configuration as the method of changing among "modes" (e.g., selection of a series, selection of an operation, and/or adjustment of parameters of an operation), another type of input, e.g., hand orientation, may be used for this purpose. In another example, when in the "adjustment of parameters of an operation" mode, orientation rather than, or in addition to, hand position, may be used to provide adjustments.

VII. Example Method in Which Modes of Operation are Selected

Figure 14B:
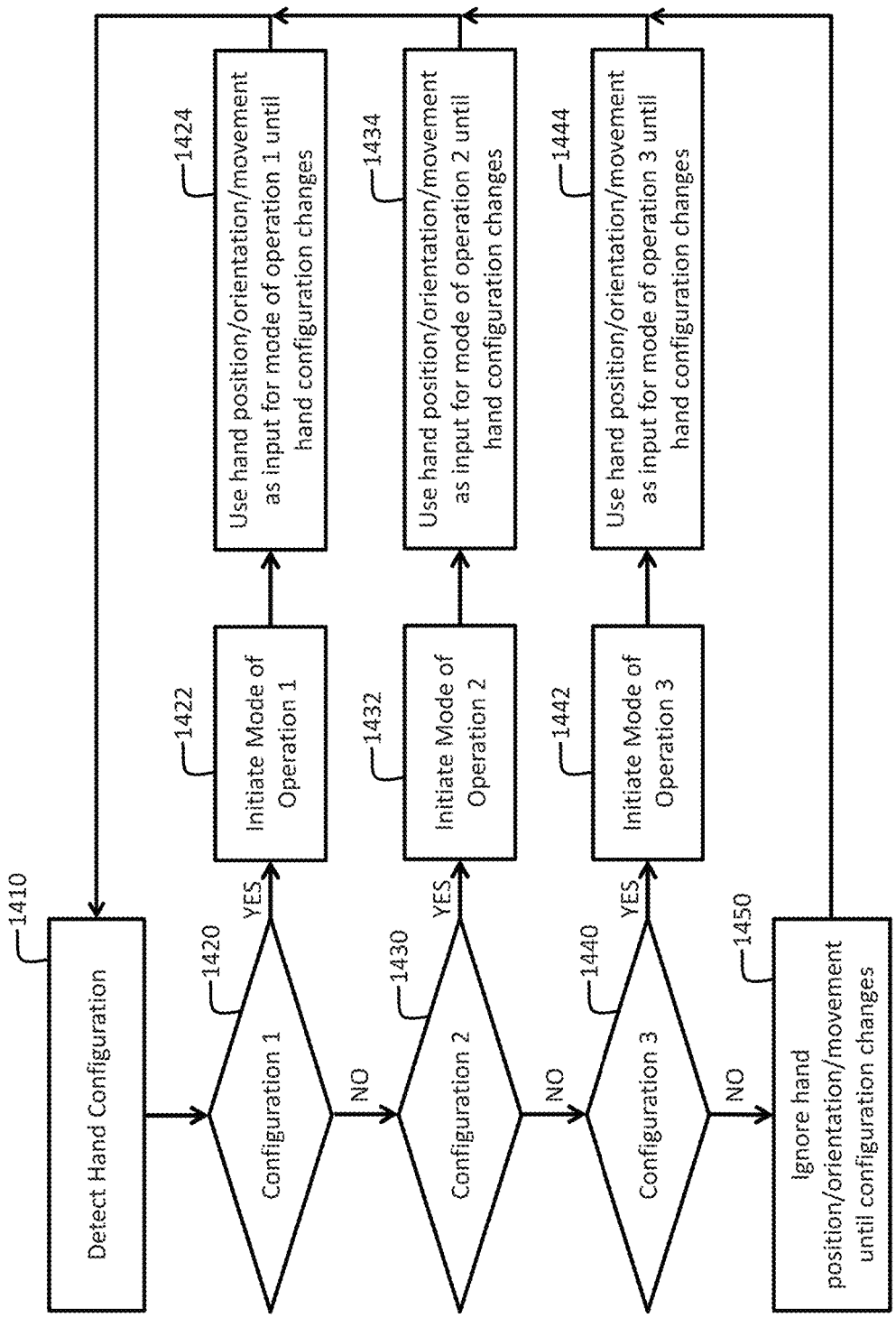
FIG. 14B is a flow chart illustrating yet another example method of user interaction with the system.
Figure 17:
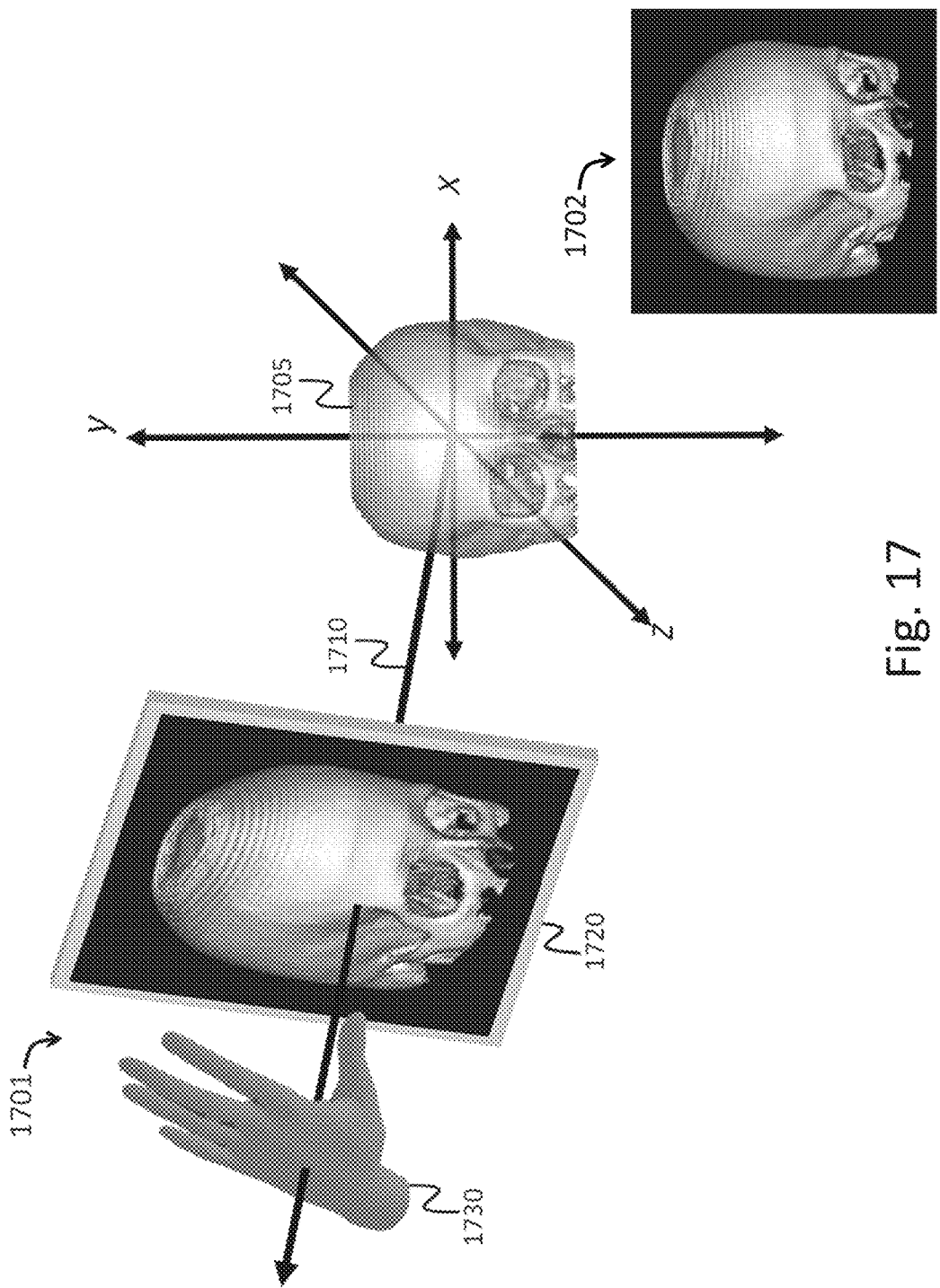
Figure 18:
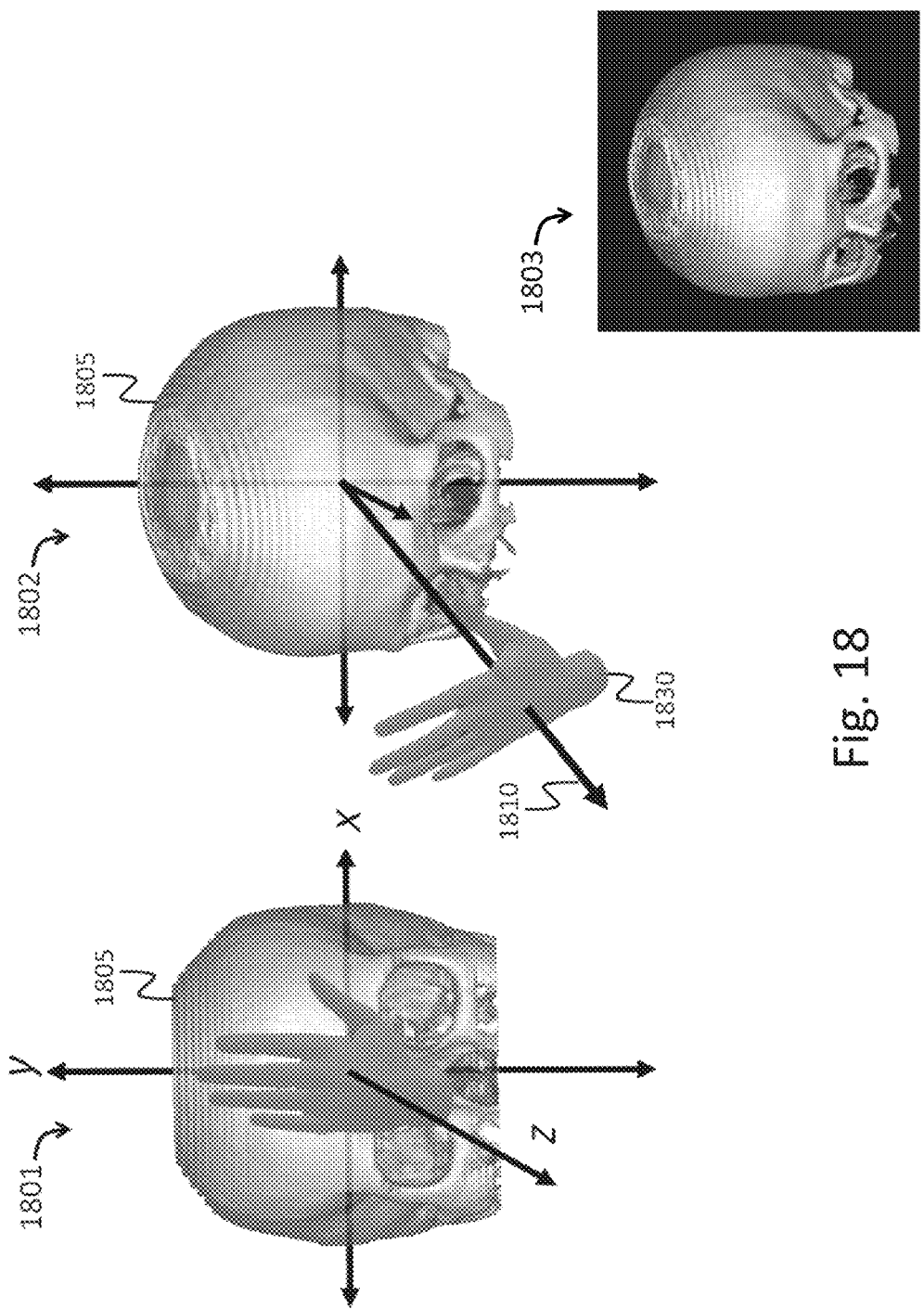

FIG. 14B is a flow chart illustrating another example method of user interaction with the system. Specifically, FIG. 14B illustrates a method of the system, according to an embodiment, in which user inputs (such as the example user inputs described above in reference to FIGS. 11-12 and 13A-13B and 14A), including hand configuration, are used to select modes of operation. The inputs are detected and converted into updated displays of data within a selected mode of operation. The method of FIG. 14B may be performed by the computing system 150 and/or a combination of the computing system 150, the server 120, and/or any other suitable computing device and/or system. Depending on the implementation, the system may perform methods having more or fewer blocks than are shown, and/or the blocks may occur in a different order and/or in parallel in order to accomplish the methods and/or processes of the system.

At block 1410, a hand configuration is detected by the system by, e.g., one or more sensors of the system as described above. In the embodiment of the system depicted in FIG. 14B, multiple hand configurations may be recognized by the system, and may cause selection of different modes of operation. As described above, hand configurations may include, for example, hand flat with fingers extended, hand in a fist, one finger extended, etc.

At block 1420, the system determines whether the detected hand configuration is a first configuration (e.g., open hand, as illustrated in diagram 1301 of FIG. 13A). If so, at block 1422 a first mode of operation is initiated (e.g., selection of a series) such that, at block 1424, movement, position, orientation, and/or other input via the user's hand (or in some embodiments, via other user inputs) causes changes to the selected mode of operation (e.g., change to different series).

If not, then at block 1430 the system determines whether the detected hand configuration is a second configuration (e.g., single extended finger, as illustrated in diagram 1302 of FIG. 13A). If so, at block 1432 a second mode of operation is initiated (e.g., selection of an operation to alter a view of an image) such that, at block 1434, movement, position, orientation, and/or other input via the user's hand (or in some embodiments, via other user inputs) causes changes to the selected mode of operation (e.g., change of the selected operation to the view of the image).

If not, then at block 1440 the system determines whether the detected hand configuration is a third configuration (e.g., closed fist, as illustrated in diagram 1402 of FIG. 14A). If so, at block 1442 a third mode of operation is initiated (e.g., adjustment of a selected operation to alter a view of an image, such as a change in brightness) such that, at block 1444, movement, position, orientation, and/or other input via the user's hand (or in some embodiments, via other user inputs) cause changes to the selected mode of operation (e.g., adjustment of the selected operation to the view of the image).

If not, then at block 1450 the system ignores movement, position, orientation, and/or other input (excepting hand configuration) via the user's hand. Accordingly, the user may select to, e.g., reposition their hand without causing other input by configuring their hand such that movements are ignored. Such a feature is useful when relative inputs are being used by the system, as described below in reference to FIG. 20.

While the embodiment illustrated in FIG. 14B includes three hand configurations, in other embodiments, fewer or more hand configurations may be implemented. Further, in some embodiments the system may detect, e.g., an orientation of the hand rather than a configuration of the hand to determine different modes of operation of the system.

VIII. Additional Example User Inputs

FIGS. 15-27 illustrate yet more user inputs to the system in which, according to various embodiments, a user's hand is used to manipulate displayed data. As with the example user inputs described above in reference to FIGS. 3-6, and with all example user inputs described herein, the user's hand as the tool to provide inputs to the system is illustrative. Other tools may be used to provide user inputs, for example other appendages, whole body movement, wands, and/or the like. While not specifically illustrated in many of the figures below, the described user inputs may be detected by one or more sensors of the system, and may be processed and translated into updates of displayed data, as described above and below. Further, while the various figures illustrate user inputs to interact with medical images and/or medical image series of a medical exam, the example user inputs may be used to interact with other types of data (as described above).

a. Example of Selection of Image Series and Performing Operations on the Series

FIG. 15 illustrates an embodiment in which hand position and/or motion are used to select a series and image within a series, and changing hand configuration is used to select an operation to perform on the selected images and/or series.

View 1501 illustrates the user's hand in an upright position, for example to select a group of series in a particular imaging orientation. In the example illustrated, a group of coronal series is selected. Positioning the hand in other orientations may be used to select a group of series in another imaging orientation. For example, a horizontal hand orientation may be used to select a group of axial series. In the example of view 1501, a particular series has already been selected and movement of the hand perpendicular of the hand orientation (e.g., along the illustrated z axis) is used to select an image from within the selected series.

View 1502 illustrates how movement of the hand within the plane of the hand orientation is used to select a particular series from within a group of series. In the example illustrated, hand orientation is used to select a group of series from the exam and movement of the hand within the plane of orientation is used to select a particular series from within the group selected.

View 1503 illustrates how a change in hand configuration is used to select and perform an operation. For example, in the example illustrated, changing to a pointing configuration selects an operation that allows the user to change image brightness and contrast. Once the operation is selected by changing hand configuration, change in hand location and/or hand movement may be used to provide input for the selected operation. In the example illustrated, moving the hand up/down and left/right changes image brightness and contrast. In one embodiment, other hand configurations may be used to select other operations. For example, holding up one finger, as in view 1503, might be used to select an operation to change window/level, while holding up two fingers might select a different operation, such as the zoom (e.g., magnification) operation.

In another embodiment, changes in hand configuration may be used select another image, for example from another exam. For example, the user may select two exams for display (e.g., a most recent exam and a comparison exam performed previously). Functionality to select a series within an exam and image within a series may be used, as in the example illustrated in views 1501 and 1502. The user may change hand configuration to switch back and forth between two exams, such as a current exam and a comparison exam.

For example, a user viewing a brain MRI exam may first select a particular image to display, such as coronal T1 image at a particular location in the brain. Then, by changing his hand configuration from an open configuration, such as illustrated in 1501, to a closed configuration, such as illustrated in view 1402 of FIG. 14, the system may automatically display a corresponding image from the comparison exam with similar properties, orientation and anatomical location.

b. Example of Hand Orientation as Input to Change View of 3D Rendered Data

FIG. 16 illustrates an embodiment in which absolute hand orientation or change in hand orientation is used to provide input to 3D rendering software. In the example illustrated in view 1601, positioning the hand in a lateral orientation results in reconstruction of a frontal view, in this case using data from a volumetric CT of the brain. Rotating the hand right and left, as illustrated in views 1602 and 1603, results in a change in rotation of the rendered image.

In one embodiment, absolute hand position may be used to control rendering parameters, whereas in another embodiment, change in hand orientation (e.g., relative change from an initial position) is used to change the rendering parameters (e.g., rotation around an axis).

In one embodiment, one hand configuration is used to provide input and another configuration is used to not provide input so that the user can reposition the hand. For example, a closed first configuration may be ignored by the system, allowing the user to position his hand into a comfortable orientation. Opening the hand may then cause the system to monitor change in hand orientation and/or position, and use change in orientation and/or position as input, for example, to change 3D rendering parameters.

c. Example of User Input to Indicate Camera Perspective From Which to Render 3D Data In the embodiment illustrated in FIG. 17, hand position and/or orientation (as represented by hand 1730 in position 1701) is used to position a virtual camera pointed at a position within the 3D volume to be rendered (as indicated by line 1710), for example its center. In for example, the user's hand location relative to a position in space may be used to control a virtual camera location where the camera is automatically pointed at a position within the volume to be rendered, such as its center.

In another embodiment, the orientation of the hand is also used to aim the camera so that it does not need to point at particular location in space but can be arbitrarily oriented.

In the example shown the location and/or orientation of hand 1730 relative to a position in space is used to render a view of volumetric data 1705, creating image 1702 and/or 1720 which is displayed on a computer display device.

d. Example of User Input to Rotate 3D Data to Indicate Perspective from which to Render Image In the embodiment illustrated in FIG. 18, change in hand orientation and/or position is used to provide input to 3D rendering software to control rendering parameters, such as rotation about various axes. This embodiment differs from that of FIG. 17 at least in that a hand position controls rotation of virtual object within a frame of reference, rather than a virtual camera position.

A hand space may be defined as a virtual volume or space in which the user may move his hand, where hand position is detected by a sensor, as described previously.

The position of the user's hand in this hand space is used to control rendering parameters. For example, in view 1801, the user's hand is positioned in a location that causes a frontal view of the volume 1805 to be rendered.

In view 1802, the user has repositioned his hand 1830 in the hand space. Vector 1810, along an axis between the origin of the hand space and the user's hand, has particular angles relative to the x, y, and z axes. These angles may be used as input parameters to the 3D rendering software to control the view rendered. For example, in the example of view 1802, an example rendered image displayed to the user on a computer display device is illustrated in view 1803.

e. Example User Input to Rotate 3D Data about an Axis

Figure 19:
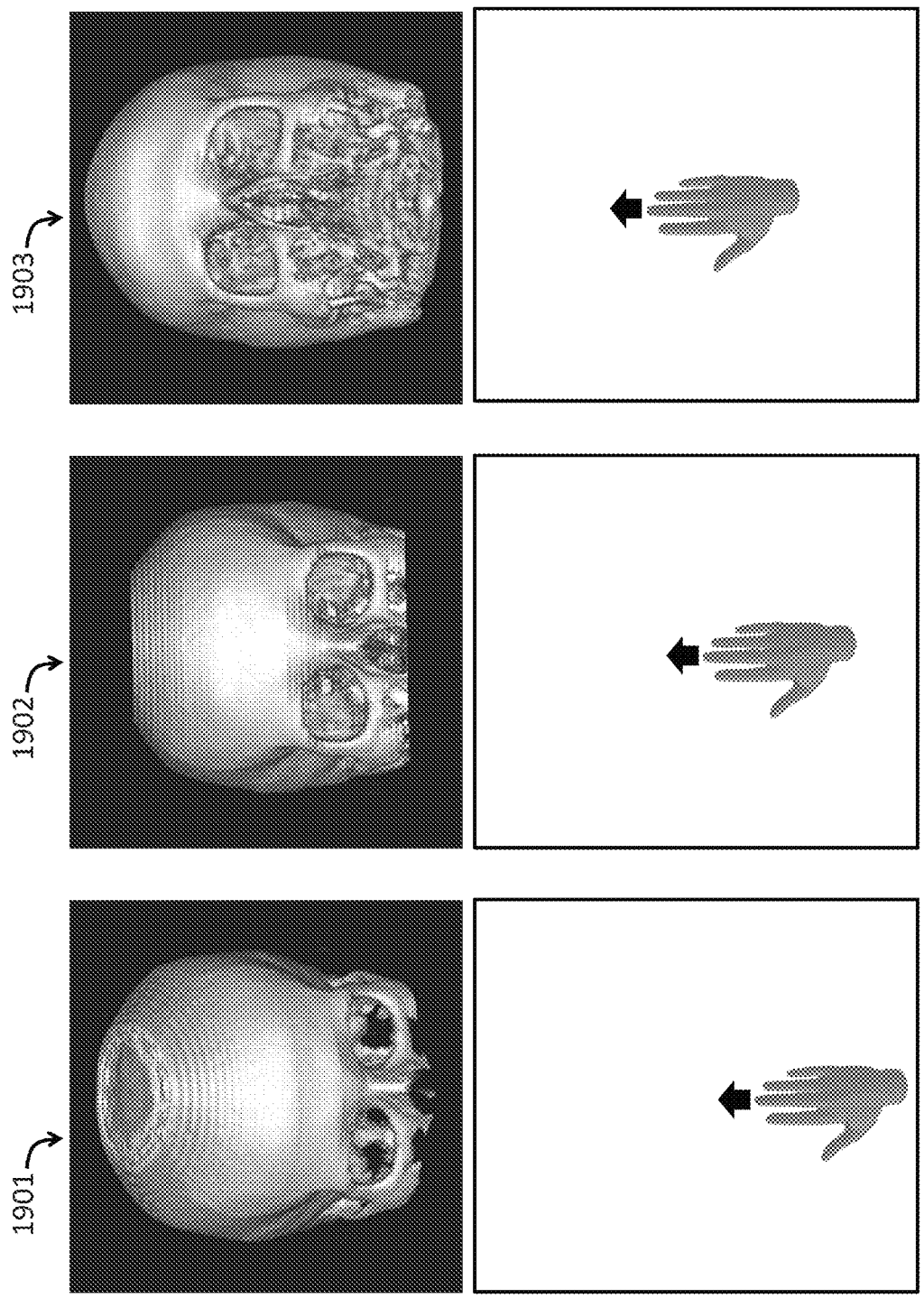
Figure 20:
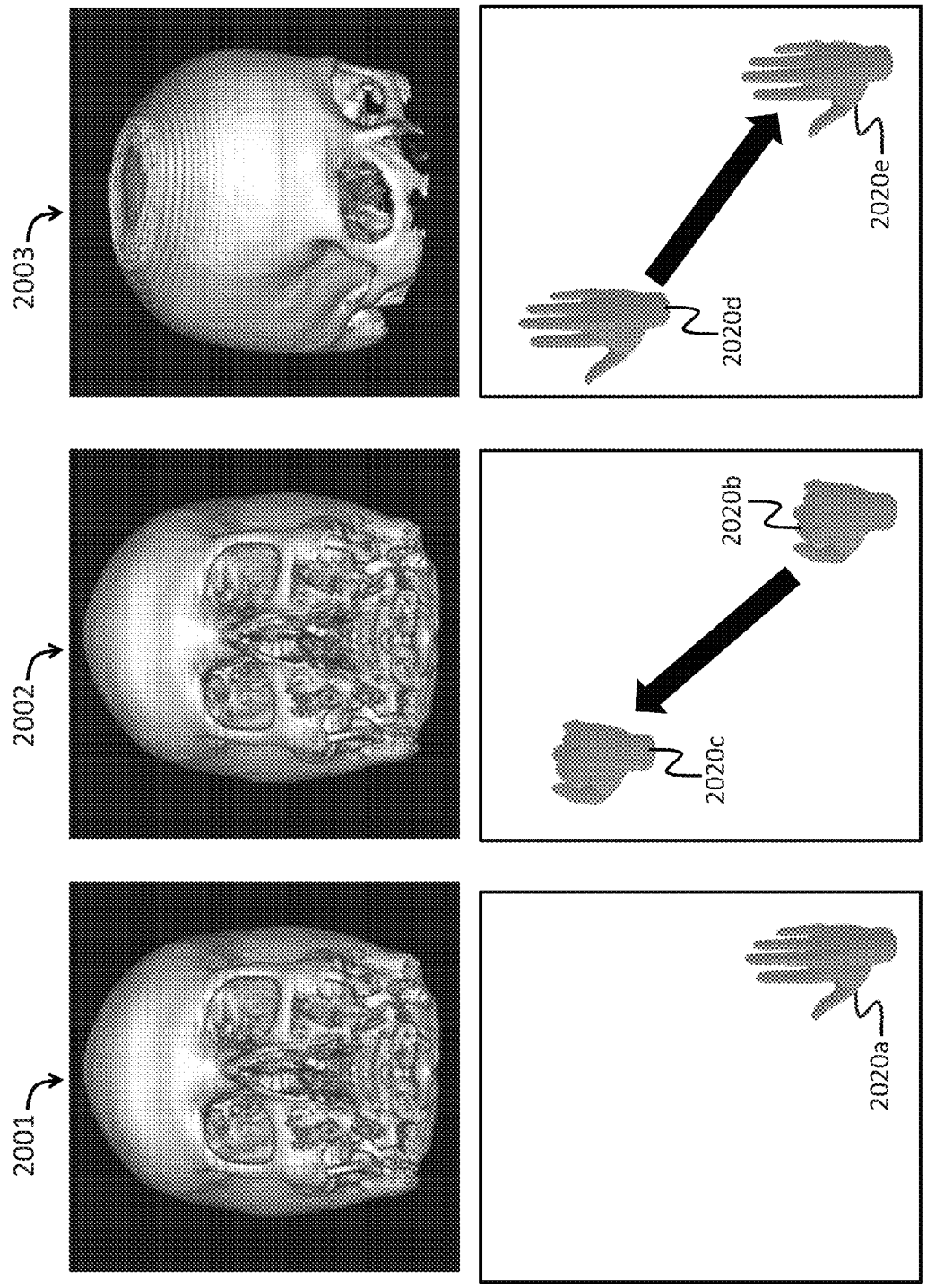

In another embodiment, as shown in FIG. 19, hand movement and/or position in one or two dimensions may be used as input to control 3D rendering parameters. In the example shown in views 1901, 1902, and 1903, up/down motion of the hand is used to control rotation around a particular 3D axis, such as the x axis. In one embodiment, left/right hand motion may also be used to control rotation around another axis, for example the y axis. As described above in various embodiments, the user inputs may be absolute and/or relative.

f. Example User Input in which Hand Configuration May Cause Hand Movement to not be Used as Input In the example of FIG. 20, one hand configuration is used to provide input while another hand configuration is ignored, so that the user can reposition his hand without providing input. In the example illustrated, an open hand is used to provide input while a closed hand is used to reposition the hand without providing input. In the example of FIG. 20, an open hand is used to provide input while a closed hand is not. In other embodiments, different hand configurations may be used.

In the example of view 2001, the user's open hand is in an arbitrary position 2020a. In view 2002, the user changes his hand configuration to a closed configuration 2020b, without changing his hand position. He then may move his hand to another position, such as 2020c, without providing input. In view 2003, the user changes this hand configuration, for example to the open hand configuration 2020d, at the same position. Then by moving his hand, for example to position 2020e, the user provides input that may be used to control 3D rendering software, for example changing the view rendered from that illustrated in view 2002 to that illustrated in view 2003. As described above in various embodiments, the user inputs may be absolute and/or relative.

g. Example User Input Based on Absolute Positioning of User's Hand

Figure 21:
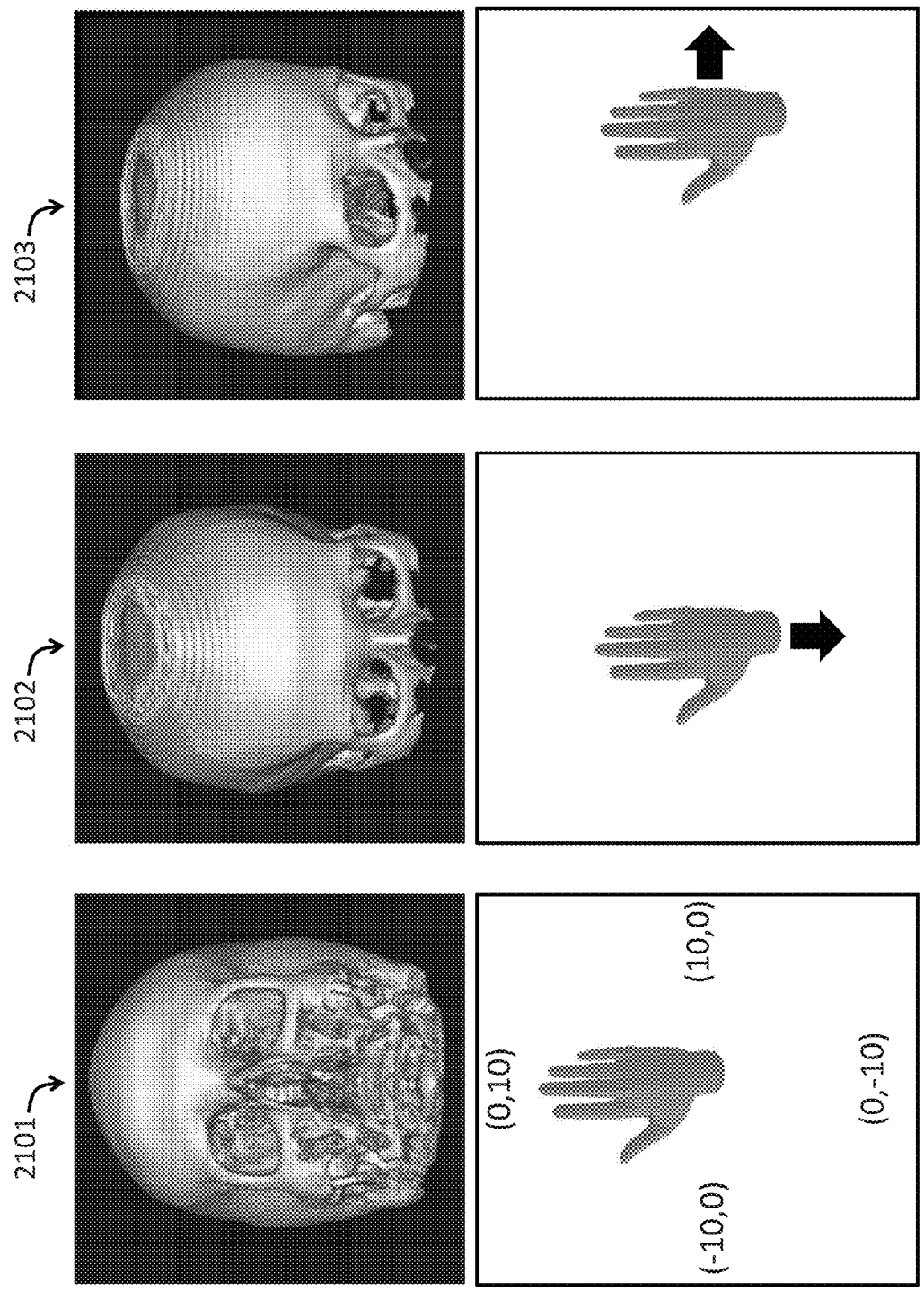

FIG. 21 illustrates an example where hand position and/or movement may be used to control 3D rendering parameters. In one embodiment, a hand space may be defined such that the absolute position of the hand may be used to control the rendering parameters. For example a hand space might be defined that is 20 cm in lateral (horizontal) and 20 cm in superior-inferior (vertical) dimensions, with an origin in a center at (0,0).

Positioning of the hand within this space may be mapped to values for rotation around axes. For example, positioning of the hand at (0,0) might map to a rotation of 0 in the x-axis and y-axis.

Positioning the hand to (10,0) might result in a rotation of +180 degrees around the y-axis and positioning of the hand to (−10,0) might result in a rotation of −180 degrees around the y-axis, with intermediate positions resulting in intermediate rotations.

Similarly, hand positioning in the perpendicular direction, between (0, −10) and (0, +10) may be mapped to rotation along the x-axis, say between −180 degrees and 180 degrees.

Arbitrary positioning of the hand within these horizontal and vertical locations within the hand space may result in corresponding arbitrary rotations.

FIG. 21 illustrates an example where the initial hand position illustrated in view 2101 results in a 3D rendering with no rotation around the y-axis and a small degree of rotation around the x-axis, causing the skull to be rotated superiorly slightly. In view 2102, the hand is moved inferiorly, causing rotation around the x-axis so that the skull in rotated inferiorly. In view 2103, the hand has been positioned toward the right and the skull is now rotated around both the x-axis and y-axis, as shown.

In various embodiments, as described below, the origin may be determined to be located relative to a real physical object, such as a sensor and/or display device. In one embodiment the origin is located above a sensor that is positioned on a table in front of the display device.

h. Example User Input Based on Relative Positioning of User's Hand

Figure 22:
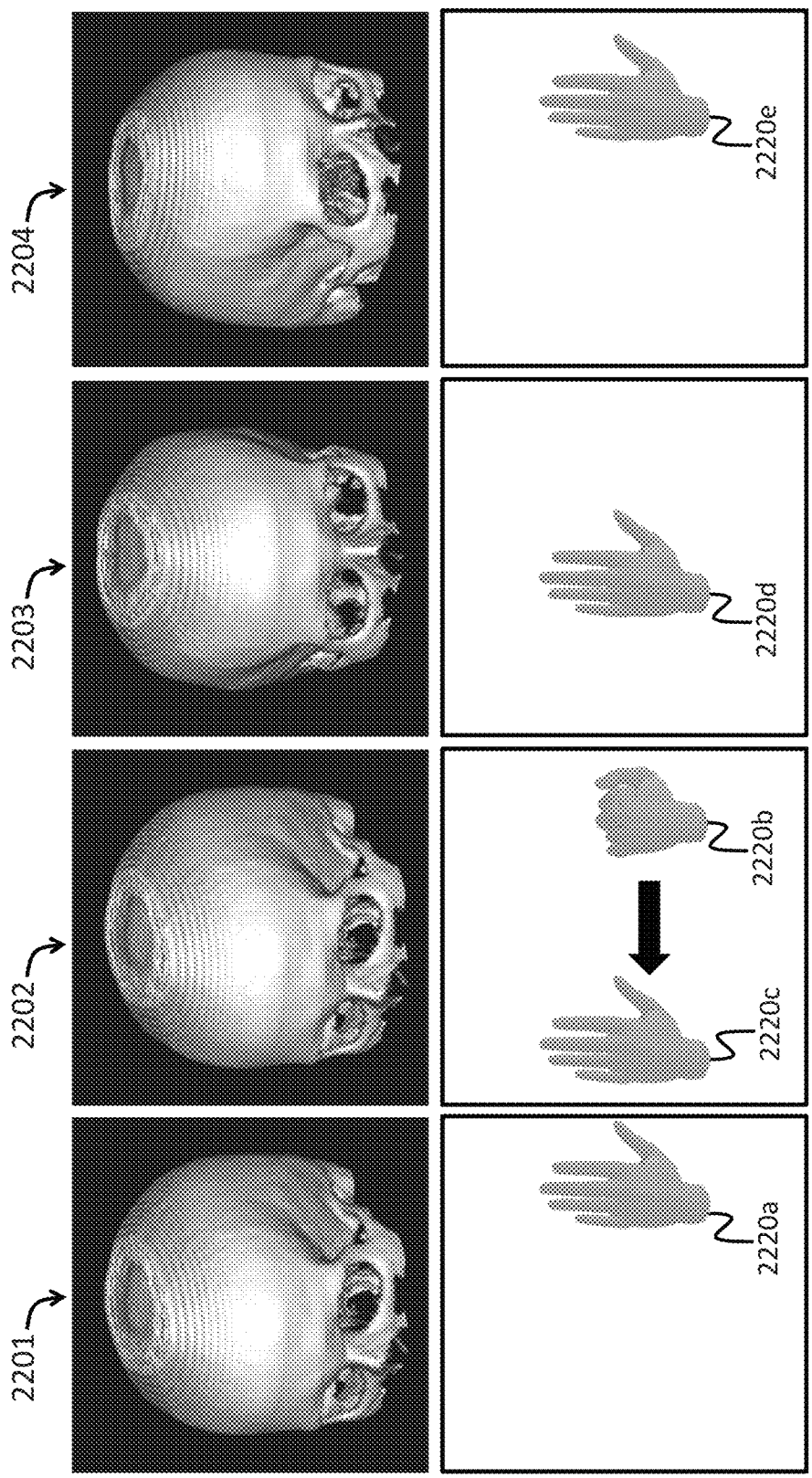

FIG. 22 illustrates an embodiment where hand motion results in incremental (also referred to herein as relative) changes in rotation and different hand configurations may be used to provide input, e.g., open hand, or be ignored, e.g., closed hand.

In view 2201, the user's hand is arbitrarily positioned at location 2220a.

In view 2202, the user closes his hand at the same position, shown as 2220b, indicating that hand movement is not to be used to change rotation. The user repositions his hand to position 2220c while closed and no change in rotation occurs as the hand is closed. In position 2220c, the user opens his hand, indicating that hand movement is to be utilized to change rendering parameters.

Figure 23:
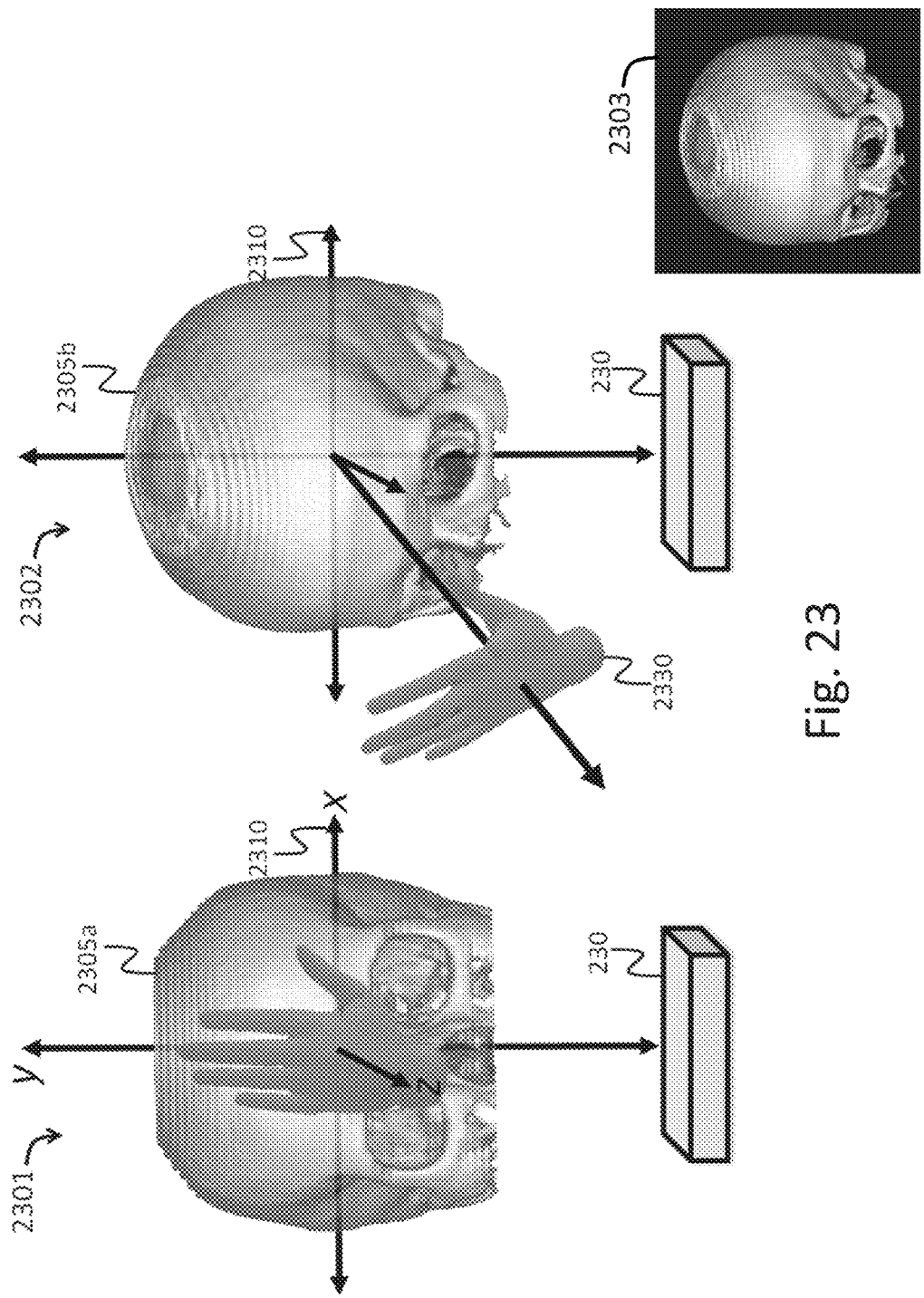
Figure 25:
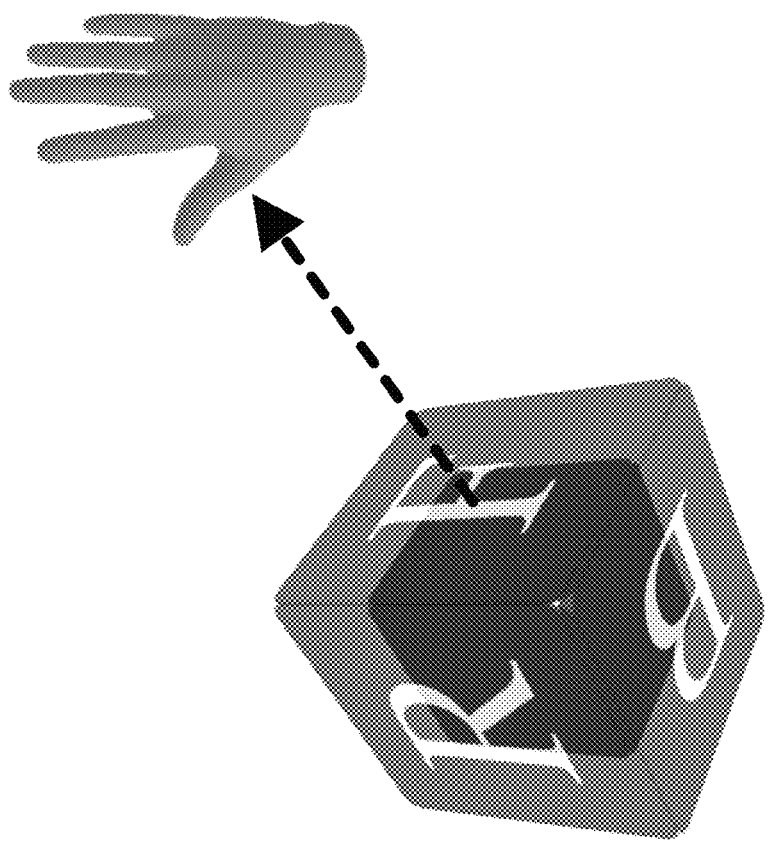
Figure 26:
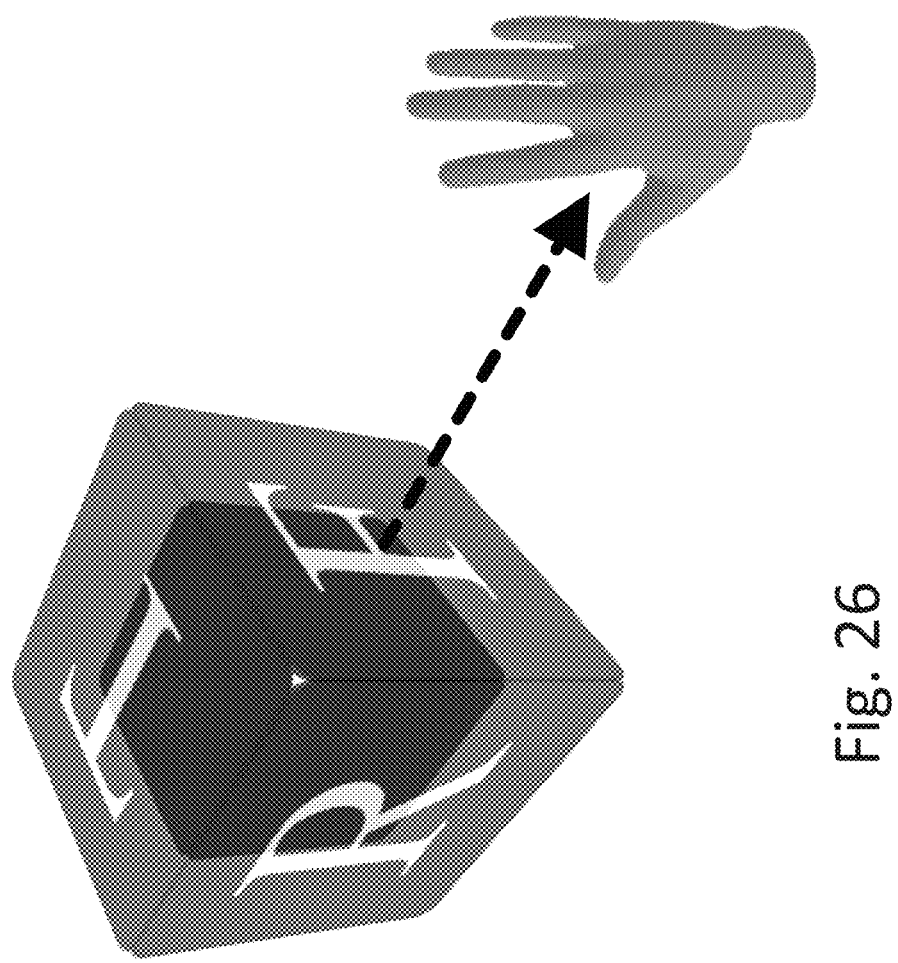
Figure 27:
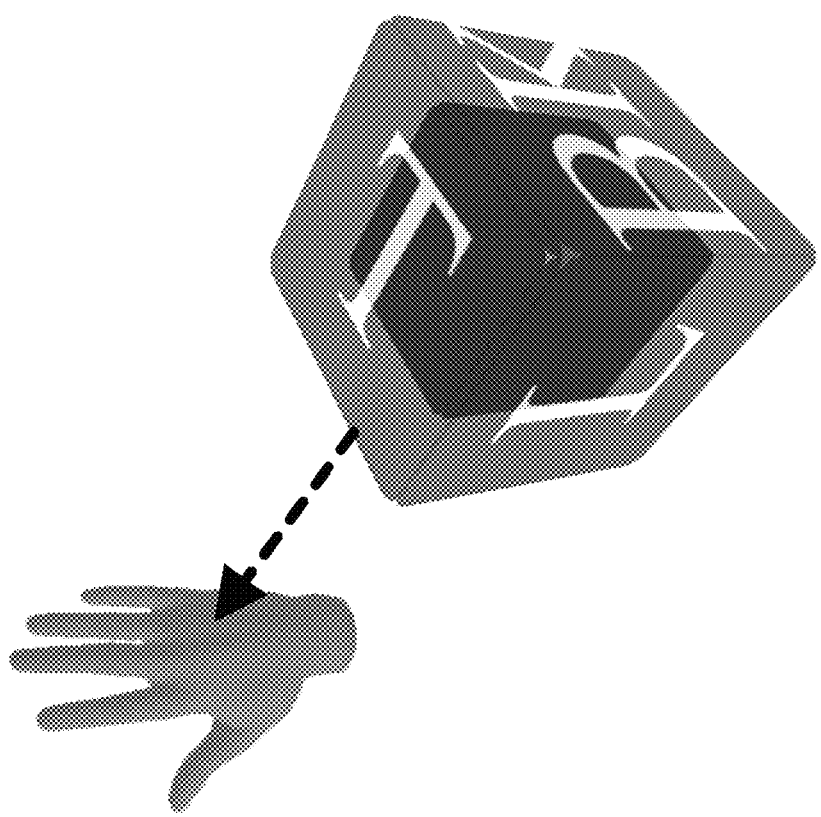

View 2203 shows that the user has moved his hand to the right to position 2220d, causing rotation around the y-axis. View 2204 shows future movement of the hand to position 2220e, causing further rotation of the rendered volume.

i. Example of User Input to Update Display of 3D Data by Tracking Position of a User's Hand in Space FIG. 23 illustrates an embodiment in which hand position and/or movement may be used as user inputs to control an orientation of a virtual 3D object presented on a display. In this embodiment, control of the virtual 3D object may be conceptualized by imagining that virtual 3D object 2305 (including orientations 2305a and 2305b in FIG. 23) is positioned in a region of space with respect to 3D sensor 230. For example, the virtual 3D object may be virtually positioned above the 3D sensor 230 when the 3D sensor is sitting on a desk. Further, in some examples the position of the virtual 3D object may be anterior or posterior to the location of the 3D sensor 230, or at some other spatial offset.

The locations of the user's hand with respect to the 3D sensor 230 may be used by the system to determine an orientation of the virtual 3D object. For example, as the user moves his hand from the location shown in diagram 2301 to the location shown in diagram 2302, the virtual 3D object changes from orientation 2305a to orientation 2305b. The position of user's hand 2330 may be determined by reference to a coordinate system 2310 that may be arbitrarily defined with respect to the location of the 3D sensor 230. In an example, the virtual 3D object may be conceptually located around the general location of the origin of the coordinated system of the 3D sensor 230.

The location of the user's hand may be determined based on, for example, a center of the palm of the user's hand and/or a tip of a finger of the user's hand. In various embodiments the orientation of the user's hand may be ignored such that only the location/position of the user's hand with respect to the coordinate system of the 3D sensor 230 is used to determine an orientation of the virtual 3D object.

In the embodiment of FIG. 23, in order to more fully understand how the position of the user's hand controls the movement of the virtual 3D object, it may be helpful to imagine a string or rubber band connecting the user's hand to a fixed position in or on the virtual 3D object. Then, as the user's hand is moved in 3D, the front (or other predefined portion) of the virtual 3D object follows the user's hand thereby determining 3D rendering parameters used to generate 3D view 2303. Thus, in one embodiment the user's hand can move generally in a sphere pattern around the object in order to cause the object to adjust orientation to any X, Y, and Z orientation.

In some embodiments, hand configuration may be used to control tracking. For example, in some examples an open hand may cause the position of the hand to be tracked (and the orientation of the virtual 3D object changed), while a closed first may cause the tracking to be stopped (e.g., stopped temporarily until the user's hand is opened again.)

In various embodiments, as described above, various user inputs, including orientation, gesture, and/or other movements of the user's hand, may be used separately and/or in combination with the position of the hand to cause other control of the virtual 3D object. For example, an orientation or configuration of the user's hand may be used to select different 3D data. In this example, if two or more sets of similar 3D data are available (e.g., two different imaging exams of a patient's head), the user may use the orientation or other configuration of their hand to switch between the exams. The same current orientation of the virtual 3D object (as determined by the position of the user's hand) may be displayed for each exam such that the user may easily switch between the two and compare them. For example, in an embodiment where the position of the palm of the hand is used to control the orientation of the 3D display, the user could elongate 1, 2 or 3 fingers to cause display of a 3D reconstruction from the 1st, 2nd and 3rd exams, respectively.

While the embodiments discussed herein describe 3D movement of an object in response to a particular portion of the object having an affinity to the position of the user's hand (e.g., such as by imagining a string attached to the user's hand, as noted above), in other embodiments other paradigms for affecting movement of a 3D object using a hand (or other body part or object) may be used in order to accomplish the same goals as disclosed herein. For example, in one embodiment the user's hand could be envisioned as a camera from which the 3D object is viewed, such that as the hand is moved around the object, the view that is displayed on the display device is from the perspective of the user's hand with reference to the object (as described above in reference to FIG. 17). Thus, this paradigm provides different interactions with the 3D object, but may be preferable to certain users. Accordingly, depending on embodiment, the system may allow the user an option of selecting which movement paradigm should be used, e.g., the hand attached to a string on a front of the object paradigm or the hand as a camera that moves around the object paradigm. In other embodiments, other viewing paradigms may be used.

FIGS. 24-27 illustrate examples of control of display of the virtual 3D object as the user's hand is moved about in three-dimensional space, as described in reference to FIG. 23. In the examples, a three-dimensional cube is used to represent data with which the user may be interacting. The faces of the cube are labeled for convenience as follows: F for front, L for left, R for right, BK for back, T for top, and B for bottom. As shown in FIGS. 24-27, the orientation of the virtual 3D object tracks the movement of the user's hand such that the front of the cube (indicated by the "F") follows the user's hand. In various embodiments any arbitrary position on or within the object displayed may be configured to follow the position of the user's hand or a component of the user's hand, e.g., a pointed finger.

IX. Determining an Orientation of a 3D Object Based on User Input

Figure 28:
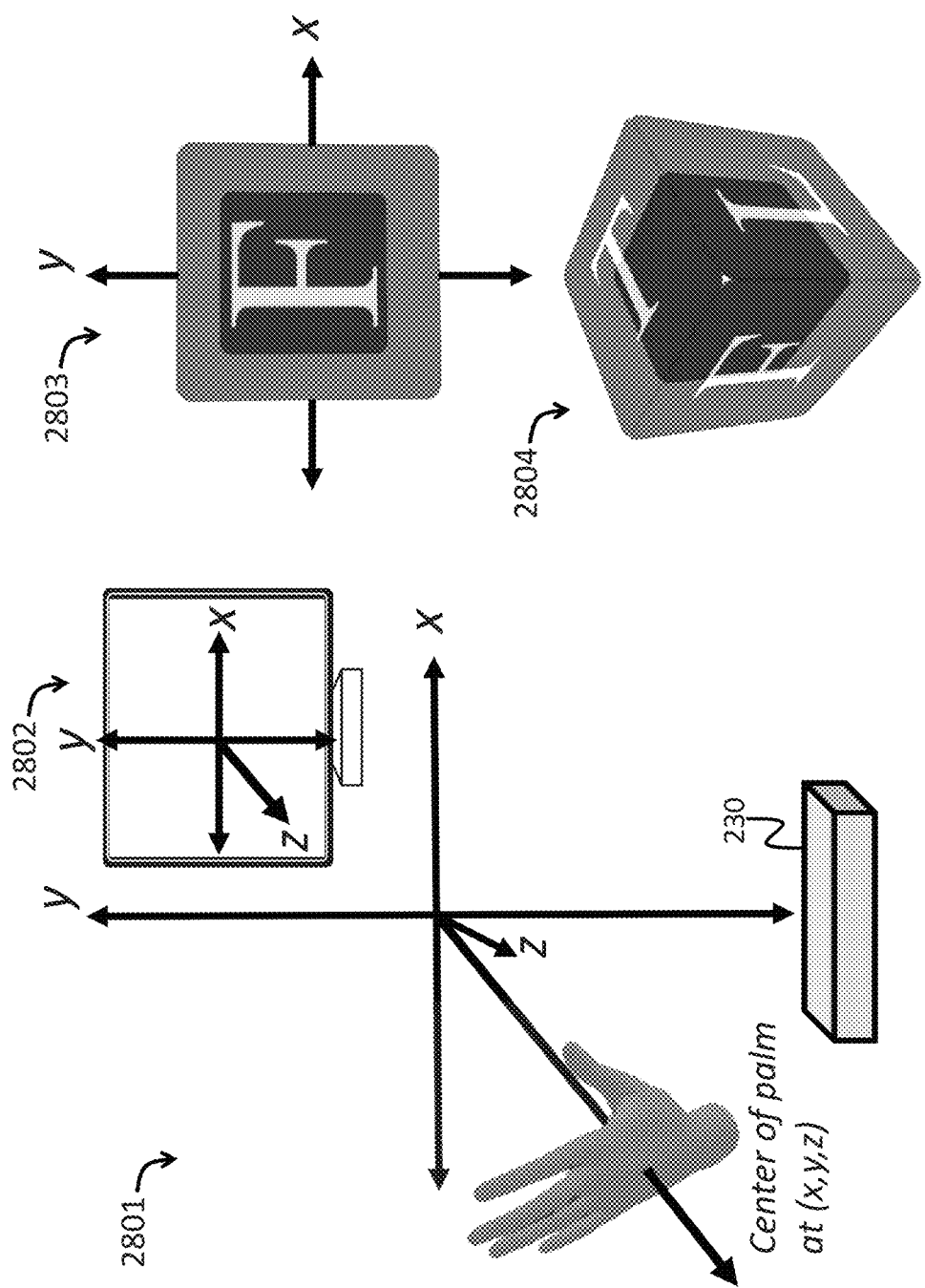
FIG. 28 is a diagram illustrating an example method of determining an orientation of a virtual 3D object based on a position of a user's hand and/or other user input, according to an embodiment.
Figure 29A:
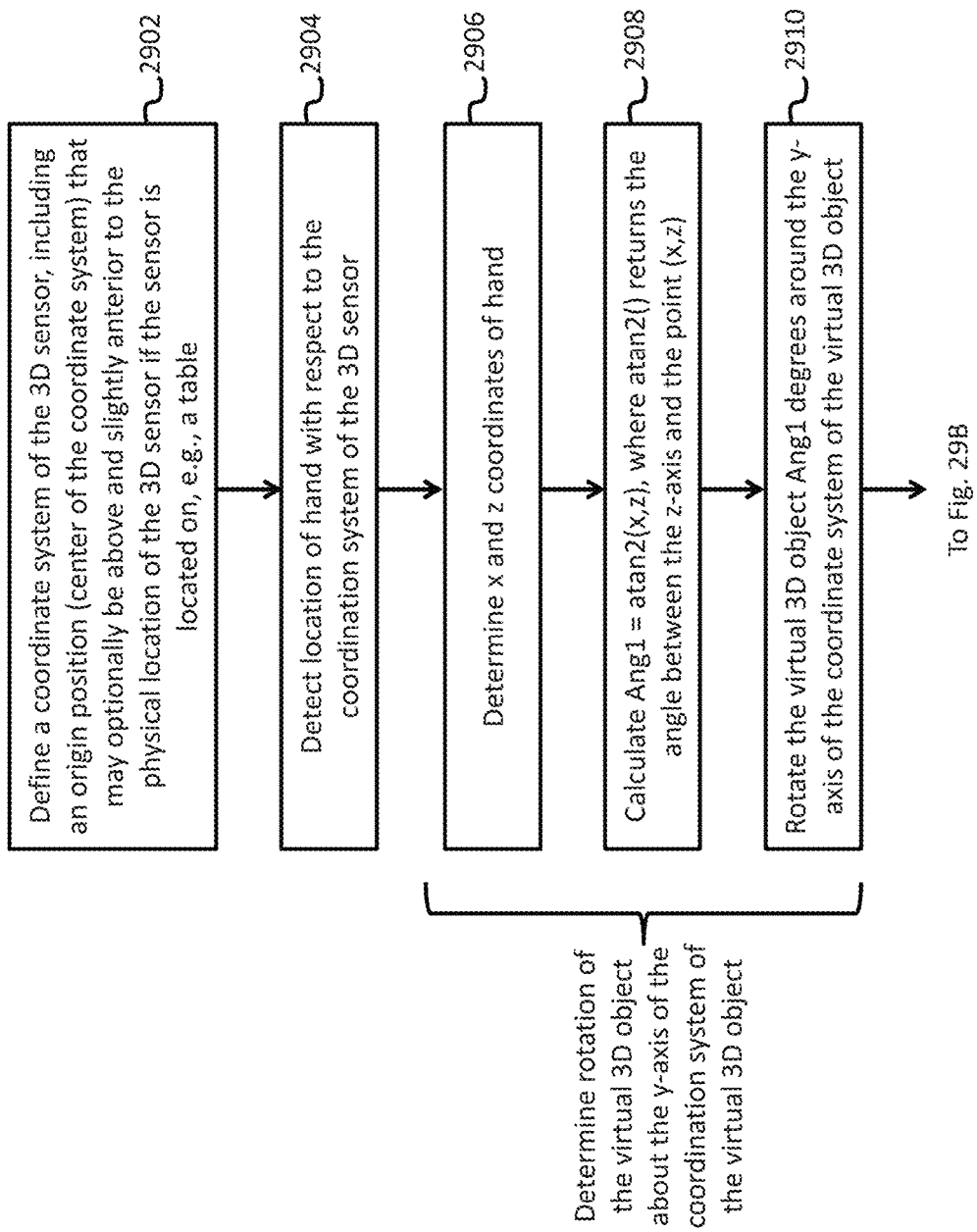
FIGS. 29A-29B show a flow chart illustrating an example method of system corresponding to the method illustrated in FIG. 28.
Figure 29B:
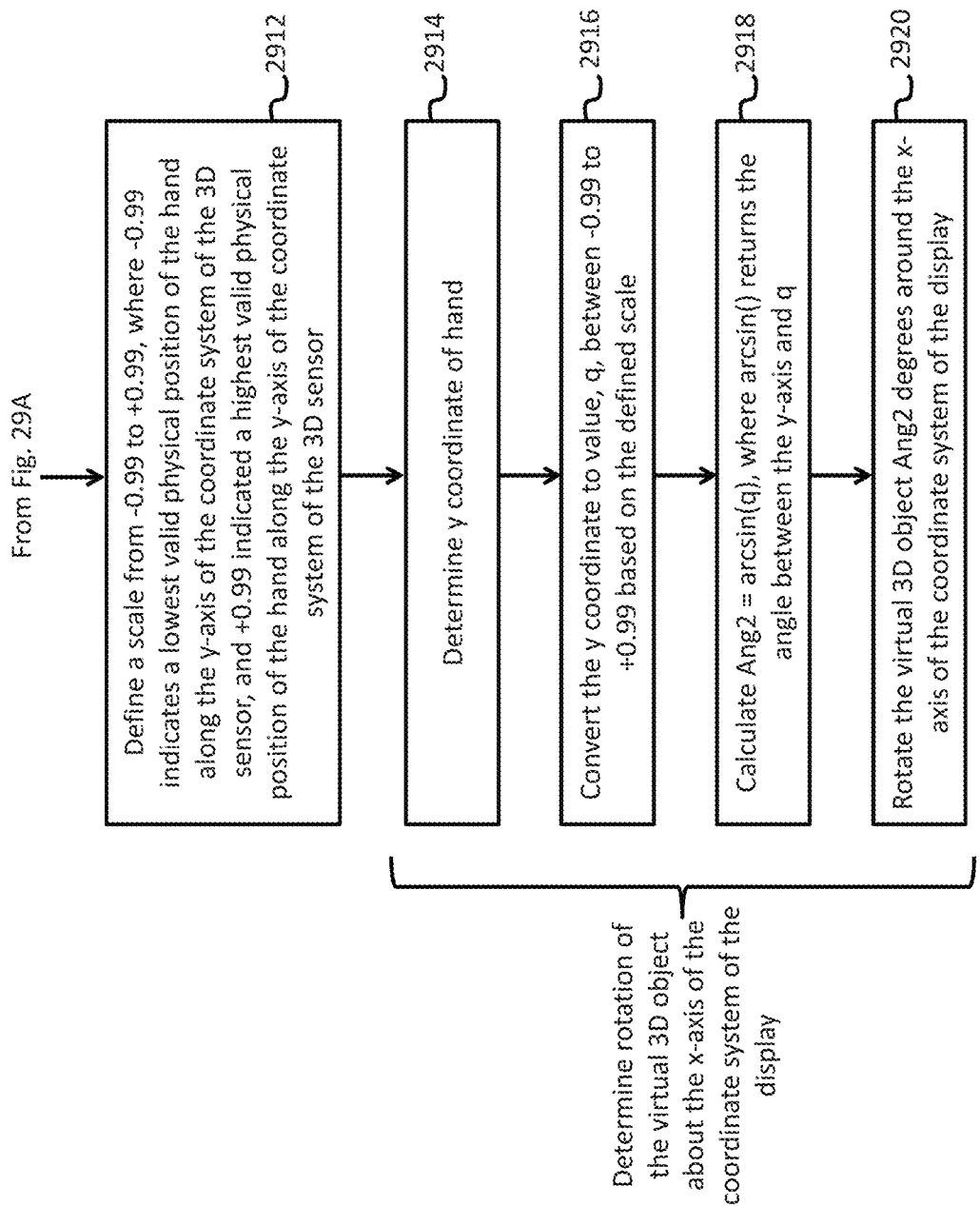

FIGS. 28, 29A, and 29B illustrate a method of determining an orientation of the virtual 3D object (as described above in reference to FIGS. 23-27) based on a position of the user's hand with respect to a coordinate system of the 3D sensor 230.

Referring to FIG. 28, coordinate systems are shown with respect to the 3D sensor 230 (e.g., coordinate system 2801) and the display (e.g., coordinate system 2802). In some instances these two coordinate systems may be aligned (for example, when the 3D sensor 230 is located directly under the display. However, more commonly the coordinate systems of the 3D sensor 230 and the display will be offset from one another, but have a similar alignment. Accordingly, the user may imagine the virtual 3D object to be located at the origin or at an offset of the coordinate system of the 3D sensor 230, and the virtual 3D object may be displayed on the display based on the coordinate system of the display as if the coordinate systems of the display and 3D sensor 230 were the same.

As described above, the coordinate system of the 3D sensor 230 may be arbitrarily defined. A position of the user's hand with respect to the 3D sensor 230 may be defined by (x,y,z) coordinates of the 3D sensor 230 coordinate system, as shown.

Additionally, a coordinate system with respect to the virtual 3D object may be defined. In the example shown, the coordinate system 2803 of the virtual 3D object is defined based on the initial orientation of the virtual 3D object. For example, the z-axis of the coordinate system of the virtual 3D object may point to the user's hand such that the z-axis perpendicularly intersects the virtual 3D object at the point that is generally described herein as the point that tracks the position of the user's hand.

As the user's hand moves about 3D space, its location is tracked by the 3D sensor 230 and the coordinates are determined. The system calculates an orientation of the displayed virtual 3D object based on the coordinates of the user's hand, and uses the calculated orientation to display an updated view of the virtual 3D object (an example of which is shown in view 2804). An example of a method for calculating the virtual 3D object orientation is described in the flowchart of FIGS. 29A-29B.

At block 2902, the coordinate system of the 3D sensor 230 is defined as described above. At block 2904, the location of the user's hand is determined, as described above.

At blocks 2906-2910, a rotation of the virtual 3D object about the y-axis of the coordinate system of the virtual 3D object is determined. In particular, at block 2906, the x and z coordinates of the hand (within the coordinate system of the 3D sensor 230) are determined. Then at block 2908 an angle Ang1 is calculated by taking a tan 2( ) of the x and z coordinates. Angle Ang1 thereby indicates an angle between the z-axis and the point (x,z) (in the coordinate system of the 3D sensor 230). In block 2910 the virtual 3D object is rotated about the y-axis of the coordinate system of the virtual 3D object by Ang1 degrees.

At block 2912, the system defines a scale from −0.99 to +0.99, where −0.99 indicates a lowest valid physical position of the hand along the y-axis of the coordinate system of the 3D sensor, and +0.99 indicates a highest valid physical position of the hand along the y-axis of the coordinate system of the 3D sensor. In other embodiments, the scale may be defined for any arbitrary number of values representing some valid positions of the hand, e.g., values between −1 and +1, −0.999 and +0.999. Further, in other embodiments, values on the scale may be defined with any level of granularity.

At blocks 2914-2920, a rotation of the virtual 3D object about the x-axis of the coordinate system of the display (which is oriented similarly to the coordinate system of the 3D sensor 230, as described above) is determined. At block 2914, the y coordinate of the hand (within the coordinate system of the 3D sensor 230) are determined. Then at block 2916, the y coordinate is converted to a value "q" that is between −0.99 and +0.99 (or other values), based on the defined scale. At block 2918, an angle Ang2 is calculated by taking arcsin( ) of "q". Angle Ang2 thereby indicates an angle between the y-axis and "q" (in the coordinate system of the 3D sensor 230). In block 2920 the virtual 3D object is rotated about the x-axis of the coordinate system of the display by Ang2 degrees.

Accordingly, the virtual 3D object displayed on the display is shown with an orientation that corresponds to the user's hand position in space with reference to the coordinate system of the 3D sensor 230, as described herein.

In one embodiment, when multiple imaging exams on a patient are available, a change in hand configuration may be used to select an exam to display (e.g., from the multiple imaging exams) (as described above in reference to, e.g., FIGS. 13A-13B and 14A-14B), while hand position is simultaneously used to control 3D display. For example, in response to the system detecting that the user is holding up one, two, or three fingers, the system may display a first, second or third exam in the 3D view, while the 3D view displayed is simultaneously controlled by hand position. In another embodiment where multiple volumetric series are included within an exam, a change in hand configuration may be used to select among different series within the exam. Accordingly, in some embodiments, when the user moves their hand around with an open hand configuration he may see the current exam, while moving their hand around with a closed hand (first) may switch to the prior exam, displayed at the same orientation. Therefore the user may move their hand around in 3D to control the 3D display and at any time switch back and forth between old and new exams by opening and closing their hand (or providing other changes in hand configuration or other inputs), facilitating comparison among related images from multiple exams and/or series.

In various embodiments, the blocks of the flowchart of FIGS. 29A-29B may be performed in a different order than shown. For example, the calculations of Ang1 and Ang2, and the rotation of the virtual 3D object, may be performed in a different order and/or simultaneously. Further, as is apparent from the description of user interactions herein, the process described may be performed repeatedly and rapidly as the user moves their hand such that the orientation of the virtual 3D object appears to track the user's hand in real-time. For example, the calculations may be performed many times per second.

Figure 30:
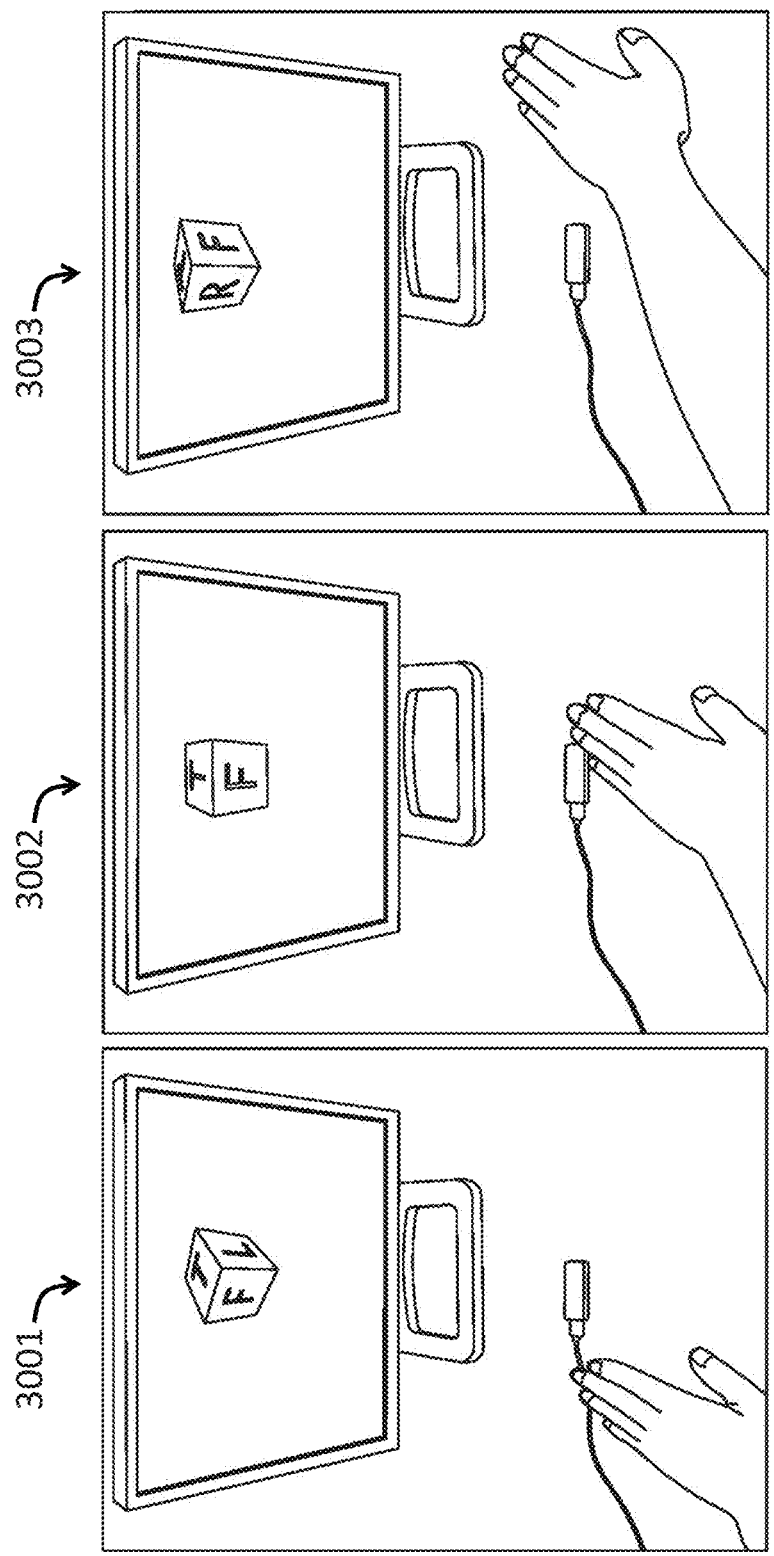
Figure 31:
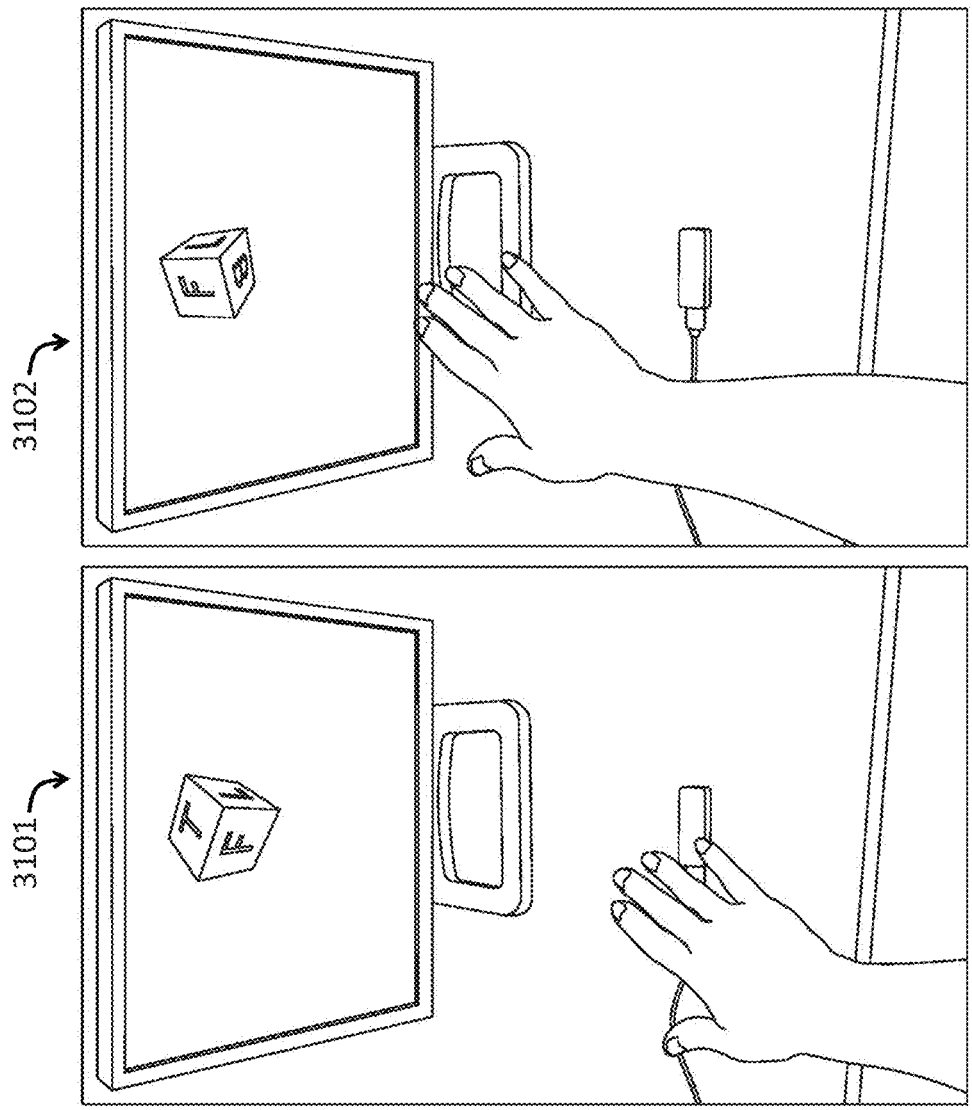
Figure 32:
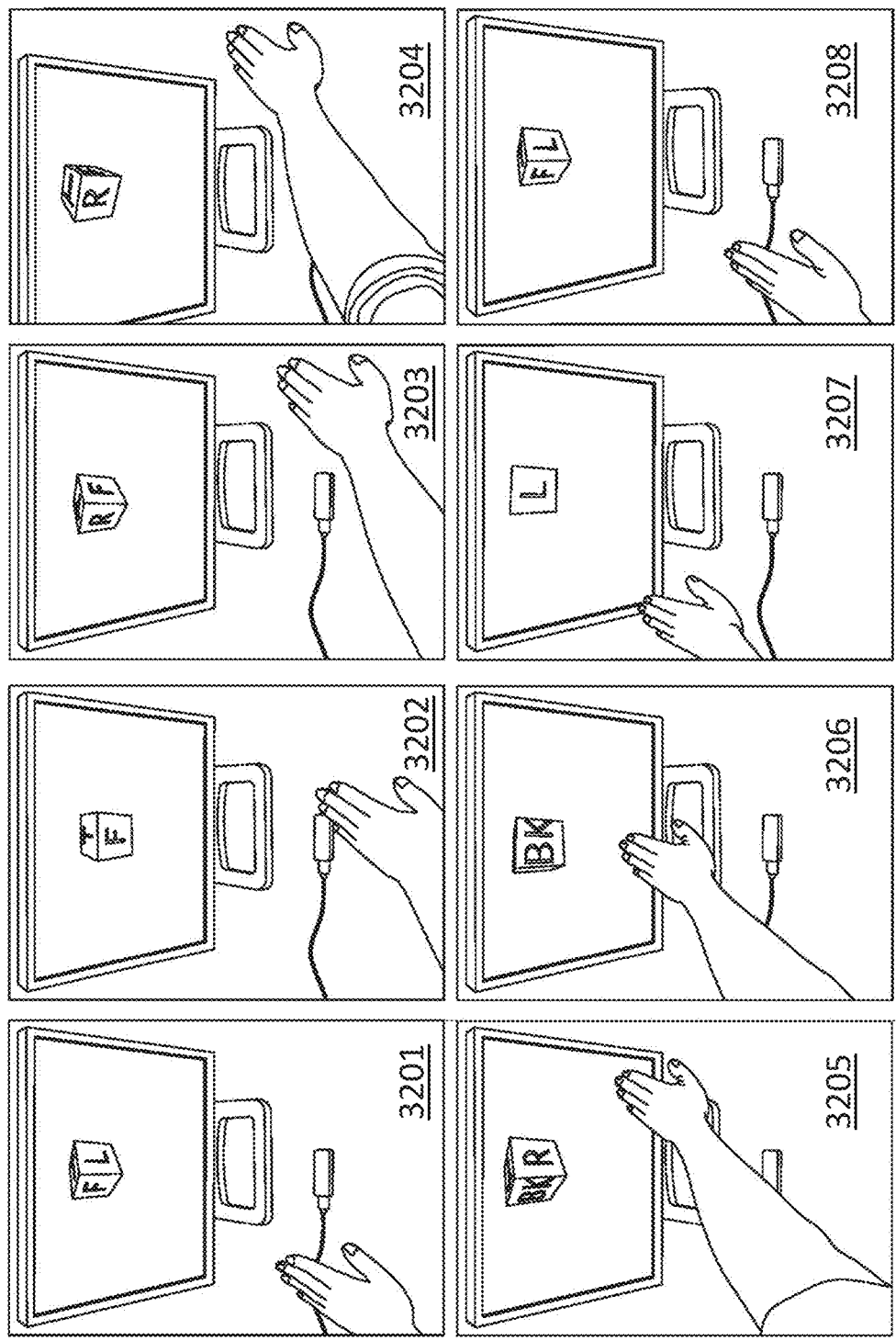

FIGS. 30-32 illustrate examples of movement of the virtual 3D object as the user's hand is moved about in three-dimensional space with reference to the 3D sensor 230, according to the embodiments described above with reference to FIGS. 23-28, and 29A-29B. As described above, a virtual 3D space may be imagined above the 3D sensor 230, in which the virtual 3D object is located. As the user moves their hand around in the virtual 3D space, the face of the object tracks the hand's location.

In FIG. 30, as the user's hand moves in the horizontal plane from 3001 to 3002 to 3003, the object shown on the display rotates around the y-axis. In this example, moving the hand from left to right in front portion of the virtual 3D space rotates the object as the front face of the object tracks the hand.

In FIG. 31, the user's hand moves superiorly from view 3101 to view 3102 which changes the vertical view of the virtual 3D object (e.g., the virtual 3D object rotates along x-axis) as the front face continues to track the hand. Here moving the hand from a lower to higher position (e.g., from view 3101 to 3102) tilts the object up.

In FIG. 32, views 3201-3208 show the user moving his hand counterclockwise in roughly the same plane around the center (origin) of the virtual 3D space, causing the object to rotate around the y-axis as the front of the object tracks his hand position. The hand is posterior to the origin of the virtual 3D space in views 3205 and 3206 so the back ("BK") of the object is visible as the front face points away from the user. Comparing image 3202 to 3201, the user has repositioned his hand both horizontally and vertically, causing the object rotation to change along both the y-axis (front face oriented more toward user in 3202) and x-axis (front face tilted more inferiorly in 3202).

Figure 34:
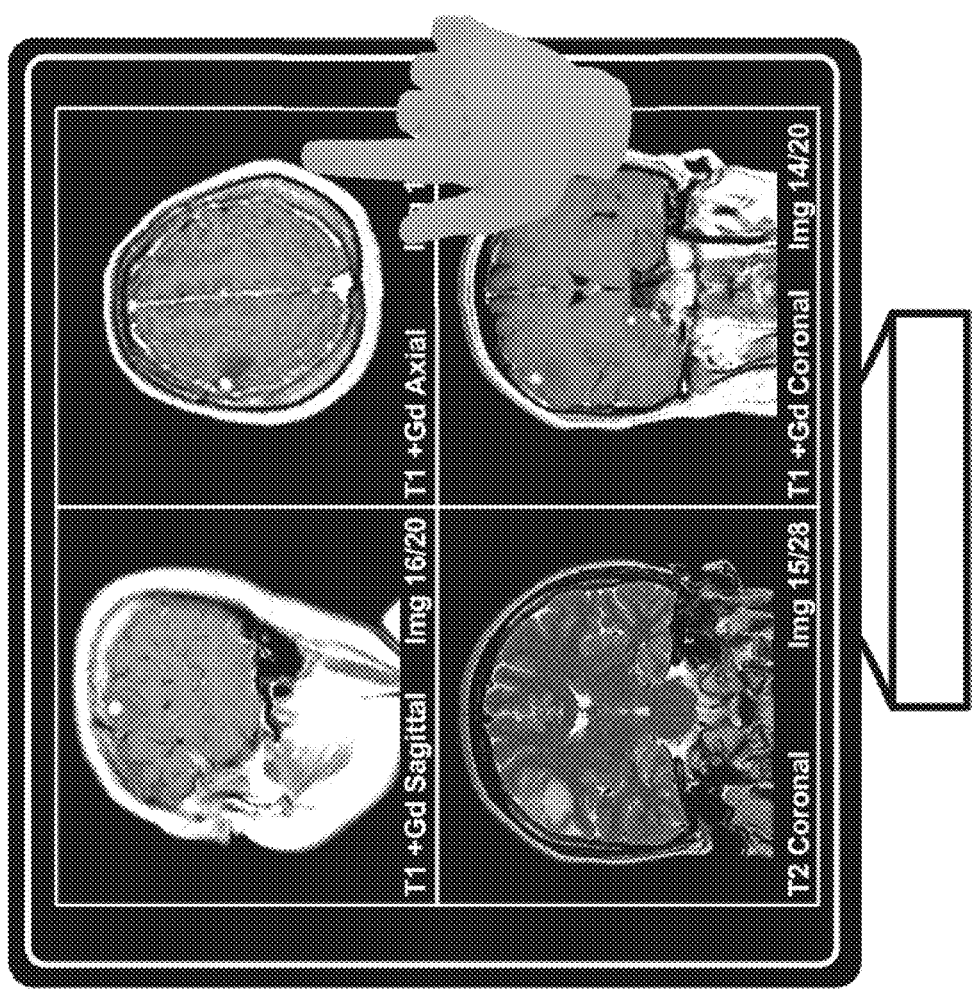

X. Example User Input to Indicate a 3D Spatial Position in a Medical Imaging Exam FIGS. 33-34 illustrate yet more example user inputs to the system in which, according to various embodiments, a user's hand is used to manipulate displayed data. As with the example user inputs described above in reference to FIGS. 3-6, and with all example user inputs described herein, the user's hand as the tool to provide inputs to the system is illustrative. Other tools may be used to provide user inputs, for example other appendages, whole body movement, wands, and/or the like. While not specifically illustrated in many of the figures below, the described user inputs may be detected by one or more sensors of the system, and may be processed and translated into updates of displayed data, as described above and below. Further, while the various figures illustrate user inputs to interact with medical images and/or medical image series of a medical exam, the example user inputs may be used to interact with other types of data (as described above).

Referring to FIG. 33, in an embodiment a position of a user's hand, or portion of the user's hand (e.g., a finger), may be used to select a 3D spatial position to be displayed within a medical imaging exam. View 3301 illustrates a 3D hand space with the user's hand positioned within it. This 3D hand space may be mapped to the anatomical volume imaged by a medical imaging exam.

View 3302 illustrates four image series within a medical imaging exam. A 3D pointer (circle with lines extending inward) corresponds to the 3D position indicated by the user's finger within the 3D hand space. The 3D pointer within each of the sagittal, axial, and coronal images corresponds to the same location.

When the user moves the position of his finger, the image displayed from within each series is updated so that images corresponding to the new 3D position are displayed. In addition the position of 3D pointer displayed in the images is updated in real time.

The images displayed could be 2D images from acquired series or images dynamically reconstructed, for example using MPR or MIP, from volumetric acquisitions.

Referring to FIG. 34, in another embodiment, a position of a user's hand, or portion of the user's hand (e.g., a finger), relative to computer display device may be used to select a particular frame from among a series of display frames that are displayed on a monitor. In the example of FIG. 34, a 2×2 array of display frames are shown, each displaying an image from a different series. The user has positioned his pointed finger over the upper right frame, causing it to be selected. Once a frame is selected, the user may move his hand, for example, along an axis perpendicular to the monitor, to navigate through the various images within the series shown within the selected frame.

In another embodiment, a different hand configuration may be used to first select a frame and then to change the image displayed within the frame. For example, a pointed hand configuration might be used to first select a frame. Then, the user may change his hand to a second configuration, for example a closed fist, to indicate to the system that subsequent hand movement is to be used to change the image displayed within the frame. For example, the user may move his closed hand along a vertical axis to navigate through the images within the series displayed within the selected frame.

XI. Example Computing Systems

Referring again to FIG. 1, various configurations of the computing system 150 and network environment 100 may be used to implement and/or accomplish the systems and methods disclosed herein. For example, the computing system 150 may be configured to display and/or enable a user to view and/or interact with various types of data including two-dimensional images, three-dimensional volumes, and/or other types of information, as described above. As described above, the computing system may take various forms. In one embodiment, the computing system 150 may be an information display computing device and/or system, a server, a computer workstation, a desktop computer, a Picture Archiving and Communication System (PACS) workstation, a laptop computer, a mobile computer, a smartphone, a tablet computer, a wearable computer (for example, a head-mounted computer and/or a computer in communication with a head-mounted display), a smartwatch, a mobile computer, a cell phone, a personal digital assistant, a gaming system, a kiosk, an audio player, and/or any other device that utilizes a graphical user interface, such as office equipment, automobiles, airplane cockpits, household appliances, automated teller machines, self-service checkouts at stores, information and other kiosks, ticketing kiosks, vending machines, industrial equipment, and/or a television, for example. In an embodiment the computing system 150 comprises one or more computing devices in communication with one another.

The computing system 150 may include various components including, for example, one or more processors 152, memory and/or data storage 153 (including one or more software modules 151 and/or a rules engine 163 (which may itself comprise a software module)), an operating system 154, a display 155, one or more input devices 156, one or more interfaces 157, an audio input/output 158, and/or one or more sensors 161 (including, for example, zero or more motion sensors 159, zero or more orientation sensors 160, and/or zero or more location sensors 162). Each of the components of the computing system 150 may be connected and/or in communication with each other using, for example, a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing system 150 (as described above and below) may be combined into fewer components and modules or further separated into additional components and modules.

In various embodiments the software modules 151 may provide functionality as described above with reference to the various figures. For example, modules 151 of the computing system 150 may include image display modules, motion detection/determination modules, orientation detection/determination modules, position detection/determination modules, location detection/determination modules, patient information display modules, rules engine modules (for example, rules engine 163), user interface modules, and/or the like. For example, each of the motion, orientation, position, and/or location detection/determination modules may determine user movements and/or gestures such that the user may interact with two-dimensional and three-dimensional images and/or volumes, as described above. Further, the image display modules and/or the user interface modules may display images and/or other data on the display 155 in response to movements of and/or gestures of the user. Further, the image display modules and/or the user interface modules may be configured and/or designed to generate user interface data useable for rendering the interactive user interfaces described herein, such as a web application and/or a dynamic web page displayed by a computing device. In various embodiments the user interface data may be used by the computing system 150, and/or communicated to any other computing device, such that the example user interfaces are displayed to a user. For example, the user interface data may be executed by a browser (and/or other software program) accessing a web service and configured to render the user interfaces based on the user interface data.

The rules engine 163 may operate in conjunction with the other modules to perform various functionality of the data navigation systems described above. For example, the rules engine 163 may determine, based on one or more rules of the user preferences and rules database 124, that a user input (e.g., a particular type of movement and/or gesture) is to be translated into a particular adjustment of a displayed image and/or other data. Such a determination may be based on, for example, a type of data displayed.

As described below, the software modules 151 may include various software instructions, code, logic instructions, and/or the like that may be executed by the one or more processors 152 to accomplish the functionality described above. In other embodiments, software modules 151 may reside on another computing device and/or system, such as a web server or other server (for example, server 120) or other server, and a user may directly interact with a second computing device and/or system that is connected to the other computing device and/or system via a computer network.

The computing system 150 may run an off-the-shelf operating system 154 such as a Windows, Linux, MacOS, Android, or iOS, or mobile versions of such operating systems. The computing system 150 may also run a more specialized operating system which may be designed for the specific tasks performed by the computing system 150, or any other available operating system.

The computing system 150 may include one or more computer processors 152, for example, hardware computer processors. The computer processors 152 may include central processing units (CPUs), and may further include dedicated processors such as graphics processor chips, or other specialized processors. The processors may be used to execute computer instructions based on the software modules 151 to cause the computing system 150 to perform operations as specified by the modules 151. The software modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, Objective-C, Swift, JavaScript, ActionScript, Visual Basic, HTML, Lua, C, C++, or C#. While "modules" are generally discussed herein with reference to software, any modules may alternatively be represented in hardware or firmware. In various embodiments, the modules described herein refer to logical modules that may be combined with other modules or divided into sub-modules despite their physical organization or storage.

The computing system 150 may also include memory 153. The memory 153 may include volatile data storage such as RAM or SDRAM. The memory may also include more permanent forms of storage such as a hard disk drive, a flash disk, flash memory, a solid state drive, or some other type of non-volatile storage.

The computing system 150 may also include or be interfaced to one or more display devices that provide information to the users. Display devices 155 may include a video display, such as one or more high-resolution computer monitors, or a display device integrated into or attached to a laptop computer, handheld computer, smartphone, smartwatch, wearable computer, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers. As described above, images and other information may be displayed to the user via the display devices 155 such that the user may efficiently view and interact with such images and information.

The computing system 150 may also include or be interfaced to one or more input devices 156 which receive input from users, such as a keyboard, trackball, mouse, 3D mouse, dial and/or knob (for example, a smartwatch crown), drawing tablet, joystick, game controller, touch sensitive surface (for example, capacitive or resistive touch screen), touchpad, accelerometer, video camera and/or microphone.

The computing system 150 may also include one or more interfaces 157 which allow information exchange between the computing system 150 and other computers and input/output devices using systems such as Ethernet, Wi-Fi, Bluetooth, as well as other wired and wireless data communications techniques.

The computing system 150 may include the audio input/output 158 for receiving, for example, audio commands or other input from the user. The audio system may also provide audio output to provide audio information to a user, for example via a speaker or headset. As described above, various sensors of the computing system 150 may include, for example, gyroscopes, accelerometers, cameras, Global Positioning System (GPS) transceivers and devices, near field communication (NFC) technology devices, Radio Frequency Identification (RFID) device, systems and devices utilizing WiFi, systems and devices utilizing Bluetooth such as iBeacons, and/or the like. The various sensors may provide input/data to the computing system 150 related to the location, position, orientation, and/or motion of a user and/or a user's appendage (such as an arm and/or hand). Such information may be processed by, for example, one or more software modules 151 (such as the rules engine 163) as described above, such that displayed image data (or other types of data) may be updated. Additionally, as described above, the system may also include, in some embodiments, external sensors 125 that may also provide data related to user inputs (including, e.g., gestures, etc.). External sensors 125 may include any of the sensors described herein, and may provide functionality similar to that described herein with reference to the various sensors. In various embodiments, the functionality provided by image storage 122 and/or server 120 may reside within computing system 150.

The computing system 150 may communicate and/or interface with other systems and/or devices. In one or more embodiments, the computing system 150 may be connected to the computer network 190. The computer network 190 may take various forms. For example, the computer network 190 may be a wired network or a wireless network, or it may be some combination of both. The computer network 190 may be a single computer network, or it may be a combination or collection of different networks and network protocols. Additionally, the computer network 190 may include one or more local area networks (LAN), wide area networks (WAN), personal area networks (PAN), cellular or data networks, and/or the Internet.

Various devices and subsystems may be connected to the network 190. As shown in FIG. 1, for example, the computing system 150 may be in communication with the image storage 122, the server 120, and/or the external sensor(s) 125. Image storage 122 may be a database, data store, or other electronic or computer-readable medium storage device configured to store, for example, medical images and/or three-dimensional imaging data. Such medical images and/or three-dimensional imaging data may be processed, for example, by the server 120 and/or the computing system 150. Further, the various components of the network environment 100 may be in communication with various other devices that may, for example, capture and provide images and/or other data to the computing system 150. For example, one or more medical scanners may be connected, such as MRI scanners. The MRI scanner may be used to acquire MRI images from patients, and may share the acquired images with other devices on the network 190. The network 190 may also include one or more CT scanners. The CT scanners may also be used to acquire images and, like the MRI scanner, may then store those images and/or share those images with other devices via the network 190. Any other scanner or device capable of inputting or generating information that may be presented to the user as images, graphics, text or sound may be connected to the network 190, including, for example, computing systems used in the fields of ultrasound, angiography, nuclear medicine, radiography, endoscopy, pathology, dermatology, and the like.

Also connected to the network 190 may be a Picture Archiving and Communications System (PACS) and/or PACS workstation. The PACS System may be used for the storage, retrieval, distribution and presentation of images (such as those created and/or generated by the MRI scanner and/or CT Scanner). The medical images may be stored in an independent format, an open source format, or some other proprietary format. A common format for image storage in the PACS system is the Digital Imaging and Communications in Medicine (DICOM) format. In various embodiments, the stored images may be transmitted digitally via the PACS system, often reducing or eliminating the need for manually creating, filing, or transporting film jackets.

The network 190 may also be connected to a Radiology Information System (RIS). In an embodiment, the radiology information system may be a computerized system that is used by radiology departments to store, manipulate and distribute patient radiological information.

Also attached to the network 190 may be an Electronic Medical Record (EMR) system. The EMR system may be configured to store and make accessible to a plurality of medical practitioners computerized medical records. Also attached to the network 190 may be a Laboratory Information System. In an embodiment, the Laboratory Information System may be a software system which stores information created or generated by clinical laboratories. Also attached to the network 190 may be a Digital Pathology System that may be used to digitally manage and store information related to medical pathology.

Also attached to the network 190 may be one or more Computer Aided Diagnosis Systems (CAD) systems that are generally used to perform Computer-Aided Processing (CAP) such as, for example, CAD processes. In one embodiment, the CAD systems functionality may reside in a computing device and/or system separate from computing system 150 while in another embodiment the CAD systems functionality may reside within computing system 150.

Also attached to the network 190 may be one or more Processing Systems that may be used to perform computerized advanced processing such as, for example, computations on imaging information to create new views of the information, for example, volume rendering and/or other types of processing, for example image enhancement, volume quantification, blood-flow quantification, and the like. In one embodiment, such processing functionality may reside in a computing device and/or system separate from computing system 150 while in another embodiment the processing functionality may reside within computing system 150.

In other embodiments, other computing devices and/or systems that store, provide, acquire, and/or otherwise manipulate medical data may also be coupled to the network 190 and may be in communication with one or more of the devices illustrated in FIG. 1, such as with the computing system 150.

Depending on the embodiment, other devices discussed herein may include some or all of the same components discussed above with reference to the computing system 150 and may perform some or all of the functionality discussed herein.

As mentioned above, various of the image storage 122, the server 120, the user preferences and rules database 124, the external sensor(s) 125, and/or other components described above may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150.

XII. Additional Embodiments

Any process descriptions, elements, or blocks in the flow diagrams described herein and/or depicted in the attached figures should be understood as potentially representing modules, segments, or portions of code which include one or more executable instructions (as described below) for implementing specific logical functions or steps in the process. Alternate implementations are included within the scope of the embodiments described herein in which elements or functions may be deleted, executed out of order from that shown or discussed, including substantially concurrently (for example, through multi-threaded processing, interrupt processing, or multiple processors or processor cores or on other parallel architectures) or in reverse order, depending on the functionality involved.

Any of the methods and processes described above may be partially or fully embodied in, and partially or fully automated via, logic instructions, software code instructions, and/or software code modules executed by one or more general purpose processors and/or application-specific processors (also referred to as "computer devices," "computing devices," "hardware computing devices," "hardware processors," and the like). For example, the methods described herein may be performed as software instructions are executed by, and/or in response to software instruction being executed by, one or more hardware processors (e.g., one or more processors of the computing system 150) and/or any other suitable computing devices. The software instructions and/or other executable code may be read from a tangible computer-readable medium. A tangible computer-readable medium is a data storage device that can store data that is readable by a computer system and/or computing devices. Examples of computer-readable mediums include read-only memory (ROM), random-access memory (RAM), other volatile or non-volatile memory devices, DVD-ROMs, CD-ROMs, magnetic tape, flash drives, and/or optical data storage devices. Accordingly, a software module may reside in RAM memory, flash memory, ROM memory, EPROM memory, EEPROM memory, registers, hard disk, solid state drive, a removable disk, a CD-ROM, a DVD-ROM, and/or any other form of a tangible computer-readable storage medium.

Additionally, any of the methods and processes described above may be partially or fully embodied in, and partially or fully automated via, electronic hardware (for example, logic circuits, hardware processors, and/or the like). For example, the various illustrative logical blocks, methods, routines, and the like described in connection with the embodiments disclosed herein may be implemented as electronic hardware, computer software, or combinations of both. To illustrate this, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments. Further, various features, systems, and processes disclosed herein suitably may be practiced in the absence of any element which is not specifically disclosed herein.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A medical image computing system comprising:
   an electronic display;
   one or more sensors configured to detect a hand of a user;
   a storage device configured to store electronic software instructions;
   one or more data stores storing at least one set of volumetric medical image data; and
   one or more computer processors in communication with the electronic display, the one or more sensors, the storage device, and the one or more data stores, the one or more computer processors configured to execute the stored software instructions to cause the computing system to:
   access, from the one or more data stores, a set of volumetric medical image data;
   render a three-dimensional view of the set of volumetric medical image data;
   generate user interface data for rendering an interactive user interface on the electronic display, the interactive user interface including at least the rendered three-dimensional view of the set of volumetric medical image data;
   determine a virtual origin location in physical space about which a user may move their hand;
   receive sensor data from the one or more sensors, the sensor data indicative of a user input provided via the hand of the user, the user input comprising at least a position of the hand;
   determine, based on the sensor data, the position of the hand with respect to the virtual origin location;
   calculate, based on the position of the hand with respect to the virtual origin location, a rotation of the set of volumetric medical image data;
   render, based on the rotation, an updated three-dimensional view of the set of volumetric medical image data; and
   update the user interface data to include the updated three-dimensional view of the set of volumetric medical image data.

2. The medical image computing system of claim 1, wherein the virtual origin location is determined in reference to at least one of the one or more sensors.

3. The medical image computing system of claim 2, wherein the at least one of the one or more sensors is located on a surface in front of and below the electronic display such that the virtual origin is located in front of the electronic display and the one or more sensors are configured to detect the hand of the user when the hand is positioned above the sensor and in front of the electronic display.

4. The medical image computing system of claim 2, wherein calculating the rotation of the set of volumetric medical image data comprises:

defining a first three-dimensional coordinate system of the at least one of the one or more sensors, wherein the virtual origin is at an origin of the first three-dimensional coordinate system;
determining x and z coordinates of the hand with reference to the first three-dimensional coordinate system;
calculating a first angle between a z-axis of the first three-dimensional coordinate system and the x and z coordinates of the hand with reference to the first three-dimensional coordinate system;
determining a y coordinate of the hand with reference to the first three-dimensional coordinate system;
converting the y coordinate to a value on a scale between a maximum value and a minimum value, wherein the maximum value and the minimum value are associated with respective minimum and maximum physical positions of the users hand along a y-axis of the first three-dimensional coordinate system;
calculating a second angle by taking an arcsin( ) of the value;
defining a second three-dimensional coordinate system of the rendered three-dimensional view of the set of volumetric medical image data;
rotating the rendered three-dimensional view of the set of volumetric medical image data by the first angle about a y-axis of the second three-dimensional coordinate system;
defining a third three-dimensional coordinate system of the electronic display; and
rotating the rendered three-dimensional view of the set of volumetric medical image data by the second angle about an x-axis of the third three-dimensional coordinate system.

5. The medical image computing system of claim 4, wherein the maximum value and minimum value are, respectively, at least one of: −0.99 and +0.99, −0.999 and +0.999, or −1 and +1.

6. The medical image computing system of claim 1, wherein the user input further comprises at least one of: a motion of the hand, a rotation of the hand, an orientation of the hand, or a configuration of the hand.

7. The medical image computing system of claim 6, wherein:
the one or more data stores store a first set of volumetric medical image data and a second set of volumetric medical image data, and
the one or more computer processors are configured to execute the stored software instructions to further cause the computing system to:
determine, based on the sensor data, the configuration of the hand of the user;
select, based on the configuration of the hand of the user, a one of the first set of volumetric medical image data and the second set of volumetric medical image data;
calculate, based on the position of the hand with respect to the virtual origin location, a first rotation of the one of the first set of volumetric medical image data and the second set of volumetric medical image data;
render, based on the first rotation, an updated three-dimensional view of the one of the first set of volumetric medical image data and the second set of volumetric medical image data; and
update the user interface data to include the updated three-dimensional view of the one of the first set of volumetric medical image data and the second set of volumetric medical image data.

8. The medical image computing system of claim 7, wherein:
the one or more computer processors are configured to execute the stored software instructions to further cause the computing system to:
determine, based on the sensor data, a change in the configuration of the hand of the user;
select, based on the change in the configuration of the hand of the user, a second of the first set of volumetric medical image data and the second set of volumetric medical image data;
calculate, based on the position of the hand with respect to the virtual origin location, a second rotation of the second of the first set of volumetric medical image data and the second set of volumetric medical image data;
render, based on the second rotation, an updated three-dimensional view of the second of the first set of volumetric medical image data and the second set of volumetric medical image data; and
update the user interface data to include the updated three-dimensional view of the second of the first set of volumetric medical image data and the second set of volumetric medical image data.

9. The medical image computing system of claim 7, wherein the configuration of the hand of the user comprises at least one of: a fist, one or more fingers extended, or a flat hand.

10. A computer-implemented method comprising:
by one or more computer processors executing software instructions:
accessing, from one or more data stores, a set of volumetric medical image data;
rendering a three-dimensional view of the set of volumetric medical image data;
generating user interface data for rendering an interactive user interface on an electronic display, the interactive user interface including at least the rendered three-dimensional view of the set of volumetric medical image data;
determining a virtual origin location in physical space about which a user may move their hand;
receiving sensor data from one or more sensors configured to detect the hand of the user, the sensor data indicative of a user input provided via the hand of the user, the user input comprising at least a position of the hand;
determining, based on the sensor data, the position of the hand with respect to the virtual origin location;
calculating, based on the position of the hand with respect to the virtual origin location, a rotation of the set of volumetric medical image data;
rendering, based on the rotation, an updated three-dimensional view of the set of volumetric medical image data; and
updating the user interface data to include the updated three-dimensional view of the set of volumetric medical image data.

11. The computer-implemented method of claim 10, wherein calculating the rotation of the set of volumetric medical image data comprises:
by the one or more computer processors executing software instructions:
defining a first three-dimensional coordinate system of the at least one of the one or more sensors, wherein the virtual origin is at an origin of the first three-dimensional coordinate system;
determining x and z coordinates of the hand with reference to the first three-dimensional coordinate system;
calculating a first angle between a z-axis of the first three-dimensional coordinate system and the x and z coordinates of the hand with reference to the first three-dimensional coordinate system;
determining a y coordinate of the hand with reference to the first three-dimensional coordinate system;
converting the y coordinate to a value on a scale between a maximum value and a minimum value, wherein the maximum value and the minimum value are associated with respective minimum and maximum physical positions of the users hand along a y-axis of the first three-dimensional coordinate system;
calculating a second angle by taking an arcsin( ) of the value;
defining a second three-dimensional coordinate system of the rendered three-dimensional view of the set of volumetric medical image data;
rotating the rendered three-dimensional view of the set of volumetric medical image data by the first angle about a y-axis of the second three-dimensional coordinate system;
defining a third three-dimensional coordinate system of the electronic display; and
rotating the rendered three-dimensional view of the set of volumetric medical image data by the second angle about an x-axis of the third three-dimensional coordinate system.

12. The computer-implemented method of claim 10, wherein the user input further comprises at least one of: a motion of the hand, a rotation of the hand, an orientation of the hand, or a configuration of the hand.

13. The computer-implemented method of claim 12, wherein the one or more data stores store a first set of volumetric medical image data and a second set of volumetric medical image data, the computer-implemented method further comprising:
by the one or more computer processors executing software instructions:
determining, based on the sensor data, the configuration of the hand of the user;
selecting, based on the configuration of the hand of the user, a one of the first set of volumetric medical image data and the second set of volumetric medical image data;
calculating, based on the position of the hand with respect to the virtual origin location, a first rotation of the one of the first set of volumetric medical image data and the second set of volumetric medical image data;
rendering, based on the first rotation, an updated three-dimensional view of the one of the first set of volumetric medical image data and the second set of volumetric medical image data; and
updating the user interface data to include the updated three-dimensional view of the one of the first set of volumetric medical image data and the second set of volumetric medical image data.

14. The computer-implemented method of claim 13 further comprising:
by the one or more computer processors executing software instructions:
determining, based on the sensor data, a change in the configuration of the hand of the user;

selecting, based on the change in the configuration of the hand of the user, a second of the first set of volumetric medical image data and the second set of volumetric medical image data;

calculating, based on the position of the hand with respect to the virtual origin location, a second rotation of the second of the first set of volumetric medical image data and the second set of volumetric medical image data;

rendering, based on the second rotation, an updated three-dimensional view of the second of the first set of volumetric medical image data and the second set of volumetric medical image data; and updating the user interface data to include the updated three-dimensional view of the second of the first set of volumetric medical image data and the second set of volumetric medical image data.

15. The computer-implemented method of claim 13, wherein the configuration of the hand of the user comprises at least one of: a fist, one or more fingers extended, or a flat hand.

16. A non-transitory computer-readable storage medium having software instructions embodied therewith, the software instructions executable by one or more processors to cause the one or more processors to:

access, from one or more data stores, a set of volumetric medical image data;

render a three-dimensional view of the set of volumetric medical image data;

generate user interface data for rendering an interactive user interface on an electronic display, the interactive user interface including at least the rendered three-dimensional view of the set of volumetric medical image data;

determine a virtual origin location in physical space about which a user may move their hand;

receive sensor data from one or more sensors configured to detect the hand of the user, the sensor data indicative of a user input provided via the hand of the user, the user input comprising at least a position of the hand;

determine, based on the sensor data, the position of the hand with respect to the virtual origin location;

calculate, based on the position of the hand with respect to the virtual origin location, a rotation of the set of volumetric medical image data;

render, based on the rotation, an updated three-dimensional view of the set of volumetric medical image data; and update the user interface data to include the updated three-dimensional view of the set of volumetric medical image data.

17. The non-transitory computer-readable storage medium of claim 16, wherein calculating the rotation of the set of volumetric medical image data comprises:

defining a first three-dimensional coordinate system of the at least one of the one or more sensors, wherein the virtual origin is at an origin of the first three-dimensional coordinate system;

determining x and z coordinates of the hand with reference to the first three-dimensional coordinate system;

calculating a first angle between a z-axis of the first three-dimensional coordinate system and the x and z coordinates of the hand with reference to the first three-dimensional coordinate system;

determining a y coordinate of the hand with reference to the first three-dimensional coordinate system;

converting the y coordinate to a value on a scale between a maximum value and a minimum value, wherein the maximum value and the minimum value are associated with respective minimum and maximum physical positions of the users hand along a y-axis of the first three-dimensional coordinate system;

calculating a second angle by taking an arcsin( ) of the value;

defining a second three-dimensional coordinate system of the rendered three-dimensional view of the set of volumetric medical image data;

rotating the rendered three-dimensional view of the set of volumetric medical image data by the first angle about a y-axis of the second three-dimensional coordinate system;

defining a third three-dimensional coordinate system of the electronic display; and rotating the rendered three-dimensional view of the set of volumetric medical image data by the second angle about an x-axis of the third three-dimensional coordinate system.

18. The non-transitory computer-readable storage medium of claim 16, wherein the user input further comprises at least one of: a motion of the hand, a rotation of the hand, an orientation of the hand, or a configuration of the hand.

19. The non-transitory computer-readable storage medium of claim 18, wherein the one or more data stores store a first set of volumetric medical image data and a second set of volumetric medical image data, and wherein the software instructions are further executable by one or more processors to cause the one or more processors to:

determine, based on the sensor data, the configuration of the hand of the user;

selecting, based on the configuration of the hand of the user, a one of the first set of volumetric medical image data and the second set of volumetric medical image data;

calculate, based on the position of the hand with respect to the virtual origin location, a first rotation of the one of the first set of volumetric medical image data and the second set of volumetric medical image data;

render, based on the first rotation, an updated three-dimensional view of the one of the first set of volumetric medical image data and the second set of volumetric medical image data; and update the user interface data to include the updated three-dimensional view of the one of the first set of volumetric medical image data and the second set of volumetric medical image data.

20. The non-transitory computer-readable storage medium of claim 19, wherein the software instructions are further executable by one or more processors to cause the one or more processors to:

determine, based on the sensor data, a change in the configuration of the hand of the user;

select, based on the change in the configuration of the hand of the user, a second of the first set of volumetric medical image data and the second set of volumetric medical image data;

calculate, based on the position of the hand with respect to the virtual origin location, a second rotation of the second of the first set of volumetric medical image data and the second set of volumetric medical image data;

render, based on the second rotation, an updated three-dimensional view of the second of the first set of volumetric medical image data and the second set of volumetric medical image data; and update the user interface data to include the updated three-dimensional view of the second of the first set of volumetric medical image data and the second set of volumetric medical image data.

\* \* \* \* \*